(12) United States Patent
Spehr et al.

(10) Patent No.: US 8,244,371 B2
(45) Date of Patent: Aug. 14, 2012

(54) PANCREAS LEAD

(75) Inventors: Paul Richard Spehr, Medford, NJ (US); Tamir Levi, Doar-Na Havel Megiddo (IL); Benny Rousso, Rishon-LeZion (IL)

(73) Assignee: MetaCure Limited, Hamilton (BM)

( * ) Notice: Subject to any disclaimer, the term of this patent is extended or adjusted under 35 U.S.C. 154(b) by 827 days.

(21) Appl. No.: 11/886,154

(22) PCT Filed: Mar. 16, 2006

(86) PCT No.: PCT/IL2006/000345
§ 371 (c)(1),
(2), (4) Date: May 15, 2008

(87) PCT Pub. No.: WO2006/097934
PCT Pub. Date: Sep. 21, 2006

(65) Prior Publication Data
US 2009/0062893 A1    Mar. 5, 2009

Related U.S. Application Data

(63) Continuation-in-part of application No. PCT/IL2005/000316, filed on Mar. 18, 2005.

(60) Provisional application No. 60/719,421, filed on Sep. 22, 2005, provisional application No. 60/719,517, filed on Sep. 22, 2005.

(51) Int. Cl.
*A61N 1/05* (2006.01)

(52) U.S. Cl. .......... 607/116; 607/1; 607/2; 607/40; 607/115; 607/133; 600/300; 600/372; 600/373; 600/375; 600/377; 600/386

(58) Field of Classification Search .......... 607/1–2, 607/40, 115–116, 133; 600/300, 372, 373, 600/375, 377, 386
See application file for complete search history.

(56) References Cited

U.S. PATENT DOCUMENTS

| | | | |
|---|---|---|---|
| 1,918,386 A | 7/1933 | Esau |
| 3,211,154 A | 10/1965 | Becker et al. |
| 3,541,390 A | 11/1970 | Jahnke |
| 3,572,345 A | 3/1971 | Auphan |
| 3,587,567 A | 6/1971 | Schiff |
| 3,651,805 A | 3/1972 | Brelling |
| 3,651,806 A | 3/1972 | Hirshberg |
| 3,796,221 A | 3/1974 | Hagfors |
| 3,911,930 A | 10/1975 | Hagfors et al. |
| 3,924,641 A | 12/1975 | Weiss |
| 3,933,147 A | 1/1976 | Du Vall et al. |
| 3,942,536 A | 3/1976 | Mirowski et al. |

(Continued)

FOREIGN PATENT DOCUMENTS
EP 0148687 7/1985

(Continued)

OTHER PUBLICATIONS

Invitation Pursuant to Rule 62a(1) EPC and Rule 63(1) EPC Dated May 5, 2010 From the European Patent Office Re.: Application No. 04719312.3.

(Continued)

*Primary Examiner* — Carl H Layno
*Assistant Examiner* — Deborah Malamud

(57) ABSTRACT

An implant device comprising an electrode for electrical stimulation of the pancreas, the device being adapted to be inserted into the pancreas, and to change at least one of its properties after being inserted into the pancreas, so that it will cause less irritation to the pancreas than before changing said property.

29 Claims, 15 Drawing Sheets

U.S. PATENT DOCUMENTS

| | | |
|---|---|---|
| 3,944,740 A | 3/1976 | Murase et al. |
| 3,952,750 A | 4/1976 | Mirowski et al. |
| 4,030,509 A | 6/1977 | Heilman et al. |
| 4,055,190 A | 10/1977 | Tany |
| 4,106,494 A | 8/1978 | McEachern |
| 4,164,216 A | 8/1979 | Person |
| 4,168,711 A | 9/1979 | Cannon, III et al. |
| 4,184,493 A | 1/1980 | Langer et al. |
| 4,202,340 A | 5/1980 | Langer et al. |
| 4,223,678 A | 9/1980 | Langer et al. |
| 4,237,895 A | 12/1980 | Johnson |
| 4,273,114 A | 6/1981 | Berkalow et al. |
| 4,293,734 A | 10/1981 | Pepper, Jr. |
| 4,312,354 A | 1/1982 | Walters |
| 4,315,503 A | 2/1982 | Ryaby et al. |
| 4,316,472 A | 2/1982 | Mirowski et al. |
| 4,337,776 A | 7/1982 | Daly et al. |
| 4,369,791 A | 1/1983 | Friedman |
| 4,384,585 A | 5/1983 | Zipes |
| 4,387,717 A | 6/1983 | Brownlee et al. |
| 4,403,614 A | 9/1983 | Engle et al. |
| 4,406,288 A | 9/1983 | Horwinski et al. |
| 4,407,288 A | 10/1983 | Langer et al. |
| 4,411,268 A | 10/1983 | Cox |
| 4,428,366 A | 1/1984 | Findl et al. |
| 4,440,172 A | 4/1984 | Langer |
| 4,506,680 A | 3/1985 | Stokes |
| 4,537,195 A | 8/1985 | McDonnell |
| 4,537,203 A | 8/1985 | Machida |
| 4,543,738 A | 10/1985 | Mower |
| 4,543,956 A | 10/1985 | Herscovici |
| 4,550,221 A | 10/1985 | Mabusth |
| 4,554,922 A | 11/1985 | Prystowsky et al. |
| 4,554,992 A | 11/1985 | Kassai |
| 4,559,946 A | 12/1985 | Mower |
| 4,559,947 A | 12/1985 | Renger et al. |
| 4,566,456 A | 1/1986 | Koning et al. |
| 4,572,191 A | 2/1986 | Mirowski et al. |
| 4,628,934 A | 12/1986 | Pohndorf et al. |
| 4,637,397 A | 1/1987 | Jones et al. |
| 4,639,720 A | 1/1987 | Rympalski et al. |
| 4,651,716 A | 3/1987 | Forester et al. |
| 4,674,508 A | 6/1987 | DeCote |
| 4,679,572 A | 7/1987 | Baker |
| 4,686,332 A | 8/1987 | Greanias et al. |
| 4,690,155 A | 9/1987 | Hess |
| 4,693,253 A | 9/1987 | Adams |
| 4,708,145 A | 11/1987 | Tacker et al. |
| 4,717,581 A | 1/1988 | Robblee |
| 4,726,279 A | 2/1988 | Kepler et al. |
| 4,726,379 A | 2/1988 | Altman et al. |
| 4,765,341 A | 8/1988 | Mower et al. |
| 4,807,632 A | 2/1989 | Liess et al. |
| 4,830,006 A | 5/1989 | Haluska et al. |
| 4,834,100 A | 5/1989 | Charms |
| 4,850,959 A | 7/1989 | Findl |
| 4,870,974 A | 10/1989 | Wang |
| 4,878,553 A | 11/1989 | Yamanami et al. |
| 4,884,576 A | 12/1989 | Alt |
| 4,914,624 A | 4/1990 | Dunthorn et al. |
| 4,928,688 A | 5/1990 | Mower |
| 4,967,749 A | 11/1990 | Cohen |
| 4,971,058 A | 11/1990 | Pless et al. |
| 4,979,507 A | 12/1990 | Heinz et al. |
| 4,988,837 A | 1/1991 | Murakami et al. |
| 4,996,984 A | 3/1991 | Sweeney |
| 4,998,531 A | 3/1991 | Bocchi et al. |
| 4,998,532 A | 3/1991 | Griffith |
| 5,002,052 A | 3/1991 | Haluska et al. |
| 5,003,976 A | 4/1991 | Alt |
| 5,018,522 A | 5/1991 | Mehra |
| 5,020,544 A | 6/1991 | Dahl et al. |
| 5,022,396 A | 6/1991 | Watanabe |
| 5,026,397 A | 6/1991 | Aoki et al. |
| 5,031,617 A | 7/1991 | Klettner |
| 5,041,107 A | 8/1991 | Heil, Jr. |
| 5,044,375 A | 9/1991 | Bach et al. |
| 5,048,522 A | 9/1991 | Petrofsky |
| 5,050,612 A | 9/1991 | Matsumura |
| 5,063,929 A | 11/1991 | Bartelt et al. |
| 5,083,564 A | 1/1992 | Scherlag |
| 5,085,218 A | 2/1992 | Heil et al. |
| 5,087,243 A | 2/1992 | Avitall |
| 5,097,832 A | 3/1992 | Buchanan |
| 5,097,833 A | 3/1992 | Campos |
| 5,097,843 A | 3/1992 | Soukup et al. |
| 5,101,814 A | 4/1992 | Palti |
| 5,107,834 A | 4/1992 | Ideker et al. |
| 5,111,814 A | 5/1992 | Goldfarb |
| 5,111,815 A | 5/1992 | Mower |
| 5,129,394 A | 7/1992 | Mehra |
| 5,133,354 A | 7/1992 | Kallok |
| 5,137,021 A | 8/1992 | Wayne et al. |
| 5,144,554 A | 9/1992 | Zhang et al. |
| 5,154,501 A | 10/1992 | Svenson et al. |
| 5,156,147 A | 10/1992 | Warren et al. |
| 5,156,149 A | 10/1992 | Hudrlik |
| 5,161,527 A | 11/1992 | Nappholz et al. |
| 5,163,427 A | 11/1992 | Keimel |
| 5,163,428 A | 11/1992 | Pless |
| 5,172,690 A | 12/1992 | Nappholz et al. |
| 5,172,699 A | 12/1992 | Svenson et al. |
| 5,174,286 A | 12/1992 | Chirife |
| 5,184,616 A | 2/1993 | Weiss |
| 5,184,620 A | 2/1993 | Cudahy et al. |
| 5,185,620 A | 2/1993 | Cooper |
| 5,188,104 A | 2/1993 | Wernicke et al. |
| 5,188,106 A | 2/1993 | Nappholz et al. |
| 5,190,036 A | 3/1993 | Linder |
| 5,190,041 A | 3/1993 | Palti |
| 5,190,141 A | 3/1993 | Boldrini et al. |
| 5,199,428 A | 4/1993 | Obel et al. |
| 5,205,284 A | 4/1993 | Freeman |
| 5,213,098 A | 5/1993 | Bennett et al. |
| 5,231,381 A | 7/1993 | Duwaer |
| 5,231,988 A | 8/1993 | Wernicke et al. |
| 5,233,985 A | 8/1993 | Hudrlik |
| 5,236,413 A | 8/1993 | Feiring |
| 5,243,980 A | 9/1993 | Mehra et al. |
| 5,267,560 A | 12/1993 | Cohen |
| 5,281,219 A | 1/1994 | Kallok |
| 5,282,785 A | 2/1994 | Shapland et al. |
| 5,284,491 A | 2/1994 | Sutton et al. |
| 5,286,254 A | 2/1994 | Shapland et al. |
| 5,292,344 A | 3/1994 | Douglas |
| 5,305,745 A | 4/1994 | Zacouto |
| 5,318,591 A | 6/1994 | Causey, III et al. |
| 5,320,642 A | 6/1994 | Scheriag |
| 5,320,643 A | 6/1994 | Roline et al. |
| 5,324,327 A | 6/1994 | Cohen |
| 5,325,856 A | 7/1994 | Nitzsche et al. |
| 5,327,887 A | 7/1994 | Nowakowski |
| 5,346,506 A | 9/1994 | Mower et al. |
| 5,350,403 A | 9/1994 | Stroetmann et al. |
| 5,353,800 A | 10/1994 | Pohndorf et al. |
| 5,365,461 A | 11/1994 | Stein et al. |
| 5,366,485 A | 11/1994 | Kroll et al. |
| 5,366,486 A | 11/1994 | Zipes et al. |
| 5,368,040 A | 11/1994 | Carney |
| 5,370,665 A | 12/1994 | Hudrlik |
| 5,374,787 A | 12/1994 | Miller et al. |
| 5,381,160 A | 1/1995 | Landmeier |
| 5,386,835 A | 2/1995 | Elphick et al. |
| 5,386,837 A | 2/1995 | Sterzer |
| 5,387,419 A | 2/1995 | Levy et al. |
| 5,391,192 A | 2/1995 | Lu et al. |
| 5,391,199 A | 2/1995 | Ben-Haim |
| 5,397,344 A | 3/1995 | Garfield et al. |
| 5,398,683 A | 3/1995 | Edwards et al. |
| 5,402,151 A | 3/1995 | Duwaer |
| 5,411,531 A | 5/1995 | Hill et al. |
| 5,415,629 A | 5/1995 | Henley |
| 5,417,717 A | 5/1995 | Salo et al. |
| 5,419,763 A | 5/1995 | Hildebrand |
| 5,423,872 A | 6/1995 | Cigaina |
| 5,425,363 A | 6/1995 | Wang |
| 5,431,682 A | 7/1995 | Hedberg |

| Patent | Date | Inventor |
|---|---|---|
| 5,431,688 A | 7/1995 | Freeman |
| 5,431,693 A | 7/1995 | Schroeppel |
| 5,433,730 A | 7/1995 | Alt |
| 5,443,485 A | 8/1995 | Housworth et al. |
| 5,443,489 A | 8/1995 | Ben-Haim |
| 5,445,609 A | 8/1995 | Lattin et al. |
| 5,447,520 A | 9/1995 | Spano et al. |
| 5,447,525 A | 9/1995 | Powell et al. |
| 5,447,526 A | 9/1995 | Karsdon |
| 5,458,568 A | 10/1995 | Racchini et al. |
| 5,464,020 A | 11/1995 | Lerner |
| 5,464,429 A | 11/1995 | Hedberg et al. |
| 5,468,254 A | 11/1995 | Hahn et al. |
| 5,472,453 A | 12/1995 | Alt |
| 5,476,484 A | 12/1995 | Hedberg |
| 5,476,485 A | 12/1995 | Weinberg et al. |
| 5,476,487 A | 12/1995 | Sholder |
| 5,476,497 A | 12/1995 | Mower et al. |
| 5,480,422 A | 1/1996 | Ben-Haim |
| 5,482,052 A | 1/1996 | Lerner |
| 5,489,293 A | 2/1996 | Pless et al. |
| 5,495,077 A | 2/1996 | Miller et al. |
| 5,499,971 A | 3/1996 | Shapland et al. |
| 5,501,662 A | 3/1996 | Hofmann |
| 5,505,700 A | 4/1996 | Leone et al. |
| 5,510,813 A | 4/1996 | Makinwa et al. |
| 5,514,162 A | 5/1996 | Bornzin et al. |
| 5,520,642 A | 5/1996 | Bigagli et al. |
| 5,522,853 A | 6/1996 | Kroll |
| 5,527,345 A | 6/1996 | Infinger |
| 5,528,002 A | 6/1996 | Katabami |
| 5,531,764 A | 7/1996 | Adams et al. |
| 5,534,015 A | 7/1996 | Kroll et al. |
| 5,540,722 A | 7/1996 | Clare et al. |
| 5,540,730 A | 7/1996 | Terry, Jr. et al. |
| 5,540,734 A | 7/1996 | Zabara |
| 5,543,588 A | 8/1996 | Bisset et al. |
| 5,543,589 A | 8/1996 | Buchana et al. |
| 5,546,951 A | 8/1996 | Ben-Haim |
| 5,549,646 A | 8/1996 | Katz et al. |
| 5,556,421 A | 9/1996 | Prutchi et al. |
| 5,556,760 A | 9/1996 | Nakamura et al. |
| 5,558,640 A | 9/1996 | Pfeiler et al. |
| 5,561,165 A | 10/1996 | Lautt et al. |
| 5,562,708 A | 10/1996 | Combs et al. |
| 5,565,632 A | 10/1996 | Ogawa |
| 5,568,809 A | 10/1996 | Ben-Haim |
| 5,571,143 A | 11/1996 | Hoegnelid et al. |
| 5,571,997 A | 11/1996 | Gray et al. |
| 5,578,061 A | 11/1996 | Stroetmann et al. |
| 5,584,803 A | 12/1996 | Stevens et al. |
| 5,584,804 A | 12/1996 | Klatz et al. |
| 5,584,868 A | 12/1996 | Salo et al. |
| 5,587,200 A | 12/1996 | Lorenz et al. |
| 5,589,856 A | 12/1996 | Stein et al. |
| 5,601,609 A | 2/1997 | Duncan |
| 5,601,611 A | 2/1997 | Fayram et al. |
| 5,620,468 A | 4/1997 | Mongeon et al. |
| 5,622,687 A | 4/1997 | Krishnan et al. |
| 5,626,622 A | 5/1997 | Cooper |
| 5,632,267 A | 5/1997 | Högnelid et al. |
| 5,634,895 A | 6/1997 | Igo et al. |
| 5,634,899 A | 6/1997 | Shapland et al. |
| 5,649,966 A | 7/1997 | Noren et al. |
| 5,651,378 A | 7/1997 | Matheny et al. |
| 5,654,030 A | 8/1997 | Munshi et al. |
| 5,662,687 A | 9/1997 | Hedberg et al. |
| 5,670,755 A | 9/1997 | Kwon |
| 5,674,251 A | 10/1997 | Combs et al. |
| 5,674,259 A | 10/1997 | Gray |
| 5,683,429 A | 11/1997 | Mehra |
| 5,683,431 A | 11/1997 | Wang |
| 5,687,734 A | 11/1997 | Dempsey et al. |
| 5,690,691 A | 11/1997 | Chen et al. |
| 5,694,945 A | 12/1997 | Ben-Haim |
| 5,697,953 A | 12/1997 | Kroll et al. |
| 5,713,924 A | 2/1998 | Min et al. |
| 5,713,929 A | 2/1998 | Hess et al. |
| 5,713,935 A | 2/1998 | Prutchi et al. |
| 5,720,768 A | 2/1998 | Verboven-Nelissen |
| 5,735,876 A | 4/1998 | Kroll et al. |
| 5,738,096 A | 4/1998 | Ben-Haim |
| 5,738,105 A | 4/1998 | Kroll |
| 5,741,211 A | 4/1998 | Renirie et al. |
| 5,741,791 A | 4/1998 | Olsen |
| 5,749,906 A | 5/1998 | Kieval et al. |
| 5,755,740 A | 5/1998 | Nappholtz |
| 5,777,607 A | 7/1998 | Koolen |
| 5,779,661 A | 7/1998 | Stephen et al. |
| 5,782,876 A | 7/1998 | Flammang |
| 5,782,881 A | 7/1998 | Lu et al. |
| 5,783,951 A | 7/1998 | Inoue et al. |
| 5,790,106 A | 8/1998 | Hirano et al. |
| 5,790,107 A | 8/1998 | Kasser et al. |
| 5,792,189 A | 8/1998 | Gray et al. |
| 5,792,198 A | 8/1998 | Nappholz |
| 5,792,208 A | 8/1998 | Gray |
| 5,797,967 A | 8/1998 | Kenknight |
| 5,800,464 A | 9/1998 | Kieval |
| 5,807,234 A | 9/1998 | Bui et al. |
| 5,807,306 A | 9/1998 | Shapland et al. |
| 5,814,079 A | 9/1998 | Kieval |
| 5,824,016 A | 10/1998 | Ekwall |
| 5,825,352 A | 10/1998 | Bisset et al. |
| 5,841,078 A | 11/1998 | Miller et al. |
| 5,844,506 A | 12/1998 | Binstead |
| 5,854,881 A | 12/1998 | Yoshida et al. |
| 5,861,014 A | 1/1999 | Familoni |
| 5,861,583 A | 1/1999 | Schediwy et al. |
| 5,865,787 A | 2/1999 | Shapland et al. |
| 5,871,506 A | 2/1999 | Mower |
| 5,906,607 A | 5/1999 | Taylor et al. |
| 5,911,223 A | 6/1999 | Weaver et al. |
| 5,913,876 A | 6/1999 | Taylor et al. |
| 5,914,465 A | 6/1999 | Allen et al. |
| 5,919,216 A | 7/1999 | Houben et al. |
| 5,920,309 A | 7/1999 | Bisset et al. |
| 5,927,284 A | 7/1999 | Borst et al. |
| 5,954,761 A | 9/1999 | Machek et al. |
| 5,956,020 A | 9/1999 | D'Amico et al. |
| 5,962,246 A | 10/1999 | Ladner et al. |
| 5,991,649 A | 11/1999 | Garfield et al. |
| 5,995,872 A | 11/1999 | Bourgeois |
| 6,002,594 A | 12/1999 | Ledin et al. |
| 6,006,134 A | 12/1999 | Hill et al. |
| 6,023,640 A | 2/2000 | Ross |
| 6,026,326 A | 2/2000 | Bardy |
| 6,032,074 A | 2/2000 | Collins |
| 6,032,672 A | 3/2000 | Taylor |
| 6,037,882 A | 3/2000 | Levy |
| 6,041,252 A | 3/2000 | Walker et al. |
| 6,057,374 A | 5/2000 | Huntington et al. |
| 6,066,163 A | 5/2000 | John |
| 6,067,470 A | 5/2000 | Mower |
| 6,071,305 A | 6/2000 | Brown et al. |
| 6,075,520 A | 6/2000 | Inoue et al. |
| 6,083,249 A | 7/2000 | Familoni |
| 6,086,582 A | 7/2000 | Altman et al. |
| 6,093,167 A | 7/2000 | Houben et al. |
| 6,122,536 A | 9/2000 | Sun et al. |
| 6,128,007 A | 10/2000 | Seybold et al. |
| 6,133,906 A | 10/2000 | Geaghan |
| 6,135,978 A | 10/2000 | Houben et al. |
| 6,136,019 A | 10/2000 | Mower |
| 6,141,586 A | 10/2000 | Mower |
| 6,141,587 A | 10/2000 | Mower |
| 6,151,586 A | 11/2000 | Brown |
| 6,178,351 B1 | 1/2001 | Mower |
| 6,185,452 B1 | 2/2001 | Schulman et al. |
| 6,233,484 B1 | 5/2001 | Ben-Haim et al. |
| 6,233,487 B1 | 5/2001 | Mika et al. |
| 6,236,887 B1 | 5/2001 | Ben-Haim et al. |
| 6,239,389 B1 | 5/2001 | Allen et al. |
| 6,243,607 B1 | 6/2001 | Mintchev et al. |
| 6,261,280 B1 | 7/2001 | Houben et al. |
| 6,278,443 B1 | 8/2001 | Amro et al. |
| 6,285,906 B1 | 9/2001 | Ben Haim et al. |
| 6,292,693 B1 | 9/2001 | Darvish et al. |

| Patent No. | Date | Inventor |
|---|---|---|
| 6,292,704 B1 | 9/2001 | Malonek et al. |
| 6,295,470 B1 | 9/2001 | Mower |
| 6,296,693 B1 | 10/2001 | McCarthy |
| 6,298,254 B2 | 10/2001 | Tamada |
| 6,298,268 B1 | 10/2001 | Ben-Haim et al. |
| 6,317,631 B1 | 11/2001 | Ben-Haim et al. |
| 6,330,476 B1 | 12/2001 | Ben-Haim |
| 6,337,995 B1 | 1/2002 | Mower |
| 6,341,235 B1 | 1/2002 | Mower |
| 6,343,232 B1 | 1/2002 | Mower |
| 6,363,279 B1 | 3/2002 | Ben-Haim et al. |
| 6,381,495 B1 | 4/2002 | Jenkins |
| 6,392,636 B1 | 5/2002 | Ferrari et al. |
| 6,411,847 B1 | 6/2002 | Mower |
| 6,415,178 B1 | 7/2002 | Ben-Haim et al. |
| 6,417,846 B1 | 7/2002 | Lee |
| 6,424,864 B1 | 7/2002 | Matsuura |
| 6,433,069 B1 | 8/2002 | Oeltjen et al. |
| 6,449,511 B1 | 9/2002 | Mintchev et al. |
| 6,452,514 B1 | 9/2002 | Philipp |
| 6,453,199 B1 | 9/2002 | Kobozev |
| 6,463,323 B1 | 10/2002 | Conrad-Vlasak et al. |
| 6,463,324 B1 | 10/2002 | Ben-Haim et al. |
| 6,469,719 B1 | 10/2002 | Kino et al. |
| 6,473,069 B1 | 10/2002 | Gerpheide |
| 6,498,944 B1 | 12/2002 | Ben-Haim et al. |
| 6,504,530 B1 | 1/2003 | Wilson et al. |
| 6,505,745 B1 | 1/2003 | Anderson |
| 6,507,093 B2 | 1/2003 | Kaneda et al. |
| 6,555,235 B1 | 4/2003 | Aufderheide et al. |
| RE38,119 E | 5/2003 | Mower |
| 6,558,345 B1 | 5/2003 | Houben et al. |
| 6,567,700 B1 | 5/2003 | Turcott et al. |
| 6,570,557 B1 | 5/2003 | Westerman et al. |
| 6,571,127 B1 | 5/2003 | Ben-Haim et al. |
| 6,572,542 B1 | 6/2003 | Houben et al. |
| 6,583,676 B2 | 6/2003 | Krah et al. |
| 6,587,093 B1 | 7/2003 | Shaw et al. |
| 6,587,721 B1 | 7/2003 | Prutchi et al. |
| 6,600,953 B2 | 7/2003 | Flesler et al. |
| 6,605,039 B2 | 8/2003 | Houben et al. |
| 6,611,258 B1 | 8/2003 | Tanaka et al. |
| 6,612,983 B1 | 9/2003 | Marchal |
| 6,630,123 B1 | 10/2003 | Woltering et al. |
| 6,633,280 B1 | 10/2003 | Matsumoto et al. |
| 6,634,895 B2 | 10/2003 | Agro |
| 6,652,444 B1 | 11/2003 | Ross |
| 6,658,297 B2 | 12/2003 | Loeb |
| 6,667,740 B2 | 12/2003 | Ely et al. |
| 6,684,104 B2 | 1/2004 | Gordon et al. |
| 6,690,156 B1 | 2/2004 | Weiner et al. |
| 6,690,963 B2 | 2/2004 | Ben-Haim et al. |
| 6,762,752 B2 | 7/2004 | Perski et al. |
| 6,781,577 B2 | 8/2004 | Shigetaka |
| 6,810,286 B2 | 10/2004 | Donovan et al. |
| 6,853,862 B1 | 2/2005 | Marchal et al. |
| 6,875,605 B1 | 4/2005 | Ma |
| 6,919,205 B2 | 7/2005 | Brighton |
| 6,949,081 B1 | 9/2005 | Chance |
| 7,006,871 B1 | 2/2006 | Darvish et al. |
| 7,027,863 B1 | 4/2006 | Prutchi et al. |
| 7,062,318 B2 | 6/2006 | Ben-Haim et al. |
| 7,076,306 B2 | 7/2006 | Marchal et al. |
| 7,092,753 B2 | 8/2006 | Darvish et al. |
| 7,167,748 B2 | 1/2007 | Ben-Haim et al. |
| 7,171,263 B2 | 1/2007 | Darvish et al. |
| 7,190,997 B1 | 3/2007 | Darvish et al. |
| 7,218,963 B2 | 5/2007 | Ben-Haim et al. |
| 7,440,806 B1 | 10/2008 | Whitehurst et al. |
| 7,460,907 B1 | 12/2008 | Darvish et al. |
| 7,840,262 B2 | 11/2010 | Mika et al. |
| 2002/0026141 A1 | 2/2002 | Houben et al. |
| 2002/0052632 A1 | 5/2002 | Ben-Haim et al. |
| 2002/0065455 A1 | 5/2002 | Ben-Haim et al. |
| 2002/0081732 A1 | 6/2002 | Bowlin et al. |
| 2002/0123771 A1 | 9/2002 | Ideker et al. |
| 2002/0161414 A1 | 10/2002 | Flesler et al. |
| 2002/0183682 A1 | 12/2002 | Darvish et al. |
| 2002/0183686 A1 | 12/2002 | Darvish et al. |
| 2003/0018367 A1 | 1/2003 | DiLorenzo |
| 2003/0028221 A1 | 2/2003 | Zhu et al. |
| 2003/0040777 A1 | 2/2003 | Shemer et al. |
| 2003/0055464 A1 | 3/2003 | Darvish et al. |
| 2003/0055466 A1 | 3/2003 | Ben-Haim et al. |
| 2003/0055467 A1 | 3/2003 | Ben-Haim et al. |
| 2003/0100889 A1 | 5/2003 | Duverger et al. |
| 2003/0167476 A1 | 9/2003 | Conklin |
| 2003/0181958 A1 | 9/2003 | Dobak, III |
| 2003/0188899 A1 | 10/2003 | Chao et al. |
| 2003/0208242 A1 | 11/2003 | Harel et al. |
| 2003/0211475 A1 | 11/2003 | Roberts |
| 2004/0044376 A1 | 3/2004 | Flesler et al. |
| 2004/0059393 A1 | 3/2004 | Policker et al. |
| 2004/0095333 A1 | 5/2004 | Morag et al. |
| 2004/0105040 A1 | 6/2004 | Oh et al. |
| 2004/0106954 A1 | 6/2004 | Whitehurst et al. |
| 2004/0138710 A1 | 7/2004 | Shemer et al. |
| 2004/0147816 A1 | 7/2004 | Policker et al. |
| 2004/0155871 A1 | 8/2004 | Perski et al. |
| 2004/0158289 A1 | 8/2004 | Girouard et al. |
| 2004/0230273 A1 | 11/2004 | Cates et al. |
| 2004/0243190 A1 | 12/2004 | Ben-Haim et al. |
| 2004/0249421 A1 | 12/2004 | Harel et al. |
| 2005/0033396 A1 | 2/2005 | Ospyka |
| 2005/0065553 A1 | 3/2005 | Ben Ezra et al. |
| 2005/0095227 A1 | 5/2005 | Rosenzweig et al. |
| 2005/0192542 A1 | 9/2005 | Dev et al. |
| 2006/0036126 A1 | 2/2006 | Ross et al. |
| 2006/0074459 A1 | 4/2006 | Flesler et al. |
| 2006/0079475 A1 | 4/2006 | Zhang et al. |
| 2006/0085045 A1 | 4/2006 | Harel et al. |
| 2006/0097991 A1 | 5/2006 | Hotelling et al. |
| 2006/0184207 A1 | 8/2006 | Darvish et al. |
| 2007/0016262 A1 | 1/2007 | Gross et al. |
| 2007/0027487 A1 | 2/2007 | Mika et al. |
| 2007/0027490 A1 | 2/2007 | Ben-Haim et al. |
| 2007/0027493 A1 | 2/2007 | Ben-Haim et al. |
| 2007/0051849 A1 | 3/2007 | Watts et al. |
| 2007/0060812 A1 | 3/2007 | Harel et al. |
| 2007/0060971 A1 | 3/2007 | Glasberg et al. |
| 2007/0088393 A1 | 4/2007 | Ben-Haim et al. |
| 2007/0092446 A1 | 4/2007 | Haddad et al. |
| 2007/0156177 A1 | 7/2007 | Harel et al. |
| 2007/0161851 A1 | 7/2007 | Takizawa et al. |
| 2007/0162079 A1 | 7/2007 | Shemer et al. |
| 2007/0171211 A1 | 7/2007 | Perski et al. |
| 2007/0179556 A1 | 8/2007 | Ben Haim et al. |
| 2007/0185540 A1 | 8/2007 | Ben-Haim et al. |
| 2007/0239216 A9 | 10/2007 | Shemer et al. |
| 2007/0293901 A1 | 12/2007 | Rousso et al. |
| 2007/0299320 A1 | 12/2007 | Policker et al. |
| 2008/0058879 A1 | 3/2008 | Ben-Haim et al. |
| 2008/0058889 A1 | 3/2008 | Ben-Haim et al. |
| 2008/0058891 A1 | 3/2008 | Ben-Haim et al. |
| 2008/0065159 A1 | 3/2008 | Ben-Haim et al. |
| 2008/0065163 A1 | 3/2008 | Ben-Haim et al. |
| 2008/0065164 A1 | 3/2008 | Ben-Haim et al. |
| 2008/0065168 A1 | 3/2008 | Bitton et al. |
| 2008/0140142 A1 | 6/2008 | Darvish et al. |
| 2008/0178684 A1 | 7/2008 | Spehr |
| 2009/0062893 A1 | 3/2009 | Spehr et al. |
| 2009/0088816 A1 | 4/2009 | Harel et al. |
| 2009/0118797 A1 | 5/2009 | Kliger et al. |
| 2009/0131993 A1 | 5/2009 | Rousso et al. |
| 2009/0204063 A1 | 8/2009 | Policker et al. |
| 2009/0281449 A1 | 11/2009 | Thrower et al. |
| 2009/0292324 A1 | 11/2009 | Rousso et al. |
| 2010/0016923 A1 | 1/2010 | Rousso et al. |
| 2010/0228105 A1 | 9/2010 | Policker et al. |
| 2010/0305468 A1 | 12/2010 | Policker et al. |
| 2010/0324644 A1 | 12/2010 | Levi et al. |

FOREIGN PATENT DOCUMENTS

| | | |
|---|---|---|
| EP | 0156593 | 10/1985 |
| EP | 0250931 | 1/1988 |
| EP | 0314078 | 5/1989 |
| EP | 0481684 | 4/1992 |
| EP | 0503839 | 9/1992 |

| | | |
|---|---|---|
| EP | 0528751 | 2/1993 |
| EP | 0220916 | 4/1994 |
| EP | 0727241 | 8/1996 |
| EP | 1263498 | 12/2002 |
| EP | 0910429 | 3/2005 |
| GB | 1394171 | 5/1975 |
| GB | 2280377 | 2/1995 |
| JP | 62-112530 | 5/1987 |
| JP | 62-275471 | 11/1987 |
| JP | 04-117967 | 4/1992 |
| JP | 04117967 | 4/1992 |
| JP | 04-282168 | 10/1992 |
| JP | 04-365493 | 12/1992 |
| JP | 4365493 | 12/1992 |
| JP | 06-169998 | 6/1994 |
| JP | 06-506619 | 7/1994 |
| JP | 07-503865 | 4/1995 |
| JP | 07-126600 | 5/1995 |
| JP | 7126600 | 5/1995 |
| JP | 07-144024 | 6/1995 |
| JP | 08-243176 | 9/1996 |
| JP | 8243176 | 9/1996 |
| RU | 386634 | 6/1973 |
| RU | 553977 | 5/1977 |
| RU | 831131 | 5/1981 |
| RU | 2014844 | 6/1994 |
| RU | 1827793 | 5/1995 |
| RU | 2055606 | 3/1996 |
| RU | 2075980 | 3/1997 |
| RU | 2077273 | 4/1997 |
| RU | 2078547 | 5/1997 |
| WO | WO 2005/114369 | 0/2005 |
| WO | WO 91/19534 | 12/1991 |
| WO | WO 92/00716 | 1/1992 |
| WO | WO 92/13592 | 8/1992 |
| WO | WO 93/02743 | 2/1993 |
| WO | WO 93/02745 | 2/1993 |
| WO | WO 93/08874 | 5/1993 |
| WO | WO 93/18820 | 9/1993 |
| WO | WO 94/17855 | 8/1994 |
| WO | WO 95/02995 | 2/1995 |
| WO | WO 95/08316 | 3/1995 |
| WO | WO 96/05768 | 2/1996 |
| WO | WO 96/10358 | 4/1996 |
| WO | WO 96/16696 | 6/1996 |
| WO | WO 97/06849 | 2/1997 |
| WO | WO 97/15227 | 5/1997 |
| WO | WO 97/24981 | 7/1997 |
| WO | WO 97/24983 | 7/1997 |
| WO | WO 97/25098 | 7/1997 |
| WO | WO 97/25101 | 7/1997 |
| WO | WO 97/26042 | 7/1997 |
| WO | WO 97/27900 | 8/1997 |
| WO | WO 97/29679 | 8/1997 |
| WO | WO 97/29682 | 8/1997 |
| WO | WO 97/29684 | 8/1997 |
| WO | WO 97/29700 | 8/1997 |
| WO | WO 97/29701 | 8/1997 |
| WO | WO 97/29709 | 8/1997 |
| WO | WO 98/10828 | 3/1998 |
| WO | WO 98/10829 | 3/1998 |
| WO | WO 98/10830 | 3/1998 |
| WO | WO 98/10831 | 3/1998 |
| WO | WO 98/10832 | 3/1998 |
| WO | WO 98/11840 | 3/1998 |
| WO | WO 98/15317 | 4/1998 |
| WO | WO 98/19719 | 5/1998 |
| WO | WO 98/56378 | 12/1998 |
| WO | WO 98/57701 | 12/1998 |
| WO | WO 99/03533 | 1/1999 |
| WO | WO 99/06105 | 2/1999 |
| WO | WO 99/09971 | 3/1999 |
| WO | WO 99/24110 | 5/1999 |
| WO | WO 99/29307 | 6/1999 |
| WO | WO 99/55360 | 11/1999 |
| WO | WO 99/59548 | 11/1999 |
| WO | WO 00/01443 | 1/2000 |
| WO | WO 00/04947 | 2/2000 |
| WO | WO 00/12525 | 3/2000 |
| WO | WO 00/16741 | 3/2000 |
| WO | WO 00/27475 | 5/2000 |
| WO | WO 00/42914 | 7/2000 |
| WO | WO 00/53257 | 9/2000 |
| WO | WO 00/74773 | 12/2000 |
| WO | WO 01/10375 | 2/2001 |
| WO | WO 01/24871 | 4/2001 |
| WO | WO 01/49367 | 7/2001 |
| WO | WO 01/52931 | 7/2001 |
| WO | WO 01/66183 | 9/2001 |
| WO | WO 01/91854 | 12/2001 |
| WO | WO 01/93950 | 12/2001 |
| WO | WO 01/93951 | 12/2001 |
| WO | WO 02/10791 | 2/2002 |
| WO | WO 02/053093 | 7/2002 |
| WO | WO 02/082968 | 10/2002 |
| WO | WO 03/045493 | 6/2003 |
| WO | WO 2004/021858 | 3/2004 |
| WO | WO 2004/059393 | 7/2004 |
| WO | WO 2004/070396 | 8/2004 |
| WO | WO 2004/080533 | 9/2004 |
| WO | WO 2004/112563 | 12/2004 |
| WO | WO 2004/112883 | 12/2004 |
| WO | WO 2005/007232 | 1/2005 |
| WO | WO 2005/023081 | 3/2005 |
| WO | WO 2005/087310 | 9/2005 |
| WO | WO 2005/114369 | 12/2005 |
| WO | WO 2006/018851 | 2/2006 |
| WO | WO 2006/073671 | 7/2006 |
| WO | WO 2006/087712 | 8/2006 |
| WO | WO 2006/087717 | 8/2006 |
| WO | WO 2006/097934 | 9/2006 |
| WO | WO 2006/097935 | 9/2006 |
| WO | WO 2006/102626 | 9/2006 |
| WO | WO 2006/119467 | 9/2006 |
| WO | WO 2006/129321 | 9/2006 |
| WO | WO 2007/080595 | 7/2007 |
| WO | WO 2007/091255 | 8/2007 |
| WO | WO 2008/117296 | 10/2008 |
| WO | WO 2008/139463 | 11/2008 |
| WO | WO 2011/092710 | 8/2011 |

OTHER PUBLICATIONS

Official Action Dated May 5, 2010 From the US Patent and Trademark Office Re.: U.S. Appl. No. 11/884,389.
Official Action Dated May 26, 2010 From the US Patent and Trademark Office Re.: U.S. Appl. No. 11/318,845.
Official Action Dated Apr. 30, 2010 From the US Patent and Trademark Office Re.: U.S. Appl. No. 11/932,149.
Official Action Dated May 12, 2011 From the US Patent and Trademark Office Re.: U.S. Appl. No. 10/039,845.
Official Action Dated Jun. 13, 2011 From the US Patent and Trademark Office Re. U.S. Appl. No. 11/933,168.
Official Action Dated May 21, 2010 From the US Patent and Trademark Office Re. U.S. Appl. No. 10/116,201.
Official Action of Nov. 3, 2009 From the US Patent and Trademark Office Re.: U.S. Appl. No. 11/931,724.
Official Action of Apr. 30, 2010 From the US Patent and Trademark Office Re.: U.S. Appl. No. 11/931,724.
Response Dated May 3, 2010 to Official Action of Dec. 3, 2009 From the US Patent and Trademark Office Re.: U.S. Appl. No. 11/318,845.
Official Action Dated Jun. 17, 2010 From the US Patent and Trademark Office Re.: U.S. Appl. No. 10/549,216.
Response Dated Jul. 1, 2010 to Invitation Pursuant to Rule 62a(1) EPC and Rule 63(1) EPC of May 5, 2010 From the European Patent Office Re.: U.S. Appl. No. 04719312.3.
Response in Conjunction With an RCE Dated Jul. 18, 2010 to Official Action Dated Feb. 4, 2010 From the US Patent and Trademark Office Re.: U.S. Appl. No. 10/039,845.
Response in Conjunction With an RCE Dated Jul. 21, 2010 to Official Action of Feb. 4, 2010 From the US Patent and Trademark Office Re.: U.S. Appl. No. 10/039,845.
Supplemental Response Dated Mar. 28, 2010 After an Interview of Mar. 4, 2010 From the US Patent and Trademark Office Re. U.S. Appl. No. 10/237,263.

Antman et al. "Treatment of 150 Cases of Life-Threatening Digitalis Intoxication With Digoxin-Specific Fab Antibody Fragments", Circulation, 81(6): 1744-1752, 1990.

Antoni et al. "Polarization Effects of Sinusoidal 50-Cycle Alternating Current on Membrane Potential of Mammalian Cardiac Fibres", Pflügers Archiv European Journal of Physiology, 314(4): 274-291, 1970. Abstract.

Bakker et al. "Beneficial Effects of Biventricular Pacing of Congestive Heart Failure", Pace, 17(Part II): 318, 1994.

Bargheer et al. "Prolongation of Monophasic Action Potential Duration and the Refractory Period in the Human Heart by Tedisamil, A New Potassium-Blocking Agent", Journal European Heart, 15(10): 1409-1414, 1994, Abstract.

Bers "Excitation Contraction Couplïng and Cardiac Contractile Force", Internal Medicine, 237(2): 17, 1991, Abstract.

Borst et al. "Coronary Artery Bypass Gratting Without Cardiopulmonary Bypass and Without Interuption of Native Coronary Flow Using a Novel Anastomosis Site Restraining Device (Octupus)", Journal of the American College of Cardiology, 27(6): 1356-1364, 1996.

Cano et al. "Dose-Dependent Reversal of Dixogin-Inhibited Activity of an In-Vitro Na+K+ATPase Model by Digoxin-Specific Antibody", Toxicology Letters, 85(2): 107-1011, 1996.

Cazeau et al. "Multisite Pacing for End-Stage Heart Failure: Early Experience", Pacing and Clinical Electrophysiology, 19(11): 1748-1757, 1996, Abstract.

Cheng et al. "Calcium Sparks: Elementary Events Underlying Excitation-Contraction Coupling in Heart Muscle", Science, 262(5134): 740-744, 1993, Abstract.

Cooper "Postextrasystolic Potention. Do We Really Know What It Means and How to Use It?", Circulation, 88: 2962-2971, 1993.

Coulton et al. "Magnetic Fields and Intracellular Calcium; Effects on Lymphocytes Exposed to Conditions for 'Cyclotron Resonance'", Phys. Med. Biol., 38: 347-360, 1993, Abstract.

Dillion "Optial Recordings in the Rabbit Heart Show That Defibrillation Strength Shocks Prolong the Duration of Depolarization and the Refractory Period", Circulation Research, 69: 842-856, 1991.

Dillon "Synchronized Repolarization After Defibrillation Shocks. A Possible Component of the Defibrillation Process Demonstration by Optical Recordings in Rabbit Heart", Circulation, 85(5): 1865-1878, 1992.

Fain et al. "Improved Internal Defibrillation Efficacy With a Biphasic Waveform", American Heart Journal, 117(2): 358-364, 1989, Abstract.

Fleg et al. "Impact of Age on the Cardiovasvular Response to Dynamic Upright Exercise in Healthy Men and Women", Journal of Applied Physiologyl, 78: 890-900, 1995, Abstract.

Fleischhauer et al. "Electrical Resistances of Interstitial and Microvascular Space as Determinants of the Extracellular Electrical Field and Velocity of Propagation in Ventricular Myocardium", Circulation, 92: 587-594, 1995.

Foster et al. "Acute Hemodynamic Effects of Atrio—Biventricular Padng in Humans", The Society of Thoracic Surgeons, 59: 294-300, 1995, Abstract.

Franz "Bridging the Gap Between Basic Clinical Electrophysiology: What Can Be Learned From Monophasic Action Potential Recordings?", Journal Cardiovasc Electrophysiology, 5(8): 699-710, 1994, Abstract.

Franz "Method and Theory of Monophasic Action Potential Recording", Prog. Cardiovasc Dis, 33(6): 347-368, 1991.

Fromer et al. "Ultrarapid Subthreshold Stimulation for Termination of Atriventricular Node Reentrant Tachycardia", Journal of the American College Cardiology, 20: 879-883, 1992.

Fu et al. "System Identification of Electrically Coupled Smooth Music Cells: The Passive Electrically Coupled Smooth Muscle Cells: The Passive Electrical Properties", IEEE Transactions on Biomedical Engineering, 38(11): 1130-1140, 1991.

Gill et al. "Refractory Period Extension During Ventricular Pacing at Fibrillatory Pacing Rates", Pacing and Clinical Elctrophysiology, 20(3): 647-653, 1997, Abstract.

Ham et al. "Classification of Cardiac Arrhythmias Using Fuzzy Artmap", IEEE Transactions on Biomedical Engineering, 43(4): 425-429, 1996, Abstract.

Hoffman et al. "Effects of Postextrasystolic Potentiation on Normal and Failing Hearts", Bulletin of the New York Academy of Medicine, 41(5): 498-534, 1965.

Josephson "Clinical Cardiac Electrophysiology: Techniques and Interpertations", Lea & Febiger, 2nd Ed., 2 P., 1991.

King et al. "The Inotropic Action of Paired Pulse Stimulation in the Normal and Failing Heart: An Experimental Study", Cardiovascular Research, 2: 122-129, 1968.

Knisley et al. "Prolgongation and Shortening of Action Potentials by Electrical Shocks in Frog Ventricular Muscle", American Journal of Physiology, 266(6): H2348-H2358, 1994, Abstract.

Koller et al. "Relation Between Repolarization and Refractoriness During Programmed Electrical Stimulation in the Human Right Ventricle", Circulation, 91(9): 2378-2384, 1995, Abstract.

Langberg et al. "Identification of Ventricular Tachycardia with Use of the Morphology of the Endocardial Electrogram", Circulation, 77(6): 1363-1369, 1988.

Lindstrom et al. "Intracellular Calcium Oscillations in a T-Cell Line After Exposure to Extremely-Low-Frequency Magnetic Fields with Variable Frequencies and Flux Densities", Bioelectromagnetics, 16(1): 41-47, 1995, Abstract.

Matheny et al. "Vagus Nerve Stimulation as a Method to Temporarily Slow or Arrest the Heart", Annals of Thoracic Surgery, 63(6): S28-29, 1997, Abstract.

McVeigh et al. "Noninvasive Measurement of Transmural Gradients in Myocardial Strain With MR Imaging", Radiology, 180(3): 677, 679-684, 1991.

Mercando et al. "Automated Detection of Tachycardias by Antitachycardia Devices", Cardiac Electrophysiology: From Cell to Bedside, Chap.100: 943-948, 2004.

Moran et al. "Digoxin-Specific Fab Fragments Impair Renal Function in the Rat", Journal of Pharmacy and Pharmacology, 46(10): 854-856, 1994, Abstract.

Morse et al. "A Guide to Cardiac Pacemakers, Defibrillators and Related Products".

Nannini et al. "Muscle Recruitment With Intrafascicular Electrodes", IEEE Transactions on Biomedical Engineering, 38: 769-776, 1-991, Abstract.

Paul et al. "Automatic Recognition of Ventricular Arrhythmias Using Temporal Electrogram Analysis", PACE, 14: 1265-1273, 1991.

Pumir et al. "Control of Rotating Waves in Cardiac Muscle: Analysis of the Effect of Electric Fields", Proceedings: Biological Sciences, 257(1349): 129-134, 1994, Abstract.

Ranjan et al. "Electrical Stimulation of Cardiac Myocytes", Annals of Biomedical Engineering, 23(6): 812-821, 1995, Abstract.

Saksena et al. "Prevention of Recurrent Atrial Fibrillation With Chronic Dual-Site Right Atrial Pacing", Journal of the American College of Cardiology, 28(3): 687-694, 1996, Abstract.

Schwartz et al. "Exposure of Frog Hearts to CW or Amplitude-Modified VHF Fields: Selective Efflux of Calcium Ions at 16 Hz", Bioelectromagnetics, 11(4): 349-358, 1990, Abstract.

Shumaik et al. "Oleander Poisoning: Treatment With Digoxin-Specific Fab Antibody Fragments", Annals of Emergency Medicine, 17(7): 732-735, 1988.

Skale et al. "Inhibition of Premature Ventricular Extrastimuli by Subthreshold Conditioning Stimuli", J. Am. Coll. Cardiol., 6: 133-140, 1985, Abstract.

Sweeny et al. "Countershock Strength-Duration Relationship for Myocardial Refractory Period Extension", Academic Emergency Medicine, 2(1): 57-62, 1995, Abstract.

Sweeny et al. "Refractory Interval After Transcardiac Shocks During Ventricular Fibrillation", Circulation, 94(11): 2947-2952, 1996.

Sweeny et al. "Ventricular Refractory Period Extension Caused by Defibrillation Shocks", Circulation, 82(3): 965-972, 1990.

Talit et al. "The Effect of External Cardiac Pacing on Stroke Volume", pace, 13(5): 598-602, 1990, Abstract.

Taniguchi et al. "Inhomogeneity of Cellular Activation Time and Vmax in Normal Myocardial Tissue Under Electrical Field Stimulation", Am. J. Physiol., 267: H694-H705, 1994, Abstract.

Thakor et al. "Effect of Varying Pacing Waveform Shapes on Propagation and Hemodynamics in the Rabbit Heart", The Americal Journal of Cardiology, 79(6A): 36-43, 1997, Abstract.

Tsong "Electroporation of Cell Membranes", Biophysical Journal, 60: 297-306, 1991.

Verrier et al. "Electrophysiologic Basis for T Wave Alternans as an Index of Vulnerability to Ventricular Fibrillation", Journal of Cardiovascular Electrophysiology, 5(5): 445-461, 1994. Abstract.

Webster Design of Cardiac Pacemakers, IEEE Press, p. xi-xiii, 1995.

Wessale et al. "Stroke Volume and the Three Phase Cardiac Output Rate Relationship With Ventricular Pacing", PACE, 13: 673-680, 1990.

Windle et al. "Subthreshold Conditioning Stimuli Prolong Human Ventricular Refractoriness", Am. J. Cardiol., 57(6): 381-386, 1986, Abstract.

Wirtzfeld et al. "Physiological Pacing: Present Status and Future Developments", Pace, 10(Part I): 41-57, 1987. Abstract.

Xue et al. "Neural-Network-Based Adaptive Matched Filtering for QRS Detection", IEEE Transactions on Biomedical Engineering, 39(4): 317-329, 1992, Abstract.

Zipes et al. "Cardiac Electrophysiology—From Cell to Bedside", Saunders Co., 4th Ed., 1990.

Official Action Dated Jul. 21, 2010 From the US Patent and Trademark Office Re.: U.S. Appl. No. 11/802,685.

Response Dated Aug. 10, 2011 to Official Action of May 13, 2011 From the US Patent and Trademark Office Re. U.S. Appl. No. 11/933,168.

Response Dated Jul. 27, 2011 to Official Action of Apr. 28, 2011 From the US Patent and Trademark Office Re. U.S. Appl. No. 11/931,889.

Translation of Office Action Dated Aug. 3, 2011 From the State Intellectual Property Office (SIPO) of the People's Republic of China Re.: Application No. 200480012687.5.

Adeghate et al. "Effect of Electrical Field Stimulation on Insulin and Glucagon Secretion From the Pancreas of Normal and Diabetic Rats", Hormonal Metabolism Research, 33: 281-289, 2001.

Antman et al. "Treatment of 150 Cases of Life-Threatening Digitalis Intoxication With Digoxin-Specific Fab Antibody Fragments. Final Report of a Multicenter Study", Circulation, 81(6): 1744-1752, 1990.

Antoni et al. "Polarization Effects of Sinusoidal 50-Cycle Alternating Current on Membrane Potential of Mammalian Cardia Fibers", Pflügers Archiv, European Journal of Physiology, 314(4): 274-291, 1970. Abstract.

Bergsten et al. "Synchronous Oscillations of Cytoplasmic Ca2+ and Insulin Release in Glucose-Stimulated Pancreatic Islets", The Journal of Biological Chemistry, 269(12): 8749-8753, 1994.

Cano et al. "Dose-Dependent Reversal of Digoxin-Inhibited Activity of an In-Vitro Na+K+ATPase Model by Digoxin-Specific Antibody", Toxicology Letters, 85(2): 107-111, 1996. Abstract.

Crider et al. "2-Pyridylthioureas: Novel Nonpeptide Somatostatin Agonists With SST4 Selectivity", Current Pharmaceutical Design, 5(4): 255-263, 1999.

Davis et al. "Insulin, Oral Hypoglycemic Agents, and the Pharmacology of the Endocrine Pancreas", The Pharmacological Basis of Therapeutics, Chap.60: 1487-1499, 1507-1510.

Devedeux et al. "Uterine Electromyography: A Critical Review", American Journal of Obstetrics & Gynecology, 169(6): 1636-1653, 1993. Abstract.

Gold et al. "Evidence That Glucose 'Marks' B Cells Resulting in Preferential Release of Newly Synthesized Insulin", Science, 218(4567): 56-58, 1982. Abstract.

Gomis et al. "Oscillatory Patterns of Electrical Activity in Mouse Pancreatic Islets of Langerhans Recorded In Vivo", European Journal of Physiology, 432(3): 510-515, 1996.

Gussoni et al. "Dystrophin Expression in the MDX Mouse Restored by Stem Cell Transplantation", Nature, 401(6751): 390-394, 1999. Abstract.

Hinke et al. "Dipeptidyl Peptidase IV (DPIV/CD26) Degradation of Glucagon Characterization of Glucagon Degradation Products and DPIV-Resistant Analogs", The Journal of Biological Chemistry, 275(6): 3827-3834, 2000.

Hoist et al. "Nervous Control of Pancreatic Endocrine Secretion in Pigs. I. Insulin and Glucagon Responses to Electrical Stimulation of the Vagus Nerves", Acta Physiologica Scandinavica, 111(1): 1-7, 1981. Abstract. p. 5, r-h Col., Last Line—p. 6, 1-h Col., First Line.

Jaremko et al. "Advances Toward the Implantable Artificial Pancreas for Treatment of Diabetes", Diabetes Care, 21(3): 444-450, 1998.

Kurose et al. "Glucagon, Insulin and Somatostatin Secretion in Response to Sympathetic Neural Activation in Streptozotocin-Induced Diabetic Rats. A Study With the Isolated Perfused Rat Pancreas In Vitro", Diabetologia, 35: 1035-1041, 1992. Abstract.

Luiken et al. "Contraction-Induced Fatty Acid Translocase/CD36 Translocation in Rat Cardiac Myocytes Is Mediated Through AMP-Activated Protein Kinase Signaling", Diabetes, 52: 1627-1634, 2003.

Magnus et al. "Model of Beta-Cell Mitochondrial Calcium Handling and Electrical Activity. II. Mitochondrial Variables", American Journal of Physiology, Cell Physiology, 274(43): C1174-C1184, 1998.

Meurer et al. "Properties of Native and In Vitro Glycosylated Forms of the Glucogan-Like Peptide-1 Receptor Antagonist Exendin(9-39)", Metabolism, 48(6): 716-724, 1999.

Misler et al. "Electrophysiology of Stimulus-Secretion Coupling in Human B-Cells", Diabetes, 41(10): 1221-1228, 1992. Abstract.

Moran et al. "Digoxin-Specific Fab Fragments Impair Renal Function in the Rat", Journal of Pharmacy and Pharmacology, 46(10): 854-856, 1994. Abstract.

Nadal et al. "Homologous and Heterologous Asynchronicity Between Identified Alpha-, Beta- and Gamma-Cells Within Intadct Islets of Langerhans in the Mouse", Journal of Physiology, 517(Pt 1): 85-93, 1999.

Ohinata et al. "Proadrenomedullin N-Terminal 20 peptide (PAMP) elevates Blood Glucose Levels Via Bombesin Receptor in Mice", FEBS Letters, 473(2): 207-211, 2000.

Palti et al. "Islets of Langerhans Generate Wavelike Electric Activity Modulated by Glucose Concentration", Diabetes, 45: 595-601, 1996. Abstract.

Park et al. "Significant Cholinergic Role in Secreted-Stimulated Exocrine Secretion in Isolated Rat Pancreas", American Journal of Physiology, 274(2 Pt 1): G413-G418, 1998. Abstract.

Patterson et al. "Therapeutic Angiogenesis.The New Electrophysiology?", Circulation, 99: 2614-2616, 1999.

Pokrovsky et al. "Physiology of Man", Moscow Medicine, 1: 82-83, 94, 2: 42, 54, Translation of Extracts. Translation English!.

Porksen et al. "Section 6: Pulsatile and Phasic Insulin Release in Normal and Diabetic Man. Pulsatile Insulin Secretion: Detection, Regulation, and Role in Diabetes", Diabetes, 51(Suppl.1): S245-S254, 2002.

Rivera et al. "Regualtion of Protein Secretion Through Controlled Aggregation in the Endoplasmic Reticulum", Science, 287: 826-830, 2000.

Schirra et al. "Exendin(9-39)Amide Is an Antagonist of Glucagon-Like Peptide-1(7-36)Amide in Humans", Journal of Clinical Investigation, 101(7): 1421-1430, 1996.

Serre et al. "Exendin-(9-39) Is an Inverse Agonist of the Murine Glucagon-Like Peptide-1 Receptor: Implications for Basal Intracellular Cyclic Adenosine 3',5'-Monophosphate Levels and B-Cells Glucose Competence", Endocrinology, 139(1 1): 4448-4454, 1998.

Shah et al. "Impact of Lack of Suppression of Glucagon on Glucose Tolerance in Humans", American Journal of Physiology, 277(2 Pt 1): E283-E290, 1999.

Shmit et al. "Physiology of Man", Moscow Medicine, 1: 78, Translation of Extracts, 1996. Translation in English.

Shuba et al. "Physiology of Vessel Smooth Muscles", Naukova Dumka, p. 11-15, 142, Translation of Extracts, 1988. Translation in English!.

Singh et al. "Effect of Islet Hormones on Nerve-Mediated and Acetylcholine- Evoked Secretory Responses in the Isolated Pancreas of Normal and Diabetic Rats", International Journal of Molecular Medicine, 1(3): 627-634, 1998. Abstract. Abstract, p. 633, Section 'Discussion'.

Soria et al. "Cytosolic Calcium Oscillations and Insulin Release in Pancreatic Islets of Langerhans", Diabetes & Metabolism, 24(1): 37-40, 1998.

Sukhorukov et al. "The Effect of Electrical Deformation Forces on the Electropermeabilization of Erythrocyte Membranes in Low- and High-Conductivity Media", The Journal of Membrane Biology, 163(3): 235-245, 1998. Abstract.

Valdeolmillos et al. "In Vivo Synchronous Membrane Potential Oscillations in Mouse Pancreatic Beta-Cells: Lack of Co-Ordination Between Islets", Journal of Physiology, 493(1): 9-18, 1996.
Van Ripper et al. "Electrical Field Stimulation—Mediated Relaxation of a Rabbit Middle Cerebral Artery", Circulation Research, 70: 1104-1112, 1992.
Wang et al. "Islet Amyloid Polypeptide Tonally Inhibits Beta-, Alpha-, and Gamma-Cell Secretion in Isolated Rat Pancreatic Islets", American Journal of Physiology, 276(1 Pt 1): E19-E24, 1999.
West "The Endocrine Pancreas", Best and Taylor's Physiological Basis of Medical Practice, 12th Ed.(Chap.50): 754-769.
Wright et al. Structure of Fab hGR-2F6, A Competitive Antagonist of the Glucagon Receptor, Acta Crystallographica, Section D Biological Crystallography, 56(Pt 1): 573-580, 2000.
Yonemura et al. "Amelioration of Diabetes Mellitus in Partially Depancreatized Rats by Poly(ADP-Ribose) Synthetase Inhibitors. Evidence of Islet B-Cell Regeneration", Diabetes, 33(4): 401-404, 1984.
Zhou et al. "Prevention of Action Potentials During Extracellular Electrical Stimulation of Long Duration", Journal of Cardiovascular Electrophysiology, 8: 779-789, 1997. Abstract.
Response Dated Aug. 26, 2010 to Official Action of May 26, 2010 From the US Patent and Trademark Office Re.: U.S. Appl. No. 11/318,845.
Official Action Dated Sep. 27, 2010 From the US Patent and Trademark Office Re.: U.S. Appl. No. 10/804,560.
Response Dated Oct. 13, 2010 to Official Action of Apr. 30, 2010 From the US Patent and Trademark Office Re.: U.S. Appl. No. 11/932,149.
Official Action Dated Oct. 5, 2010 From the US Patent and Trademark Office Re.: U.S. Appl. No. 10/039,845.
Response Dated Sep. 30, 2010 to Official Action of Apr. 30, 2010 From the US Patent and Trademark Office Re.: U.S. Appl. No. 11/931,724.
Rsponse Dated Oct. 5, 2010 to Official Action of May 5, 2010 From the US Patent and Trademark Office Re.: U.S. Appl. No. 11/884,389.
San Mauro et al. "Nerves of the Heart: A Comprehensive Review With a Clinical Point of View", Neuroanatomy, 8: 28-31, 2009.
International Search Report and the Written Opinion Dated Sep. 29, 2006 From the International Searching Authority Re.: Application No. PCT/IL06/00204.
International Search Report Dated Sep. 13, 2004 From the International Searching Authority Re.: Application No. PCT/IL03/00736.
Notice of Allowance Dated Sep. 7, 2006 From the US Patent and Trademark Office Re.: U.S. Appl. No. 10/804,560.
Official Action Dated Nov. 3, 2009 From the US Patent and Trademark Office Re.: U.S. Appl. No. 11/931,724.
Official Action Dated Sep. 3, 2009 From the US Patent and Trademark Office Re.: U.S. Appl. No. 10/804,560.
Official Action Dated Nov. 5, 2009 From the US Patent and Trademark Office Re.: U.S. Appl. No. 10/549,216.
Official Action Dated Jul. 9, 2007 From the US Patent and Trademark Office Re.: U.S. Appl. No. 10/237,263.
Official Action Dated Sep. 11, 2008 From the US Patent and Trademark Office Re.: U.S. Appl. No. 10/237,263.
Official Action Dated Sep. 12, 2008 From the US Patent and Trademark Office Re.: U.S. Appl. No. 10/039,845.
Official Action Dated Sep. 13, 2007 From the US Patent and Trademark Office Re.: U.S. Appl. No. 10/237,263.
Official Action Dated Jul. 14, 2008 From the US Patent and Trademark Office Re.: U.S. Appl. No. 10/526,708.
Official Action Dated Apr. 18, 2007 From the US Patent and Trademark Office Re.: U.S. Appl. No. 10/804,560.
Official Action Dated Jul. 18, 2007 From the US Patent and Trademark Office Re.: U.S. Appl. No. 10/039,845.
Official Action Dated Jul. 19, 2007 From the US Patent and Trademark Office Re.: U.S. Appl. No. 10/526,708.
Official Action Dated Jun. 19, 2008 From the US Patent and Trademark Office Re.: U.S. Appl. No. 10/237,263.
Official Action Dated Apr. 27, 2010 From the US Patent and Trademark Office Re.: U.S. Appl. No. 10/570,576.
Official Action Dated Mar. 27, 2008 From the US Patent and Trademark Office Re.: U.S. Appl. No. 10/804,560.

Official Action Dated Apr. 30, 2010 From the US Patent and Trademark Office Re.: U.S. Appl. No. 11/931,724.
Official Action Dated Mar. 31, 2010 From the US Patent and Trademark Office Re.: U.S. Appl. No. 10/237,263.
Supplementary Notice of Allowability Dated Nov. 22, 2006 From the US Patent and Trademark Office Re.: U.S. Appl. No. 10/804,560.
Adeghate et al. "Effect of Electrical Field Stimulation on Insulin and Glucagon Secretion From the Pancreas of Normal and Diabetic Rats", Hormone and Metabolic Research, 33(5): 281-289, May 2001. Abstract.
Bergsten et al. "Synchronous Oscillations of Cytoplasmic Ca2+ and Insulin Release in Glucose-Stimulated Pancreatic Islets", The Journal of Biological Chemistry, 269(12): 8749-8753, Mar. 25, 1994.
Blank et al. "Initial Interactions in Electromagnetic Field-Induced Biosynthesis", Journal of Cellular Physiology, 199: 359-363, 2004.
Bouaziz et al. "Direct Electrical Stimulation of Insulin Secretion by Intact Murine Islets of Langerhans Through the Culture Support", Electromagnetic Biology and Medicine, 17(2): 171-184, 1998. Abstract.
Bronzino "Biomedical Engineering Handbook", IEEE Press/CRC Press, Chap. 82.5: 1288, 1995.
Devedeux et al. "Uterine Electromyography: A Critical Review", American Journal of Obstetric Gynecology, 169(6): 1636-1653, 1993.
Franz "Method and Theory of Monophasic Action Potential Recording", Progress in Cardiovascular Diseases, 33(6): 347-368, 1991. Abstract.
Gold et al. "Evidence That Glucose 'Marks' Beta Cells Resulting in Preferential Release of Newly Synthesized Insulin", Science, 218(4567): 56-58, Oct. 1, 1982. Abstract.
Gomis et al. "Oscillatory Patterns of Electrical Activity in Mouse PancreaticIslets of Langerhans Recorded in Vivo", PflÜgers Archiv European Journal of Physiology, 432(3): 510-515, 1996.
Highfill et al. "Large-Scale Production of Murine Bone Marrow Cells in an Airlift Packed Bed Bioreactor", Biotechnology and Bioengineering, 50(5): 514-520, 1996.
Hinke et al. "Dipeptidyl Peptidase IV (DPIV/CD26) Degradation of Glucagon. Characterization of Glucagon Degradation Products and DPIV-Resistant Analogs", The Journal of Biological Chemistry, 275(6): 3827-3834, Feb. 11, 2000.
Holst et al. "Nervous Control of Pancreatic Endocrine Secretion in Pigs. I. Insulin and Glucagon Responses to Electrical Stimulation of the Vagus Nerves", Acta Physiologica Scandinavica, 111(1): Jan. 1-7, 1981. Abstract.
Homer et al. "Electrode for Recording Direction of Activation, Conduction Velocity and Monophasic Action Potential of Myocardium", American Journal of Physiology, 272(4): H1917-H1927, 1997. Abstract.
Jaremko et al. "Advances Towards the Implantable Artifical Pancreas for Treatment of Diabetes", Diabetes Care, 21(3): 444-450, 1998.
Knisley et al. "Effect of Field Stimulation on Cellular Repolarization in Rabbit Myocardium. Implications for Reentry Induction", Circulation Research, 70(4): 707-715, Apr. 1992.
Knisley et al. "Prolongation and Shortening of Action Potentials by Electrical Shocks in Frog Ventricular Muscle", American Journal of Physiology, 266(6): H2348-H2358, 1994, Abstract.
Kurose et al. "Glucagon, Insulin and Somatostatin Secretion in Response to Sympathetic Neural Activation in Streptozotocin-Induced Diabetic Rats. A Study With the Isolated Perfused Rat Pancreas In Vitro", Diabetologia, 35(11): 1035-1041, Nov. 1992. Abstract.
Lindström et al. "Intracellular Calcium Oscillations in a T-Cell Line After Exposure to Extremely-Low-Frequency Magnetic Fields with Variable Frequencies and Flux Densities", Bioelectromagnetics, 16(1): 41-47, 1995, Abstract.
Loginov et al. "Effects of an Impulse Electromagnetic Field on Calcium Ion Accumulation in the Sarcoplasmic . . . ", Kosm. Biol. Aviakosm. Med., 15: 51-53, 1991.
Lubart et al. "Effect of Light on Calcium Transport in Bull Sperm Cells", Journal of Photochemistry and Photobiology B, Biology, 15(4): 337-341, Sep. 15, 1992. Abstract.

Magnus et al. "Model of β-Cell Mitochondrial Calcium Handling and Electrical Activity. II. Mitochondrial Variables", American Journal of Physiology, Cell Physiology, 274(43): C1174-C1184, 1998.

Meurer et al. "Properties of Native and in Vitro Glycosylated Forms of the Glucogan-Like Peptide-1 Receptor Antagonist Exendin(9-39)", Metabolism: Clinical and Experimental, 48(6): 716-724, Jun. 1999. Abstract.

Misler et al. "Electrophysiology of Stimulus-Secretion Coupling in Human Beta-Cells", Diabetes, 41(10): 1221-1228, Oct. 1992. Abstract.

Nadal et al. "Homologous and Heterologous Asynchronicity Between Identified α-, 62- and δ-Cells Within Intact Islets of Langerhans in the Mouse", Journal of Physiology, 517(Pt.1): 85-93, 1999.

Ohinata et al. "Proadrenomedullin N-Terminal 20 Peptide (PAMP) Elevates Blood Glucose Levels Via Bombesin Receptor in Mice", FEBS Letters, 473(2): 207-211, May 2000. Abstract.

Palti et al. "Islets of Langerhans Generate Wavelike Electric Activity Modulated by Glucose Concentration", Diabetes, 45(5): 595-601, May 1996. Abstract.

Park et al. "Significant Cholinergic Role in Secretin-Stimulated Exocrine Secretion in Isolated Rat Pancreas", American Journal of Physiology, AJP—Gastrointestinal and Liver Physiology, 274(2): G413-G418, Feb. 1998.

Patterson et al. "Therapeutic Angiogenesis: The New Electrophysiology?", Circulation, 99(20): 2614-2616, 1999.

Pokrovsky et al. "Physiology of Man", 1: 82-83, 94, 2: 42, 54.

Pørksen et al. "Section 6: Pulsatile and Phasic Insulin Release in Normal and Diabetic Man. Pulsatile Insulin Secretion: Detection, Regulation, and Role in Diabetes", Diabetes, 51(Suppl.1): S245-S254, Feb. 2002.

Pumir et al. "Control of Rotating Waves in Cardiac Muscle: Analysis of the Effect of Electric Fields", Proceedings of the Royal Society B: Biological Sciences, 257(1349): 129-134, 1994. Abstract.

Rivera et al. "Regulation of Protein Secretion Through Controlled Aggregation in the Endoplasmic Reticulum", Science, 287(5454): 826-830, Feb. 4, 2000. Abstract.

Saveliev et al. "Guidebook on Clinical Endoscopy", Moscow Medicine, p. 21, 35, Extract, 1985.

Schirra et al. "Exendin(9-39) Amide Is an Antagonist of Glucagon-Like Peptide-1(7-36) Amide in Humans", Journal of Clinical Investigation, 101(7): 1421-1430, Apr. 1998.

Schirra et al. "Mechanisms of the Antidiabetic Action of Subcutaneous Glucagon-Like Peptide-1 (17-36) Amide in Non-Insulin Dependent Diabetes Mellitus", Journal of Endocrinology Ltd., 156(1): 177-186, Jan. 1998. Abstract.

Serre et al. "Exendin-(9-39) Is an Inverse Agonist of the Murine Glucagon-Like Peptide-1 Receptor: Implications for Basal Intracellular Cyclic Adenosine 3',5'-Monophosphate Levels and β-Cells Glucose Competence", Endocrinology, 139(11): 4448-4454, 1998.

Shah et al. "Impact of Lack of Suppression of Glucagon on Glucose Tolerance in Humans", American Journal of Physiology, AJP—Endocrinology and Metabolism, 277(2 Pt.1): E283-E290, 1999.

Shmit et al. "Physiology of Man", Moscow Medicine, Mir, 1: 78, 1996.

Shuba et al. "Physiology of Vessel Smooth Muscles", Kiev Naukova Dumka, 142: 11-15, 142, 1988.

Singh et al. "Effects of Islet Hormones on Nerve-Mediated and Acetylcholine-Evoked Secretory Responses in the Isolated Pancreas of Normal and Diabetic Rats", International Journal of Molecular Medicine, 1(3): 627-634, Mar. 1998. Abstract.

Skale et al. "Inhibition of Premature Ventricular Extrastimuli by Subthreshold Conditioning Stimuli", Journal of the American College of Cardiology, 6: 133-140, 1985. Abstract.

Solomonow et al. "Control of Muscle Contractile Force Through Indirect High-Frequency Stimulation", American Journal of Physical Medicine, 62(2): 71-82, Apr. 1983. Abstract.

Soria et al. "Cytosolic Calcium Oscillations and Insulin Release in Pancreatic Islets of Langerhans", Diabetes & Metabolism, 24: 37-40, 1998.

Stevenson et al. "Electrophysiologic Characteristics of Ventricular Tachycardia or Fibrillation in Relation to Age of Myocardial Infarction", The American Journal of Cardiology, 57(6): 387-391, Feb. 15, 1986. Abstract.

Sweeny et al. "Countershock Strength-Duration Relationship for Myocardial Refractory Period Extension", Academic Emergency Medicine, 2(1): 57-62, 1995, Abstract.

Todd et al. "Subcutaneous Glucagon-Like Peptide I Improves Postprandial Glycaemic Control Over a 3-Week Period in Patients With Early Type 2 Diabetes", Clinical Science, 95: 325-329, 1998.

Van Riper et al. "Electrical Field Stimulation-Mediated Relaxation of a Rabbit Middle Cerebral Artery. Evidence of a Cholinergic Endothelium-Dependent Component", Circulation Research, 70(6): 1104-1112, Jun. 1992.

Wang et al. "Islet Amyloid Polypeptide Tonally Inhibits β-, α-, and δ-Cell Secretion in Isolated Rat Pancreatic Islets", American Journal of Physiology, AJP—Endocrinology and Metabolism, 276(1 Pt.1): E19-E24, 1999.

Windle et al. "Subthreshold Conditioning Stimuli Prolong Human Ventricular Refractoriness", American Journal of Cardiology, 57(6): 381-386, 1986. Abstract.

Wright et al. "Structure of Fab hGR-2 F6, a Competitive Antagonist of the Glucagon Receptor", Acta Crystallographica, Section D, Biological Crystallography, 56(Pt.5): 573-580, May 2000. Abstract.

Yokoyama "The Phase of Supernormal Excitation in Relation to the Strength of Subthreshold Stimuli", Japanese Heart Journal, 17(3): 315-325, May 1976.

Yonemura et al. "Amelioration of Diabetes Mellitus in Partially Depancreatized Rats by Poly(ADP-Ribose) Synthetase Inhibitors. Evidence of Islet B-Cell Regeneration", Diabetes, 33(4): 401-404, Apr. 1984. Abstract.

Zhou et al. "Prevention of Action Potentials During Extracellular Electrical Stimulation of Long Duration", Journal of Cardiovascular & Electrophysiology, 8(7): 779-789, 1997. Abstract.

Office Action Dated Jul. 13, 2009 From the State Intellectual Property Office of the People's Republic of China Re.: Application No. 200480027083.3 and Its Translation Into English.

Official Action Dated Jun. 1, 2009 From the US Patent and Trademark Office Re.: U.S. Appl. No. 10/039,845.

Official Action Dated Dec. 2, 2009 From the US Patent and Trademark Office Re.: U.S. Appl. No. 11/932,149.

Official Action Dated Dec. 3, 2009 From the US Patent and Trademark Office Re.: U.S. Appl. No. 11/318,845.

Official Action Dated Dec. 4, 2009 From the US Patent and Trademark Office Re.: U.S. Appl. No. 11/884,389.

Official Action Dated Oct. 6, 2009 From the US Patent and Trademark Office Re.: U.S. Appl. No. 11/550,560.

Official Action Dated Oct. 8, 2009 From the US Patent and Trademark Office Re.: U.S. Appl. No. 10/116,201.

Official Action Dated Sep. 14, 2009 From the US Patent and Trademark Office Re.: U.S. Appl. No. 11/931,889.

Official Action Dated Aug. 18, 2009 From the US Patent and Trademark Office Re.: U.S. Appl. No. 10/570,576.

Official Action Dated Sep. 25, 2009 From the US Patent and Trademark Office Re.: U.S. Appl. No. 10/526,708.

Official Action Dated Aug. 28, 2009 From the US Patent and Trademark Office Re.: U.S. Appl. No. 11/802,685.

Official Action Dated Aug. 28, 2009 From the US Patent and Trademark Office Re.: U.S. Appl. No. 11/932,064.

Response Dated Nov. 22, 2009 to Official Action of Jun. 1, 2009 From the US Patent and Trademark Office Re.: U.S. Appl. No. 10/039,845.

Gardner "Natriuretic Peptides: Markers or Modulators of Cardiac Hypertrophy?", Trends in Endocrinology and Metabolism, 14(9): 411-416, Nov. 2003.

Notice of Allowance Dated Dec. 28, 2010 From the US Patent and Trademark Office Re.: U.S. Appl. No. 11/932,064.

Official Action Dated Jan. 13, 2011 From the US Patent and Trademark Office Re.: U.S. Appl. No. 11/931,889.

Official Action Dated Dec. 14, 2010 From the US Patent and Trademark Office Re.: U.S. Appl. No. 11/884,389.

Bakker et al. "Biventricular Pacing Improves Functional Capacity in Patients With End-Stage Congestive Heart Failure", Pace, 17(11/Part II/120): 825, 1995.
Bargheer et al. "Prolongation of Monophastic Action Potantial Duration and the Refractory Period in the Human Heart by Tedisamil, A New Potassium-Blocking Agent", The European Society of Cardiology, 15(10): 1409-1414, 1994.
Burfeind et al. "The Effects of Mechanical Cardiac Stabilization on Left Ventricular Performance", European Journal of Cardio-Thoracic Surgery,14: 285-289, 1998.
Cazeau et al. "Multisite Pacing for End-Stage Heart Failure: Early Experience", Pace, 19(Part II): 1748-1757, 1996.
Cheng et al. "Calcium Sparks: Elementary Events Underlying Excitation-Contraction Coupling in Heart Muscle", Science, 262: 740-744, 1993.
Cooper "Postextrasystolic Potentiation: Do We Really Know What It Means and How to Use It?", Circulation, 88(6): 2962-2971, 1993.
Coulton et al. "Magnetic Fields and Intracellular Calcium: Effects on Lymphocytes Exposed to Conditions for 'Cyclotron Resonance'", Physics in Medicine and Biology, 38: 347-360, 1993.
Dillion "Optial Recordings in the Rabbit Heart Show That Defibrillation Strenght Shocks Prolong the Duration of Depolarization and the Refractory Period", Circulation Research, 69: 842-856, 1991.
Erol-Yilmaz et al. "Reversed Remodelling of Dilated Left Sided Cardiomyopathy After Upgrading From VVIR to VVIR Biventricular Pacing", Europace, 4: 445-449, 2002.
Fain et al. "Improved Internal Defibrillation Efficacy With a Biphasic Waveform", American Heart Journal, 117(2): 358-364, 1989.
Fleg et al. "Impact of Age on the Cardiovasvular Response to Dynamic Upright Exercise in Healthy Men and Women", Journal of Applied Physiology, 78: 890-900, 1995.
Foster et al. "Acute Hemodynamic Effects of Atrio—Biventricular Padng in Humans", The Society of Thoracic Surgeons, 59: 294-300, 1995.
Franz "Bridging the Gap Between Basic Clinical Electrophysiology: What Can Be Learned From Monophasic Action Potential Recordings?", Journal of Cardiovascular Electrophysiology, 5(8): 699-710, 1994.
Franz "Method and Theory of Monophasic Action Potential Recording", Progresses In Cardiovascular Diseases, 33(6): 347-368, 1991.
Fromer et al. "Ultrarapid Subthreshold Stimulation for Termination of Atriventricular Node Reentrant Tachycardia", Journal of the American College of Cardiology, 20(4): 879-883, 1992.
Fu et al. "System Identification of Electrically Coupled Smooth Muscle Cells: The Passive Electrically Coupled Smooth Muscle Cells: The Passive Electrical Properties", IEEE Transactions on Biomedical Engineering, 38(11): 1130-1140, 1991.
Gill et al. "Refractory Period Extension During Ventricular Pacing at Fibrillatory Pacing Rates", PACE, 20(Part I): 647-653, 1997.
Gilmour Jr. et al. "Dynamics of Circus Movement Re-Entry Across Canine Purkinje Fibre-Muscle Junctions", The Journal of Physiology, 476(3): 473-485, 1994.
Gilmour Jr. et al. "Overdrive Suppression of Conduction at the Canine Purkinje-Muscle Junction", Circulation, 76(6): 1388-1396, 1987.
Homer et al. "Electrode for Recording Direction of Activation, Conduction Velocity, and Monophasic Action Potential of Myocardium", American Journal of Physiology, 272: H1917-H1927, 1997.
Kinsley et al. "Effect of Field Stimulation on Cellular Repolarization in Rabbit Myocardium Implications for Reentry Induction", Circulation Research, 70: 707-715, 1991.
Knisley et al. "Prolongation and Shortening of Action Potentials by Electrical Shocks in Frog Ventricular Muscle", American Journal of Physiology, 266: H2348-H2358, 1994.
Koller et al. "Relation Between Repolarization and Refractoriness During Programmed Electrical Stimulation in the Human Right Ventricle", Circulation, 91:2378-2384, 1995.
Langberg et al. "Identification of Ventricular Tachycardia With Use of the Morphology of the Endocardial Electrogram", Circulation, 77: 1363-1369, 1988.

Lindström et al. "Intracellular Calcium Oscillations in a T-Cell Line After Exposure to Extremely-Low-Frequency Magnetic Fields With Variable Frequencies and Flux Densities", Bioelectromagnetics, 16: 41-47, 1995.
Pumir et al. "Control of Rotating Waves in Cardiac Muscle: Analysis of the Effect of Electric Field", Proceedings of the Royal Society B: Biological Sciences, 257(1349): 129-134, 1994.
Saihara "Summation of Excitation With a Single Conditioning Stimulus in the Canine Heart", PACE, 13: 52-58, 1990.
Sakuma et al. "A Model Analysis of Aftereffects of High-Intensity DC Stimulation on Action Potential of Ventricular Muscle", IEEE Transactions on Biomedical Engineering, 45(2): 258-267, 1998.
Skate et al. "Inhibition of Premature Ventricular Extrastimuli by Subthreshold Conditioning Stimuli", Journal of the American College of Cardiology, 6(1): 133-140, 1985.
Sweeney et al. "Refractory Interval After Transcardiac Shocks During Ventricular Fibrillation", Circulation, 94: 2947-2952, 1996.
Sweeney et al. "Ventricular Refractory Period Extension Caused by Defibrillation Shocks", Circulation, 82: 965-972, 1990.
Sweeny et al. "Countershock Strength-Duration Relationship for Myocardial Refractory Period Extension", Academy of Emergency Medicine, 2: 57-62, 1995.
Swerdlow et al. "Cardiovascular Collapse Caused by Electrocardiographically Silent 60-Hz Intracardiac Leakage Current: Implications for Electrical Safety", Circulation, 99: 2559-2564, 1999.
Talit et al. "The Effect of External Cardiac Pacing on Stroke Volume", PACE, 13: 598-602, 1990.
Taniguchi et al. "Inhomogeneity of Cellular Activation Time and VMax in Normal Myocardial Tissue Under Electrical Field Stimulation", American Journal of Physiology, 267: H694-H705, 1994.
Thakor et al. "Effect of Varying Pacing Waveform Shapes on Propagation and Hemodynamics in the Rabbit Heart", American Journal of Cardiology, 79(6A): 36-43, 1997.
Wirtzfeld et al. "Physiological Pacing: Present Status and Future Developments", PACE, 10(Pt.I): 41-57, 1987.
Yokoyama "The Phase of Supernormal Excitation in Relation to the Strength of Subthreshold Stimuli", Japanese Heart Journal, 17(3): 315-325, 1975.
Office Action Dated Nov. 2, 2007 From the Patent Office of the People's Republic of China Re.: Application No. 2004800009336.9.
Official Action Dated Dec. 5, 2008 From the US Patent and Trademark Office Re.: U.S. Appl. No. 11/550,560.
Official Action Dated Dec. 8, 2008 From the US Patent and Trademark Office Re.: U.S. Appl. No. 10/804,560.
Official Action Dated Dec. 24, 2008 From the US Patent and Trademark Office Re.: U.S. Appl. No. 10/237,263.
Supplementary European Search Report and the European Search Opinion Dated Nov. 28, 2008 From the European Patent Office Re.: Application No. 006759102.4.
Response Dated Jun. 7, 2010 to Official Action of Jan. 6, 2010 From the US Patent and Trademark Office Re. U.S. Appl. No. 11/933,168.
Response Dated Jan. 24, 2011 to Supplementary Partial European Search Report of Nov. 4, 2010 From the European Patent Office Re. Application No. 04719312.3.
Examination Report Dated Nov. 30, 2010 From the Government of India, Patent Office Re. Application No. 212/MUMNP/2006.
Office Action Dated Apr. 13, 2010 From the State intellectual Property Office of the People's Republic of China Re. Application No. 200480027293.3 and Its Translation Into English.
Official Action Dated Dec. 15, 2010 From the US Patent and Trademark Office Re.: U.S. Appl. No. 10/804,560.
Response dated Oct. 12, 2010 to Official Action of Jun. 11, 2010 From the US Patent and Trademark Office Re.: U.S. Appl. No. 11/932,064.
Response Dated Dec. 13, 2010 to Official Action of Jun. 11, 2010 From the US Patent and Trademark Office Re.: U.S. Appl. No. 11/550,560.
Response Dated Dec. 13, 2010 to Official Action of Oct. 13, 2010 From the US Patent and Trademark Office Re.: U.S. Appl. No. 11/919,491.
Response Dated Nov. 22, 2010 to Official Action of Jul. 21, 2010 From the US Patent and Trademark Office Re.: U.S. Appl. No. 11/802,685.

Response Dated Oct. 28, 2010 to Official Action of Jun. 28, 2010 From the US Patent and Trademark Office Re.: U.S. Appl. No. 11/931,889.
Official Action Dated Jan. 6, 2010 From the US Patent and Trademark Office Re. U.S. Appl. No. 11/933,168.
Response Dated Apr. 10, 2011 to Official Action of Jan. 6, 2011 From the US Patent and Trademark Office Re.: U.S. Appl. No. 11/931,724.
USPTO Public Print Out of Interference File Content of Interference Dated Apr. 4, 2011 From the US Patent and Trademark Office Re. Interference No. 105,765.
USPTO Public Print Out of Interference File Content of Interference Dated Apr. 4, 2011 From the US Patent and Trademark Office Re. Interference No. 105,768.
U.S. Appl. No. 90/008,688, filed Jun. 15, 2007, Ben Haim.
U.S. Appl. No. 90/008,689, Ben Haim.
U.S. Appl. No. 90/008,707, field Jun. 7, 2007, Ben Haim.
U.S. Appl. No. 95/000,032, Ben Haim.
Amended Request for Ex Parte Reexamination of US Patent No. 6,317,631 Dated Aug. 20, 2007 From the US Patent and Trademark Office Re.: U.S. Appl. No. 90/008,689.
Communication Pursuant to Article 94(3) EPC Dated Mar. 2, 2009 From the European Patent Office Re.: Application No. 05853465.2.
Communication Pursuant to Article 94(3) EPC Dated Jan. 27, 2010 From the European Patent Office Re. Application No. 07110023.4.
Communication Pursuant to Article 94(3) EPC Dated Jan. 28, 2009 From the European Patent Office Re.: Application No. 03794043.4.
Communication Pursuant to Article 94(3) EPC Dated Jan. 29, 2009 From the European Patent Office Re.: Application No. 04106247.2.
Communication Pursuant to Article 96(2) EPC Dated Mar. 2, 2007 From the European Patent Office Re.: Application No. 97929478.2.
Communication to Pursuant to Article 94(3) EPC Dated Mar. 4, 2009 From the European Search Report Re.: Application No. 06759102.4.
Inter Partes Reexamination Communication of Patent US 6,330,476 Dated Sep. 4, 2007 From the US Patent and Trademark Office Re.: U.S. Appl. No. 95/000,032.
International Preliminary Report on Patentability Dated Dec. 1, 2004 From the International Preliminary Examining Authority Re.: Application No. PCT/IL03/00736.
International Preliminary Report on Patentability Dated Nov. 15, 2007 From the International Bureau of WIPO Re.: Application No. PCT/US2006/017281.
International Preliminary Report on Patentability Dated Jun. 21, 2007 From the International Bureau of WIPO Re.: Application No. Jun. 21, 2007.
International Preliminary Report on Patentability Dated Sep. 27, 2007 From the International Bureau of WIPO Re.: Application No. PCT/IL2006/000345.
International Preliminary Report on Patentability Dated Aug. 30, 2007 From the International Bureau of WIPO Re.: Application No. PCT/IL2006/000204.
International Search Report and the Written Opinion Dated May 12, 2006 From the International Searching Authority Re.: Application No. PCT/US05/44557.
International Search Report and the Written Opinion Dated Oct. 16, 2006 From the International Searching Authority Re.: Application No. PCT/US06/17281.
Notification of Reasons of Rejection Dated Sep. 29, 2008 From the Japanese Patent Office Re.: Application No. 2004-534013 and Its Translation Into English.
Office Action Dated Dec. 4, 2009 From the State Intellectual Property Office of the People's Republic of China Re.: Application No. 03824661.9 and Its Translation Into English.
Office Action Dated Nov. 7, 2008 From the State Intellectual Property Office of the People's Republic of China Re.: Application No. 03824661.9 and Its Translation Into English.
Office Action Dated Jan. 8, 2010 From the State Intellectual Property Office (SIPO) of the People's Republic of China Re.: Application No. 200480012687.5 and Its Translation Into English.
Office Action Dated May 8, 2009 From the State Intellectual Property Office of the People's Republic of China Re.: Application No. 03824661.9 and Its Translation Into English.
Office Action Dated Oct. 12, 2004 From the Israeli Patent Office Re.: Application No. 128955.
Office Action Dated Dec. 15, 2008 From the State Intellectual Property Office (SIPO) of the People's Republic of China Re.: Application No. 200480012687.5 and Its Translation Into English.
Official Action Dated Aug. 1, 2007 From the US Patent and Trademark Office Re.: U.S. Appl. No. 90/008,312.
Official Action Dated Oct. 1, 2009 From the US Patent and Trademark Office Re.: U.S. Appl. No. 10/237,263.
Official Action Dated Feb. 4, 2010 From the US Patent and Trademark Office Re.: U.S. Appl. No. 10/039,845.
Official Action Dated Jan. 5, 2010 From the US Patent and Trademark Office Re.: U.S. Appl. No. 11/802,685.
Official Action Dated Nov. 5, 2010 From the US Patent and Trademark Office Re.: U.S. Appl. No. 10/549,216.
Official Action Dated Mar. 6, 2009 From the US Patent and Trademark Office Re.: U.S. Appl. No. 11/931,889.
Official Action Dated Mar. 6, 2009 From the US Patent and Trademark Office Re.: U.S. Appl. No. 11/932,064.
Official Action Dated Aug. 8, 2007 From the US Patent and Trademark Office Re.: U.S. Appl. No. 10/804,560.
Official Action Dated Jul. 15, 2008 From the US Patent and Trademark Office Re.: U.S. Appl. No. 10/116,201.
Official Action Dated Jan. 21, 2009 From the US Patent and Trademark Office Re.: U.S. Appl. No. 10/570,576.
Official Action Dated Jun. 23, 2009 From the US Patent and Trademark Office Re.: U.S. Appl. No. 10/549,216.
Official Action Dated Feb. 24, 2009 From the US Patent and Trademark Office Re.: U.S. Appl. No. 11/318,845.
Official Action Dated Mar. 25, 2010 From the US Patent and Trademark Office Re.: U.S. Appl. No. 10/804,560.
Official Action Dated Jun. 26, 2008 From the US Patent and Trademark Office Re.: U.S. Appl. No. 11/536,794.
Official Action Dated Aug. 31, 2007 From the US Patent and Trademark Office Re.: U.S. Appl. No. 11/536,794.
Official Action Dated Jul. 31, 2008 From the US Patent and Trademark Office Re.: U.S. Appl. No. 11/318,845.
Request for Ex Parte Reexamination of Patent No. 6,363,279—IDS Submitted Dec. 31, 2007 From the US Patent and Trademark Office Re.: U.S. Appl. No. 90/008,688.
Request for Ex Parte Reexamination of Patent No. 6,363,279—Notice of Intent to Issue Reexamination Certificate Dated Mar. 18, 2009 From the US Patent and Trademark Office Re.: U.S. Appl. No. 90/008,688.
Request for Ex Parte Reexamination of Patent No. 6,363,279—Official Action Dated Jun. 20, 2008 From the US Patent and Trademark Office Re.: U.S. Appl. No. 90/008,688.
Request for Ex Parte Reexamination of Patent No. 6,363,279—Order Granting Request Dated Nov. 5, 2007 From the US Patent and Trademark Office Re.: U.S. Appl. No. 90/008,688.
Request for Ex Parte Reexamination of Patent No. 6,363,279 Dated Jun. 8, 2007 From the US Patent and Trademark Office Re.: U.S. Appl. No. 90/008,688.
Request for Ex Parte Reexamination of Patent No. 6,363,279, Response to Official Action Dated Jun. 20, 2008 Submitted Aug. 20, 2008 From the US Patent and Trademark Office Re.: U.S. Appl. No. 90/008,688.
Request for Ex Parte Reexamination of US Patent No. 6,236,887—IDS Submitted Oct. 17, 2007 From the US Patent and Trademark Office Re.: U.S. Appl. No. 90/008,707.
Request for Ex Parte Reexamination of US Patent No. 6,236,887—IDS Submitted Sep. 29, 2008 From the US Patent and Trademark Office Re.: U.S. Appl. No. 90/008,707.
Request for Ex Parte Reexamination of US Patent No. 6,236,887—Notice of Intent to Issue Ex Parte Examination Certificate Dated Mar. 19, 2009 From the US Patent and Trademark Office Re.: U.S. Appl. No. 90/008,707.
Request for Ex Parte Reexamination of US Patent No. 6,236,887—Official Action and IDS Considered Dated Jun. 20, 2008 From the US Patent and Trademark Office Re.: U.S. Appl. No. 90/008,707.
Request for Ex Parte Reexamination of US Patent No. 6,236,887—Official Action Granting Request for Ex Parte Examination Dated Aug. 17, 2007 From the US Patent and Trademark Office Re.: U.S. Appl. No. 90/008,707.

Request for Ex Parte Reexamination of US Patent No. 6,236,887 Dated Jun. 13, 2007 From the US Patent and Trademark Office Re.: U.S. Appl. No. 90/008,707.
Request for Ex Parte Reexamination of US Patent No. 6,298,268—Certificate of Reexamination Issued Mar. 7, 2006, U.S. Appl. No. 90/006,788.
Request for Ex Parte Reexamination of US Patent No. 6,298,268—IDS Considered Feb. 22, 2005, U.S. Appl. No. 90/006,788.
Request for Ex Parte Reexamination of US Patent No. 6,298,268—Notice of Intent to Issue Certificate of Reexamination Dated Mar. 29, 2005, U.S. Appl. No. 90/006,788.
Request for Ex Parte Reexamination of US Patent No. 6,298,268 Dated Oct. 10, 2003, U.S. Appl. No. 90/006,788.
Request for Ex Parte Reexamination of US Patent No. 6,298,268 Order Granting Request for Ex Parte Reexamination Dated Dec. 19, 2003, U.S. Appl. No. 90/006,788.
Request for Ex Parte Reexamination of US Patent No. 6,317,631—Amendment in Response to Official Action Dated Jun. 20, 2008, Filed Aug. 20, 2008 From the US Patent and Trademark Office Re.: U.S. Appl. No. 90/008,689.
Request for Ex Parte Reexamination of US Patent No. 6,317,631—IDS Dated Sep. 26, 2008 From the US Patent and Trademark Office Re.: U.S. Appl. No. 90/008,689.
Request for Ex Parte Reexamination of US Patent No. 6,317,631—IDS Dated Dec. 31, 2007 From the US Patent and Trademark Office Re.: U.S. Appl. No. 90/008,689.
Request for Ex Parte Reexamination of US Patent No. 6,317,631—Notice of Intent to Issue Certificate of Reexamination Dated Mar. 18, 2009 From the US Patent and Trademark Office Re.: U.S. Appl. No. 90/008,689.
Request for Ex Parte Reexamination of US Patent No. 6,317,631—Official Action Dated Jun. 20, 2008, U.S. Appl. No. 90/008,689.
Request for Ex Parte Reexamination of US Patent No. 6,317,631—Order Granting Reexamination Dated Nov. 5, 2007, U.S. Appl. No. 90/008,689.
Request for Ex Parte Reexamination of US Patent No. 6,317,631—IDS Dated Jun. 8, 2007, U.S. Appl. No. 90/008,689.
Request for Ex Parte Reexamination of US Patent No. 6,330,476—IDS Dated May 31, 2006.
Request for Ex Parte Reexamination of US Patent No. 6,330,476—Comments by 3rd Party Requestor, Response Thereto and Official Action Issued Jul. 16, 2008, U.S. Appl. No. 95/000,032.
Request for Ex Parte Reexamination of US Patent No. 6,330,476—Communication of Right to Appeal dated Jul. 16, 2008, U.S. Appl. No. 95/000,032.
Request for Ex Parte Reexamination of US Patent No. 6,330,476—IDS Filed May 4, 2007, U.S. Appl. No. 95/000,032.
Request for Ex Parte Reexamination of US Patent No. 6,330,476—Official Action by Uspto Issued Mar. 23, 2004, U.S. Appl. No. 95/000,032.
Request for Ex Parte Reexamination of US Patent No. 6,330,476—Order Granting Request for Reexamination Dated Mar. 23, 2004 From the US Patent and Trademark Office Re.: U.S. Appl. No. 95/000,032.
Request for Ex Parte Reexamination of US Patent No. 6,330,476 Dated Dec. 31, 2003 From the US Patent and Trademark Office Re.: U.S. Appl. No. 95/000,032.
Request for Ex Parte Reexamination of US Patent No. 6,463,324—Amendment in Response to Official Action Dated Aug. 1, 2007 Filed Oct. 1, 2007 From the US Patent and Trademark Office Re.: U.S. Appl. No. 90/008,312.
Request for Ex Parte Reexamination of US Patent No. 6,463,324—Certificate of Reexamination Dated Apr. 29, 2008 From the US Patent and Trademark Office Re.: U.S. Appl. No. 90/008,312.
Request for Ex Parte Reexamination of US Patent No. 6,463,324—Official Action—Notice of Intent to Reexamine Dated Jan. 24, 2008 From the US Patent and Trademark Office Re.: U.S. Appl. No. 90/008,312.
Request for Ex Parte Reexamination of US Patent No. 6,463,324—Official Action Dated Aug. 1, 2007 From the US Patent and Trademark Office Re.: U.S. Appl. No. 90/008,312.
Request for Ex Parte Reexamination of US Patent No. 6,463,324—Official Action, Interview Summary and References Considered Dated Nov. 6, 2007 From the US Patent and Trademark Office Re.: U.S. Appl. No. 90/008,312.
Request for Ex Parte Reexamination of US Patent No. 6,463,324 Dated Nov. 1, 2006 From the US Patent and Trademark Office Re.: U.S. Appl. No. 90/008,312.
Response Dated Mar. 1, 2010 to Official Action of Aug. 28, 2009 From the US Patent and Trademark Office Re.: U.S. Appl. No. 11/932,064.
Response Dated Oct. 1, 2007 to Official Action of Aug. 1, 2007 From the US Patent and Trademark Office Re.: U.S. Appl. No. 90/008,312.
Response Dated Sep. 1, 2004 to Communication Pursuant to Article 96(2) EPC of Mar. 2, 2004 From the European Patent Office Re.: U.S. Appl. No. 97929478.2.
Response Dated Feb. 2, 2010 to Official Action of Dec. 2, 2009 From the US Patent and Trademark Office Re.: U.S. Appl. No. 11/932,149.
Response Dated Apr. 3, 2008 to Official Action of Jan. 3, 2008 From the US Patent and Trademark Office Re.: U.S. Appl. No. 10/116,201.
Response Dated Mar. 3, 2010 to Official Action of Sep. 3, 2009 From the US Patent and Trademark Office Re.: U.S. Appl. No. 10/804,560.
Response Dated Feb. 4, 2010 to Official Action of Dec. 4, 2009 From the US Patent and Trademark Office Re.: U.S. Appl. No. 11/884,389.
Response Dated Mar. 4, 2010 to Official Action of Nov. 5, 2010 From the US Patent and Trademark Office Re.: U.S. Appl. No. 10/549,216.
Response Dated Oct. 4, 2007 to Official Action of Sep. 4, 2007 From the US Patent and Trademark Office Re.: U.S. Appl. No. 95/000,032.
Response Dated Apr. 6, 2010 to Official Action of Oct. 6, 2009 From the US Patent and Trademark Office Re.: U.S. Appl. No. 11/550,560.
Response Dated Feb. 7, 2010 to Official Action of Dec. 2, 2009 From the US Patent and Trademark Office Re.: U.S. Appl. No. 11/932,149.
Response Dated Feb. 7, 2010 to Official Action of Nov. 3, 2009 From the US Patent and Trademark Office Re.: U.S. Appl. No. 11/931,724.
Response Dated May 7, 2007 to Examination Report of Mar. 2, 2007 From the Government of India, Patent Office Re.: Application No. 533/CHENP/2005.
Response Dated Feb. 8, 2010 to Official Action Dated Oct. 1, 2009 From the US Patent and Trademark Office Re.: U.S. Appl. No. 10/237,263.
Response Dated Feb. 9, 2010 to Official Action of Oct. 8, 2009 From the US Patent and Trademark Office Re.: U.S. Appl. No. 10/116,201.
Response Dated Mar. 15, 2010 to Official Action of Sep. 14, 2009 From the US Patent and Trademark Office Re.: U.S. Appl. No. 11/931,889.
Response Dated Jan. 17, 2008 to Official Action of Jul. 18, 2007 From the US Patent and Trademark Office Re.: U.S. Appl. No. 10/039,845.
Response Dated Feb. 18, 2010 to Official Action of Aug. 18, 2009 From the US Patent and Trademark Office Re.: U.S. Appl. No. 10/570,576.
Response Dated Apr. 20, 2006 to Communication Pursuant of Article 96(2) EPC of Nov. 2, 2005 From the European Patent Office Re.: Application No. 97929478.2.
Response Dated Aug. 20, 2008 to Official Action of Jun. 20, 2008 From the US Patent and Trademark Office Re.: U.S. Appl. No. 90/008,689.
Response Dated May 21, 2008 to Office Action of Dec. 11, 2007 From the Japanese Patent Office Re.: Application No. 09-525055.
Response Dated Dec. 24, 2006 to Office Action of Jul. 18, 2006 From the Japanese Patent Office Re.: Application No. 10-513446.
Response Dated Dec. 25, 2006 to Notice of Reasons for Rejection of Jul. 18, 2006 From the Japanese Patent Office Re.: Application No. 09-529637.
Response Dated Jan. 25, 2007 to Examination Report of Jul. 7, 2006 From the Government of India, Patent Office Re.: Application No. 533/CHENP/2005.
Response Dated Mar. 25, 2010 to Official Action of Sep. 25, 2009 From the US Patent and Trademark Office Re.: U.S. Appl. No. 10/526,708.
Summons to Attend Oral Proceedings Pursuant to Rule 115(1) EPC Dated Dec. 22, 2008 From the European Patent Office Re.: Application No. 97929480.8.

Supplementary European Search Report and the European Search Opinion Dated Nov. 28, 2008 From the European Patent Office Re.: Application No. 05853465.2.
Translation of Decision of Rejection Dated Apr. 22, 2009 From the Japanese Patent Office Re.: Application No. 2004-534013.
Translation of Notice of Reasons for Rejection Dated Jul. 18, 2006 From the Japanese Patent Office Re.: Application No. 9-529637.
Translation of Office Action Dated Sep. 12, 2008 From the State Intellectual Property Office of the People's Republic of China Re.: Application No. 200480032636.9.
Official Action Dated Apr. 28, 2011 From the US Patent and Trademark Office Re. U.S. Appl. No. 11/931,889.
Translation of Notice of Reasons for Rejection Dated Apr. 27, 2010 From the Japanese Patent Office Re.: Application No. 2007-206282.
Translation of Notification of Reasons of Rejection Dated Apr. 12, 2010 From the Japanese Patent Office Re.: Application No. 2006-525265.
Official Action Dated Jun. 11, 2010 From the US Patent and Trademark Office Re.: U.S. Appl. No. 11/932,064.
Response Dated Jul. 27, 2011 to Official Action of Apr. 28, 2011 From the US Patent and Trademark Office Re.: U.S. Appl. No. 11/931,889.
Response Dated Jul. 31, 2011 to Official Action of Apr. 14, 2011 From the US Patent and Trademark Office Re.: U.S. Appl. No. 11/932,149.
Sutton et al. "What Is a Pacemaker?", The Foundations of Cardiac Pacing, Part I: An Illustrated Practical Guide to Basic Pacing, Chap. 4.5: 73-74, 1991.
Webster "Electrodes, Leads, and Biocompatibility", Design of Cardiac Pacemakers, IEEE Press, p. 141-144, 1995.
Response Dated Aug. 1, 2010 to Notification of Reasons of Rejection of Apr. 12, 2010 From the Japanese Patent Office Re.: Application No. 2006-525265.
Response Dated Aug. 2, 2010 to Official Action of Mar. 31, 2010 From the US Patent and Trademark Office Re.: U.S. Appl. No. 10/237,263.
Response Dated Jul. 26, 2010 to Official Action of Mar. 25, 2010 From the US Patent and Trademark Office Re.: U.S. Appl. No. 10/804,560.
Official Action Dated Apr. 16, 2010 From the US Patent and Trademark Office Re.: U.S. Appl. No. 11/566,775.
Response Dated Jan. 5, 2010 to Official Action of Oct. 8, 2009 From the US Patent and Trademark Office Re. U.S. Appl. No. 11/566,775.
Response Dated Aug. 24, 2010 to the Supplementary European Search Report of Jun. 7, 2010 From the European Patent Office Re. Application No. 04770468.9.
Official Action Dated Oct. 13, 2010 From the US Patent and Trademark Office Re.: U.S. Appl. No. 10/237,263.
Official Action Dated Oct. 13, 2010 From the US Patent and Trademark Office Re.: U.S. Appl. No. 11/919,491.
Response Dated Jul. 13, 2010 to Notice of Reasons for Rejection of Apr. 27, 2010 From the Japanese Patent Office Re.: Application No. 2007-206282.
Communication Pursuant to Article 94(3) EPC Dated Aug. 11, 2010 From the European Patent Office Re. Application No. 99931435.4.
Official Action Dated Jan. 6, 2011 From the US Patent and Trademark Office Re.: U.S. Appl. No. 11/931,724.
Notice of Allowance Dated Jan. 14, 2011 From the US Patent and Trademark Office Re.: U.S. Appl. No. 11/550,560.
Official Action Dated Jan. 3, 2011 From the US Patent and Trademark Office Re.: U.S. Appl. No. 11/932,149.
Official Action Dated Jan. 24, 2011 From the US Patent and Trademark Office Re.: U.S. Appl. No. 11/919,491.
Official Action Dated Sep. 29, 2010 From the US Patent and Trademark Office Re. U.S. Appl. No. 11/933,168.
Response Dated Feb. 3, 2011 to Official Action of Jan. 3, 2011 From the US Patent and Trademark Office Re.: U.S. Appl. No. 11/932,149.
Response Dated Feb. 7, 2011 to Official Action of Oct. 5, 2010 From the US Patent and Trademark Office Re.: U.S. Appl. No. 10/039,845.
Response Dated Feb. 14, 2011 to Official Action Dated Jan. 13, 2011 From the US Patent and Trademark Office Re.: U.S. Appl. No. 11/931,889.

Response Dated Jan. 31, 2011 to Official Action of Sep. 29, 2010 From the US Patent and Trademark Office Re. U.S. Appl. No. 11/933,168.
Hammond et al. "Motor Innervation of the Cricopharyngeus Muscle by the Recurrent Lanryngeal Nerve", Journal of Applied Physiology, JAP, 83: 89-94, 1997.
Sutton et al. "The Foundation of Cardiac Pacing, Part I: An Illustrated Practical Guide to Basic Pacing", The Bakken Research Center Series, Chap.4: 50-59, 1991.
Official Action Dated Apr. 14, 2011 From the US Patent and Trademark Office Re.: U.S. Appl. No. 11/932,149.
Official Action Dated Apr. 28, 2011 From the US Patent and Trademark Office Re.: U.S. Appl. No. 11/931,889.
Supplemental Response Dated Apr. 18, 2011 to Response of Apr. 10, 2011 to Official Action of Jan. 6, 2011 From the US Patent and Trademark Office Re.: U.S. Appl. No. 11/931,724.
Official Action Dated Jun. 11, 2010 From the US Patent and Trademark Office Re.: U.S. Appl. No. 11/550,560.
Notice of Allowance Dated May 27, 2010 From the US Patent and Trademark Office Re.: U.S. Appl. No. 10/549,216.
Official Action Dated Jun. 28, 2010 From the US Patent and Trademark Office Re.: U.S. Appl. No. 11/931,889.
Supplementary European Search Report Dated Jun. 7, 2010 From the European Patent Office Re. Application No. 04770468.9.
Official Action Dated Mar. 31, 2011 From the US Patent and Trademark Office Re. U.S. Appl. No. 11/673,812.
Response Dated Jul. 27, 2010 to Communication Pursuant to Article 94(3) EPC of Jan. 27, 2010 From the European Patent Office Re. Application No. 07110023.4.
Communication Pursuant to Article 94(3) EPC Dated Aug. 26, 2011 From the European Patent Office Re. Application No. 06759102.4.
Communication Pursuant to Article 94(3) EPC Dated Aug. 26, 2011 From the European Patent Office Re.: Application No. 05853465.2.
Official Action Dated Oct. 10, 2008 From the US Patent and Trademark Office Re. U.S. Appl. No. 09/980,748.
Official Action Dated Sep. 11, 2009 From the US Patent and Trademark Office Re. U.S. Appl. No. 09/980,748.
Official Action Dated May 21, 2007 From the US Patent and Trademark Office Re. U.S. Appl. No. 09/980,748.
Official Action Dated Dec. 23, 2010 From the US Patent and Trademark Office Re. U.S. Appl. No. 09/980,748.
Official Action Dated Feb. 28, 2008 From the US Patent and Trademark Office Re. U.S. Appl. No. 09/980,748.
Official Action Dated Apr. 29, 2009 From the US Patent and Trademark Office Re. U.S. Appl. No. 09/980,748.
Official Action Dated Aug. 30, 2006 From the US Patent and Trademark Office Re. U.S. Appl. No. 09/980,748.
Examination Report Dated Jun. 26, 2009 From the Government of India, Patent Office Re.: Application No. 1161/CHENP/2006.
Response Dated May 4, 2009 to Official Action of Nov. 3, 2008 From the US Patent and Trademark Office Re.: U.S. Appl. No. 10/116,201.
Response Dated Sep. 20, 2010 to Official Action of May 21, 2010 From the US Patent and Trademark Office Re. U.S. Appl. No. 10/116,201.
Response Dated Sep. 27, 2010 to Official Action of Apr. 27, 2010 From the US Patent and Trademark Office Re.: U.S. Appl. No. 10/570,576.
Official Action Dated Aug. 31, 2010 From the US Patent and Trademark Office Re.: U.S. Appl. No. 11/550,560.
Supplementary Partial European Search Report Dated Nov. 4, 2010 From the European Patent Office Re. Application No. 04719312.3.
Response Dated May 6, 2010 to Office Action Dated Jan. 8, 2010 From the State Intellectual Property Office (SIPO) of the People's Republic of China Re.: Application No. 200480012687.5.
Response Dated May 4, 2010 to Official Action of Jan. 5, 2010 From the US Patent and Trademark Office Re.: U.S. Appl. No. 11/802,685.
Office Action Dated Nov. 25, 2010 From the State Intellectual Property Office (SIPO) of the People's Republic of China Re.: Application No. 200480012687.5 and Its Translation Into English.
Response Dated May 15, 2011 to Office Action of Nov. 25, 2010 From the State Intellectual Property Office (SIPO) of the People's Republic of China Re.: Application No. 200480012687.5. & Claims in English.

Translation of Office Action Dated Apr. 20, 2011 From the State Intellectual Property Office (SIPO) of the People's Republic of China Re.: Application No. 200480012687.5.
Official Action Dated Aug. 9, 2011 From the US Patent and Trademark Office Re.: U.S. Appl. No. 11/932,149.
Pre-Appeal Brief Request for Review Dated Aug. 9, 2011 From the US Patent and Trademark Office Re. U.S. Appl. No. 11/933,168.
Response Dated Aug. 31, 2011 to Official Action of Mar. 31, 2011 From the US Patent and Trademark Office Re. U.S. Appl. No. 11/673,812.
Official Action Dated Oct. 11, 2011 From the US Patent and Trademark Office Re.: U.S. Appl. No. 11/919,491.
Official Action Dated Dec. 20, 2011 From the US Patent and Trademark Office Re.: U.S. Appl. No. 10/039,845.
Response Dated Oct. 11, 2011 to Official Action of May 12, 2011 From the US Patent and Trademark Office Re.: U.S. Appl. No. 10/039,845.
Response Dated Dec. 8, 2011 to Office Action of Aug. 3, 2011 From the State Intellectual Property Office (SIPO) of the People's Republic of China Re.: Application No. 200480012687.5.
Notice of Non-Compliant Amendment Dated Dec. 12, 2011 From the US Patent and Trademark Office Re. U.S. Appl. No. 11/792,811.
Official Action Dated Jan. 6, 2012 From the US Patent and Trademark Office Re. U.S. Appl. No. 11/933,168.
Official Action Dated Nov. 8, 2011 From the US Patent and Trademark Office Re.: U.S. Appl. No. 11/931,889.
Office Action Dated Jan. 18, 2012 From the State Intellectual Property Office (SIPO) of the People's Republic of China Re.: Application No. 200480012687.5 and Its Translation Into English.
Office Action Dated Feb. 21, 2012 From the US Patent and Trademark Office Re. U.S. Appl. No. 10/116,201.
Official Action Dated Jan. 4, 2012 From the US Patent and Trademark Office Re. U.S. Appl. No. 11/673,812.
Official Action Dated May 13, 2011 From the US Patent and Trademark Office Re. U.S. Appl. No. 11/933,168.
Official Action Dated Dec. 15, 2011 From the US Patent and Trademark Office Re. U.S. Appl. No. 12/910,943.
Official Action Dated Feb. 15, 2012 From the US Patent and Trademark Office Re. U.S. Appl. No. 11/802,685.
Official Action Dated Feb. 17, 2012 From the US Patent and Trademark Office Re.: U.S. Appl. No. 11/932,149.
Response Dated Dec. 27, 2011 to Communication Pursuant to Article 94(3) EPC of Aug. 26, 2011 From the European Patent Office Re.: Application No. 05853465.2.
Translation of Notice of Reasons for Rejection Dated Jul. 18, 2006 From the Japanese Patent Office Re.: Application No. 09-529637.
Burfeind et al "The Effects of Mechanical Cardiac Stabilization on Left Ventricular Performance", Europeari Journal of Cardio-Thoracic Surgery, 14: 285-289, 1998.
Gomis et al. "Oscillatory Patterns of Electrical Activity in Mouse PancreaticIslets of Langerhans Recorded in Vivo", Pfl?gers Archiv European Journal of Physiology, 432(3): 510-515, 1996.
Hoist et al. "Nervous Control of Pancreatic Endocrine Secretion in Pigs. I. Insulin and Glucagon Responses to Electrical Stimulation of the Vagus Nerves", Acta Physiologica Scandinavica, 111(1): Jan. 1-7, 1981. Abstract.
Holst et al. "Nervous Control of Pancreatic Endocrine Secretion in Pigs. II. The Effect of Pharmacological Blocking Agents on the Response to Vagal Stimulation", Acta Physiologica Scandinavica, 111(1): 9-14, 1981. Abstract.
Horner et al. "Electrode for Recording Direction of Activation, Conduction Velocity and Monophasic Action Potential of Myocardium", American Journal of Physiology, 272(4): H1917-H1927, 1997. Abstract.
Nadal et al. "Homologous and Heterologous Asynchronicity Between Identified ?-, ?- and ?-Cells Within Intact Islets of Langerhans in the Mouse", Journal of Physiology, 517(Pt.1): 85-93, 1999.
Porksen et al. "Section 6: Pulsatile and Phasic Insulin Release in Normal and Diabetic Man. Pulsatile Insulin Secretion: Detection, Regulation, and Role in Diabetes", Diabetes, 51(Suppl.1): S245-S254, Feb. 2002.
Serre et al. "Exendin-(9-39) Is an Inverse Agonist of the Murine Glucagon-Like Peptide-1 Receptor: Implications for Basal intracellular Cyclic Adenosine 3',5'-Monophosphate Levels and ?-Cells Glucose Competence", Endocrinology, 139(11): 4448-4454, 1998.
Wang et al. "Islet Amyloid Polypeptide Tonally Inhibits Beta-, Alpha-, and Delta-Cell Secretion in Isolated Rat Pancreatic Islets", American Journal of Physiology, AJP—Endocrinology and Metabolism, 276(1 Pt.1): E19-E24, 1999.

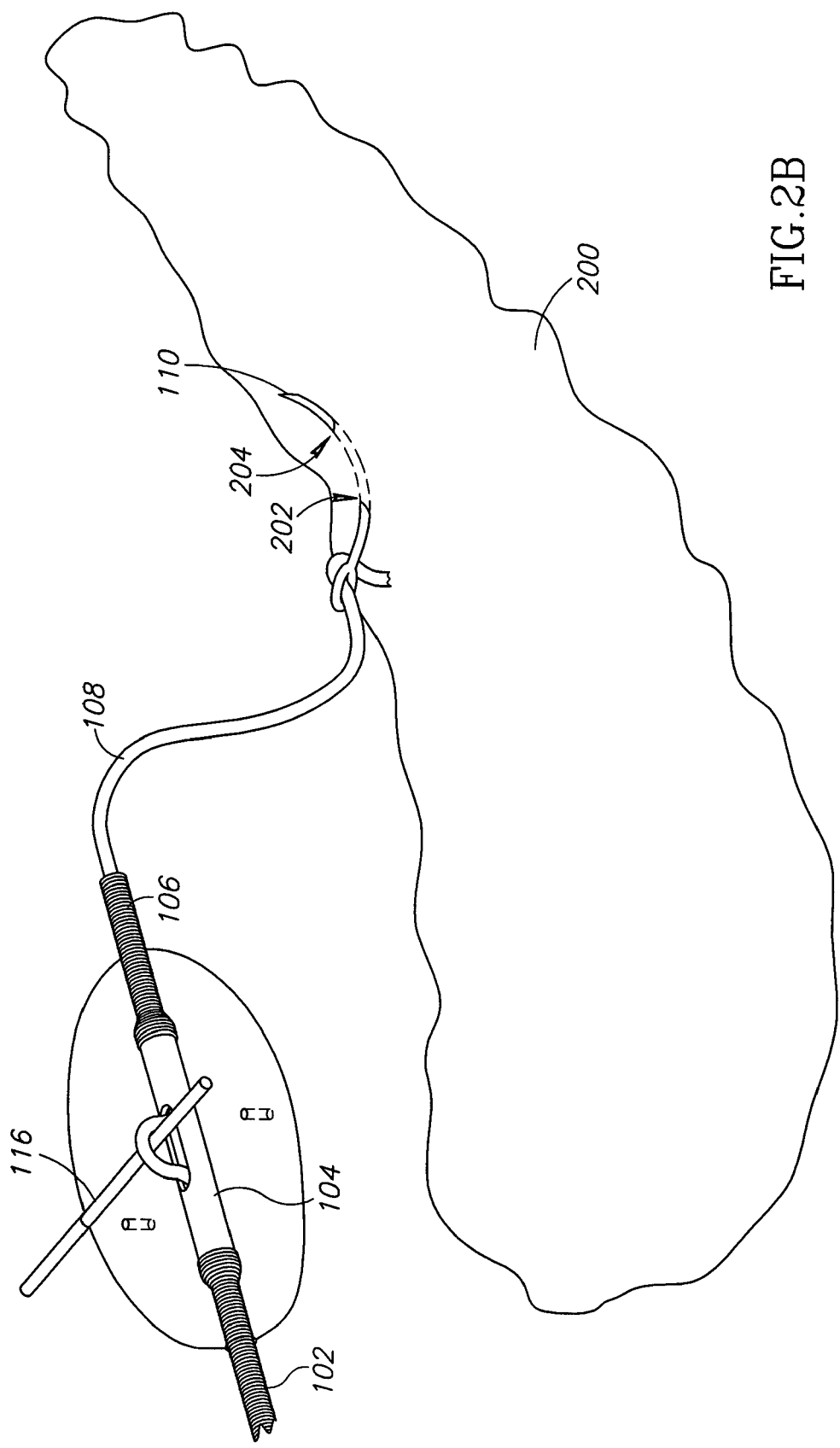

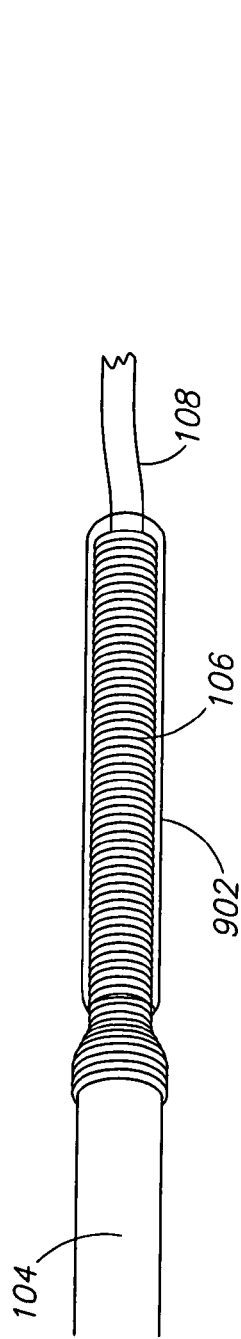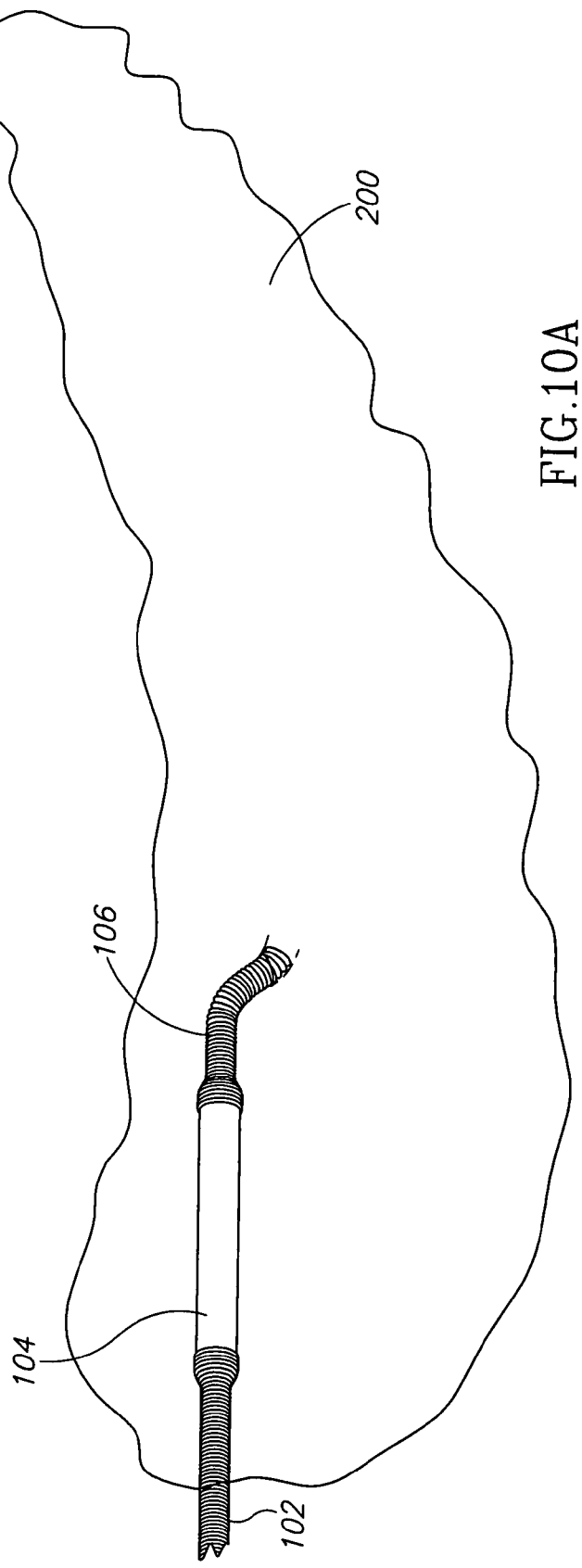
FIG.9
FIG.10A

PANCREAS LEAD

RELATED APPLICATIONS

This Application is a National Phase of PCT Patent Application No. PCT/IL2006/000345 having International Filing Date of Mar. 16, 2006, which is a Continuation-In-Part of PCT Patent Application No. PCT/IL2005/000316 filed on Mar. 18, 2005, and claims the benefit of U.S. Provisional Patent Application No. 60/719,517 filed on Sep. 22, 2005 and U.S. Provisional Patent Application No. 60/719,421 filed on Sep. 22, 2005. The contents of the above Applications are all incorporated herein by reference.

FIELD OF THE INVENTION

The field of the invention relates to electrodes implanted in the body, for example in the pancreas.

BACKGROUND OF THE INVENTION

Electrical stimulation therapy of the pancreas to increase or suppress the production of insulin has been described in published PCT application WO 2004/021858, which describes a variety of configurations of electrodes that might be used for this purpose, including point, line, mesh, plate, ball, and hollow coil-shaped electrodes.

Published PCT application WO 2000/27468 describes an electrode for cardiac stimulation, in the shape of a flexible helical coil. The electrode is coated with a layer of titanium nitride or iridium oxide, which provides a low impedance and high capacitance coupling between the electrode and the heart tissue. The coating, with a microscopic structure that gives it a very high effective surface area, prevents irreversible loss of ions from the tissue and from the electrode. A stiffening stylet may be inserted into the central lumen of the helix. Multi-wire leads are used to independently supply power to several electrodes positioned at different locations in the heart.

The disclosures of these applications are incorporated herein by reference.

SUMMARY OF THE INVENTION

An aspect of some embodiments of the invention relates to implanting an electrical stimulation device, comprising an electrode, in the pancreas or another organ, which device changes its properties after implantation in such a way that it will cause less irritation which could lead to fibrosis and/or other damage to the pancreas. This is done, for example, by one or more of: 1) mechanically decoupling or removing from the device an element which assists in inserting the device into the pancreas, for example an internal stiffening element, but which may not be needed, and may cause damage, after the device is implanted; 2) using an electrode surrounded by a sleeve, and increasing the mechanical coupling of the sleeve to the pancreatic tissue, and/or decreasing the mechanical coupling of the sleeve to the electrode, while maintaining good electrical coupling, after implantation, so that the electrode can move relative to the pancreas without irritating it; and 3) having the device become more flexible, and/or softer, after implanting it, for example by dissolving a stiffening element. One or more of these measures may tend to decrease the stresses that the electrode exerts on the pancreatic tissue, and/or damage that the electrode may do to the pancreatic tissue, as a result of relative motion between the pancreas and the electrode lead.

Optionally, the electrode is used in an organ other than the pancreas, for example in another organ comprising spongy tissue, such as the liver, or in an organ comprising muscular tissue, such as the stomach or elsewhere in the digestive track. Using a very flexible electrode in the wall of the stomach, for example, has the potential advantage over using a stiff electrode, that the flexible electrode may be less likely to penetrate through the wall.

In some embodiments of the invention, the electrode is mechanically decoupled from the lead by using a lead shaped like a helical coil, which provides strain relief to the lead. Alternatively or additionally, strain relief is provided to the lead by having the lead form a loop between a point where the lead is anchored, for example on the duodenum, and a point where the electrode is anchored on the pancreas. Alternatively or additionally, the electrode is mechanically decoupled from the lead by attaching the electrode directly or indirectly to the outer membrane of the pancreas, at a point close to the point where the electrode is implanted in the pancreas, so that any forces exerted on the lead produce stresses at the point of attachment on the outer membrane of the pancreas, rather than on the interior. Stresses on the outer membrane are likely to be less damaging than stresses on the softer interior tissue of the pancreas.

In some embodiments of the invention, there are barb-like tines which keep the electrode imbedded in the pancreas once it is implanted. In some embodiments of the invention, the electrode has a thin coating with high dielectric constant, such as titanium nitride or iridium oxide, which provides a low impedance AC coupling between the electrode and the pancreatic tissue.

An aspect of some embodiments of the invention relates to an electrical stimulation device for implanting in the pancreas, comprising an electrode surrounded by a soft sleeve, which causes less irritation and/or damage to the pancreas than the electrode would cause if it were implanted directly in the pancreas without a sleeve. Optionally, there is relative motion between the electrode and the sleeve.

There is thus provided, according to an exemplary embodiment of the invention, an implant device comprising an electrode for electrical stimulation of the pancreas, the device being adapted to be inserted into the pancreas, and to change at least one of its properties after being inserted into the pancreas, so that it will cause less irritation to the pancreas than before changing said property.

Optionally, the device comprises an inserting element adapted to assist the device in being inserted into the pancreas, and the device is adapted to become mechanically decoupled from the inserting element after the device is inserted into the pancreas.

Optionally, the device is adapted to have the inserting element removed from the pancreas after the device is inserted into the pancreas.

Optionally, the inserting element comprises a needle which is adapted to go through the pancreas and to pull the electrode into the pancreas.

Additionally or alternatively, the inserting element comprises a stiffening element.

Optionally, the electrode is hollow with the stiffening element inside.

Optionally, the stiffening element is a thread coupled to the device, and the device includes a trigger element which releases the thread from being coupled to the device.

Optionally, the thread is coupled to the device by forming a loop which is pulled tight around the trigger element, and the trigger element releases the thread by being pulled out from the loop.

In an embodiment of the invention, the device includes a plate, attached to the device, with a hole in it that an end of the thread is threaded through, and the thread is coupled to the device by having said end of the thread knotted, and the trigger element comprises a cutting implement which releases the thread by cutting off the knotted portion of the thread.

Alternatively, the electrode comprises a crimp in its hollow interior which couples the thread to the device, and an opening which makes a portion of the thread accessible from outside the electrode, and the trigger element comprises a cutting implement which releases the thread by cutting the thread through the opening.

In an embodiment of the invention, the device includes a sleeve surrounding the electrode, adapted to be sufficiently well electrically coupled to the electrode and to the pancreas for electrical stimulation therapy of the pancreas by the electrode, when the device is inserted into the pancreas.

Optionally, the sleeve is adapted to become better coupled mechanically to the pancreas after the device is inserted into the pancreas.

Optionally, the sleeve comprises one or more tines adapted to become set in the pancreas.

Alternatively or additionally, the sleeve is adapted to expand inside pancreas, thereby increasing its mechanical coupling to the pancreas.

Alternatively or additionally, the sleeve is adapted to become glued to the pancreas after the device is inserted into the pancreas.

Optionally, the sleeve is adapted to become mechanically less coupled from the electrode after the device is inserted into the pancreas.

Optionally, the sleeve is sufficiently soft so that it causes less irritation to the pancreas than the electrode would cause if the electrode were directly in contact with the interior of the pancreas without a sleeve.

In an embodiment of the invention, the device is adapted to become one or both of softer and more flexible after the device is inserted into the pancreas.

Optionally, the device comprises a coating of a hard material adapted to dissolve inside the pancreas.

Optionally, the hard material comprises a sugar.

Optionally, the coating is on the outside of the electrode.

Alternatively or additionally, the electrode is hollow, and the coating is inside the electrode, thereby making the electrode stiffer.

In an embodiment of the invention, the device also includes a lead for supplying current to the electrode, the lead being adapted to being anchored at an anchoring point inside the body, and being sufficiently long and flexible so that a one centimeter increase in distance between the anchoring point and the implanted electrode causes the lead to exert a force no greater than 0.01 newtons on the pancreas.

Optionally, the device also includes tines coupled to the electrode, oriented so as to prevent the electrode from moving back out of the pancreas after the electrode is implanted in the pancreas.

Optionally, the electrode is coated with a layer of material capable of reversibly holding at least 100 microcoulombs of ions.

There is further provided, according to an exemplary embodiment of the invention, an implant device comprising:
a) an electrode for electrical stimulation of the pancreas; and
b) a sleeve, through which the electrode is electrically coupled to the pancreas with a resistance less than 20 ohms.

Optionally, the sleeve is one or both of sufficiently soft and sufficiently well-coupled mechanically to the pancreas so that the sleeve causes less irritation to the pancreas than the electrode would if the electrode were directly in contact with the interior of the pancreas without a sleeve.

There is further provided, according to an exemplary embodiment of the invention, a method of implanting an electrical stimulation device in the pancreas, comprising:
a) inserting the device into the pancreas; and
b) changing at least one property of the device after inserting it into the pancreas, so that it causes less irritation to the pancreas.

BRIEF DESCRIPTION OF THE DRAWINGS

Exemplary embodiments of the invention are described in the following sections with reference to the drawings. The drawings are generally not to scale and the same reference numbers are used for the same or related features on different drawings.

FIGS. 2A-2D show schematic perspective views illustrating a method of implanting the device of FIG. 1 in the pancreas, according to an exemplary embodiment of the invention;

FIG. 9 shows a schematic perspective view of an electrode, according to an exemplary embodiment of the invention;

FIGS. 10A and 10B show schematic perspective views illustrating a method of providing strain relief for a lead supplying power to an electrode implanted in the pancreas, according to an exemplary embodiment of the invention;

DETAILED DESCRIPTION OF EXEMPLARY EMBODIMENTS

Figure 1:
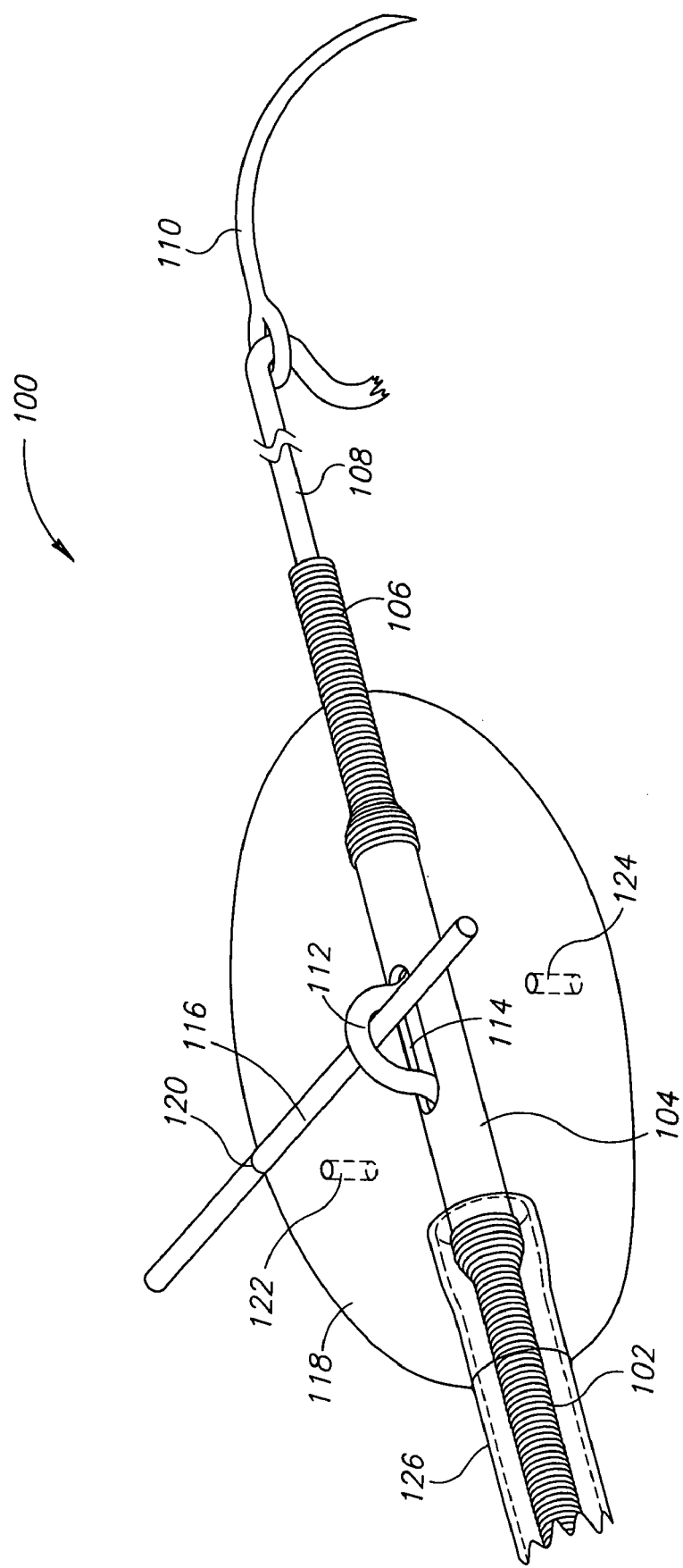
FIG. 1 shows a schematic perspective view of an electrical stimulation device, according to an exemplary embodiment of the invention.

FIG. 1 shows a schematic perspective view of an electrical stimulation device 100 suitable for implantation in the pancreas, according to an embodiment of the invention. Device 100 may also be suitable for implanting in other organs, such as the liver, stomach, heart, and large intestine. Device 100 has features which provide good electrical contact with the pancreas and allow the use of relatively high currents for electrical stimulation therapy over relatively long periods of time, while largely avoiding fibrosis or other damage caused by stresses exerted on the pancreas due to motion of the device relative to the pancreas.

These features provide device 100, in some embodiments thereof, with one or more potential advantages over prior art devices. For example, a lead that is too stiff may not be suitable for use in the pancreas, since it may irritate the pancreas, causing necrosis, or causing fibrosis around the electrode which increases the electrical impedance of the tissue in the vicinity of the electrode. Temporary cardiac pacing wire from A&E Medical Corp., catalog number 025-200, is flexible enough for use as an electrode in the pancreas, and uses tines to anchor it in place. The use of tines for holding an electrode in place is described by U.S. Pat. No. 3,902,501, the disclosure of which is incorporated herein by reference. However, the inventors have found that this wire is too thin to use as an electrode for electrical stimulation therapy in the pancreas, which requires up to 10 mA of current. The wire deteriorates over time when it is used for this purpose, because the electrode surfaces (the exposed surfaces at the ends of the wire) do not reversibly hold enough tissue ions after the ions have interacted with the electrode, leading to irreversible loss of tissue ions (bubble formation) and electrode atoms (etching). To prevent irreversible loss of tissue ions and atoms from an electrode used for electrical stimulation of the pancreas, for example, the electrode optionally can reversibly hold at least 100 microcoulombs of tissue ions which have interacted with the electrode. This allows a 10 mA current to persist for 10 milliseconds before reversing polarity, typical of the currents and durations used in electrical stimulation therapy of the pancreas.

Device 100 comprises an electrode 106, which is optionally in the form of a helical coil. With this form, electrode 106 has great enough surface area so that it can provide sufficient current, for example at least 10 mA over periods of 10 milliseconds, without deteriorating. For example, there is voltage drop of less than 1 volt across the electrode tissue interface, when electrode 106 is providing a current of 10 mA. As noted by Mund et al, U.S. Pat. No. 4,603,704, the disclosure of which is incorporated herein by reference, no corrosion was observed on an electrode with a titanium nitride coating when the voltage drop across the electrode-tissue interface was 1.1 volts, so keeping the voltage drop less than 1 volt for electrode 106 is expected to keep the electrode from deteriorating, with some safety margin.

The helical form of electrode 106 also makes it sufficiently flexible and stretchable that it will tend not to irritate the pancreas, since it can move, bend, and stretch, conforming to changes in the position, orientation and shape of the pancreas, without exerting much force on the surrounding pancreatic tissue. For example, electrode 106 can stretch in length by at least 20% without the material exceeding its infinite-cycle strain limit. As an example of a design for electrode 106 which satisfies these criteria, the electrode is made of grade 2, cold-worked titanium wire, 0.03 mm in diameter, wrapped into a helix with 4 wires in parallel, 0.50 mm in outer diameter, 0.44 mm in inner diameter, and 10 mm in length, with a pitch of 0.15 mm, so there are 66.7 turns. The longitudinal spring constant for this design is 0.0026 N/mm, and the bending stiffness is $3.6 \times 10^{-5}$ N-mm/radian. The resistance of each wire is 18 ohms, so the resistance of the 4 wires in parallel is 4.5 ohms. Alternatively, any of the dimensions is greater or less than these numbers, for example by up to 25%, or by up to 50%, or more, and any other bio-compatible metal is used.

Optionally, an electrical lead 102, which supplies electric power to electrode 106, is also in the form of a helical coil, giving it enough flexibility so that it can move relative to a connector or a power supply, accommodating motion of the pancreas for example, without exerting much force on electrode 106 and hence on the pancreas. Optionally, lead 102 is connected to electrode 106 by a tube 104, whose purpose will be explained below.

In order to provide electrode 106 with enough stiffness to penetrate into the pancreas, a thread 108 passes through electrode 106, at least initially when electrode 106 is implanted, and optionally thread 108 is anchored to device 100, so that thread 108 can be used to pull device 100 into position when it is implanted. Thread 108 extends some distance beyond the end of electrode 106, and the distal end of thread 108 is attached to a surgical needle 110 which is used to implant electrode 106 in the pancreas. Optionally, needle 110 is simply a continuation of thread 108, made of the same material and sharpened at the end. Such a configuration has the potential advantage that there need not be any increase in the diameter of the needle and thread where they are attached, due to an eye of the needle or a knot in the thread, for example. With the needle and thread having a uniform diameter over their length, they are more likely to go smoothly through a hole in the pancreas made by the needle when the electrode is implanted, without exerting undue stress on pancreatic tissue surrounding the opening.

Optionally, thread 108 is anchored to device 100 in such a way that a release mechanism can be used to easily free thread 108 from being anchored. For example, in FIG. 1, thread 108 extends through the entire length of electrode 106 and tube 104, and optionally part way into electrode 102. A loop 112 of thread 108 extends out from an opening 114 in the side of tube 104, and a trigger suture 116, passing through loop 112, prevents loop 112 from going back into tube 104 when someone pulls on thread 108, for example by pulling on needle 110, and prevents thread 108 from being pulled out of device 100 by pulling on thread 108 or needle 110. Trigger suture 116 prevents thread 108 from being pulled out because, for example, a force pulling on thread 108 causes the surface of thread 108 to press against trigger suture 116, and/or against the edge of opening 114, with a force that increases with the force pulling on thread 108, and the resulting friction force on thread 108 is enough to prevent thread 108 from moving. This mechanism is similar to the mechanism by which a thread can be anchored to another body by winding it or knotting it around the body.

Optionally, tube 104, the parts of lead 102 and electrode 106 adjacent to tube 104, loop 112, and part of trigger suture 116, are embedded in a silicone plate 118, which may be sutured to the outer surface of the pancreas to hold device 100 in place after it has been implanted. An end 120 of trigger suture 116 optionally extends outside silicone plate 118, however, so that trigger suture 116 may be removed, after device 100 has been implanted, allowing thread 108 to be removed. Silicone plate 118 optionally has two holes 122 and 124, or a different number of holes, which may be used to suture plate 118 to the outer surface of the pancreas.

Lead 102 is optionally covered by a sheath 126, which optionally has a proximal end outside of the body, and a distal end near the point where lead 102 joins tube 104. Optionally, the distal end of sheath 126 is embedded in silicon plate 118. Sheath 126 is shown as transparent in FIG. 1, so that lead 102 will be visible, but sheath 126 need not be transparent. Sheath 126 also optionally covers lead 102 in any of the embodiments of the invention shown in the drawings, but for clarity sheath 126 is not shown in the other drawings.

Figure 2A:
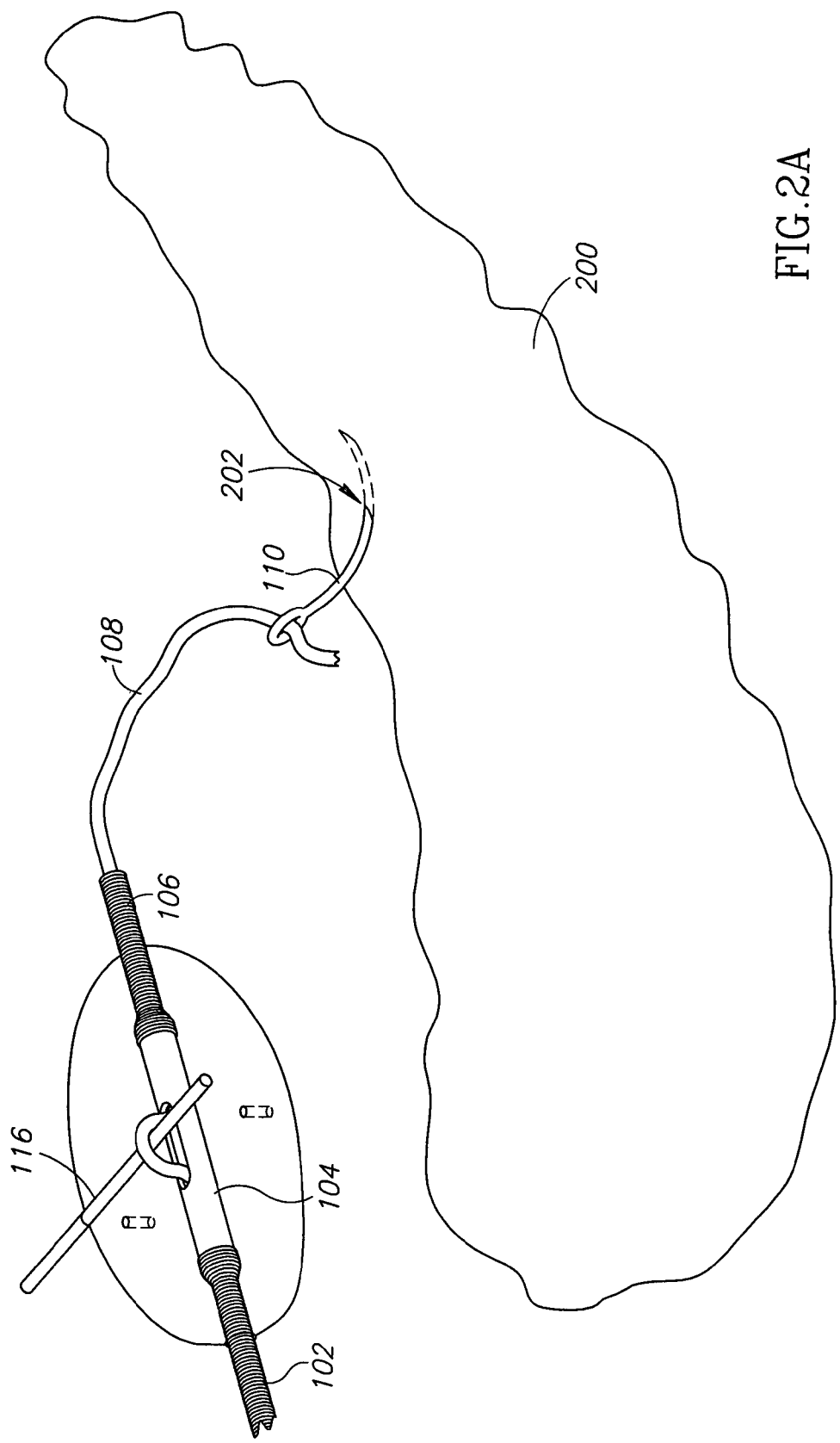
Figure 2C:
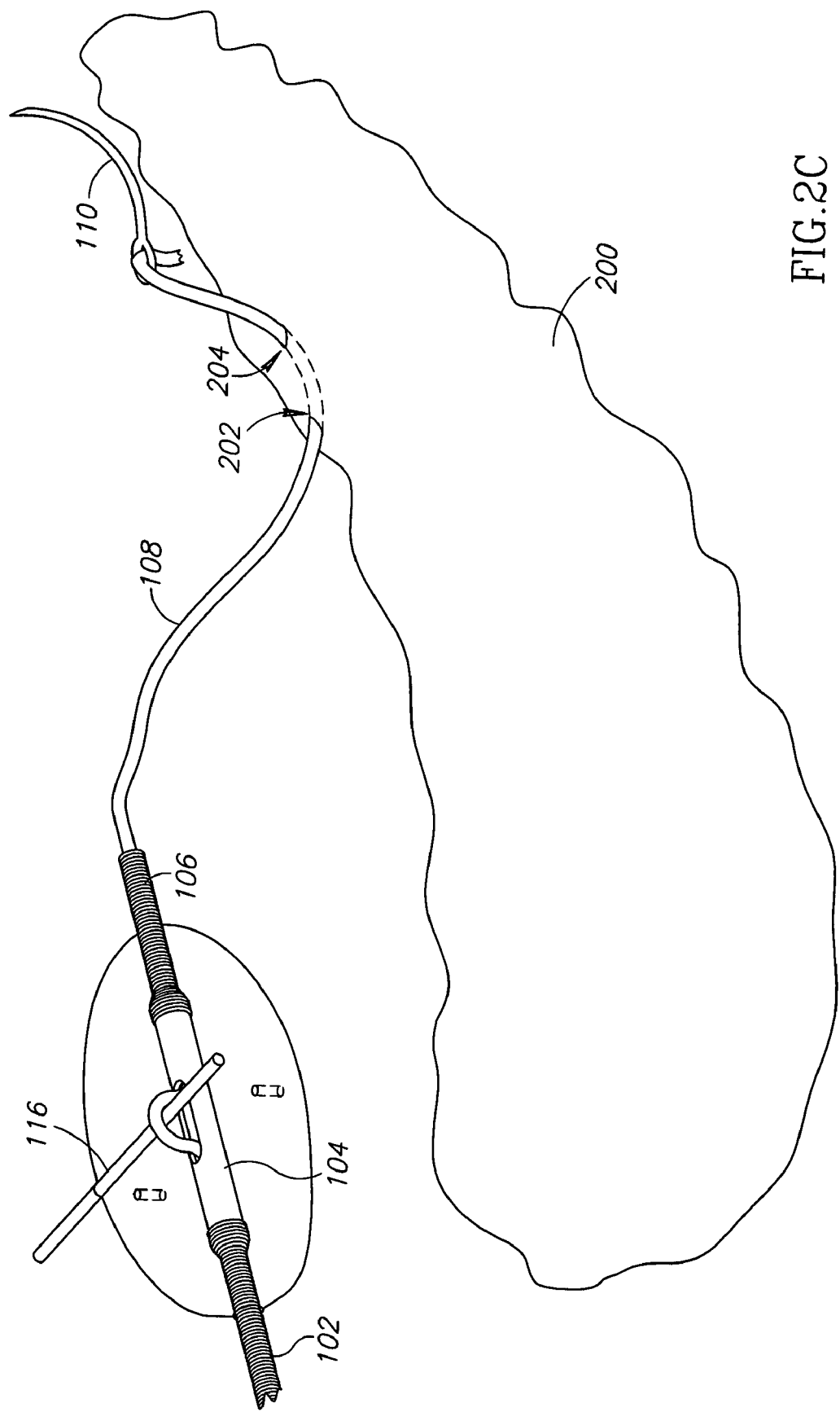
Figure 2D:
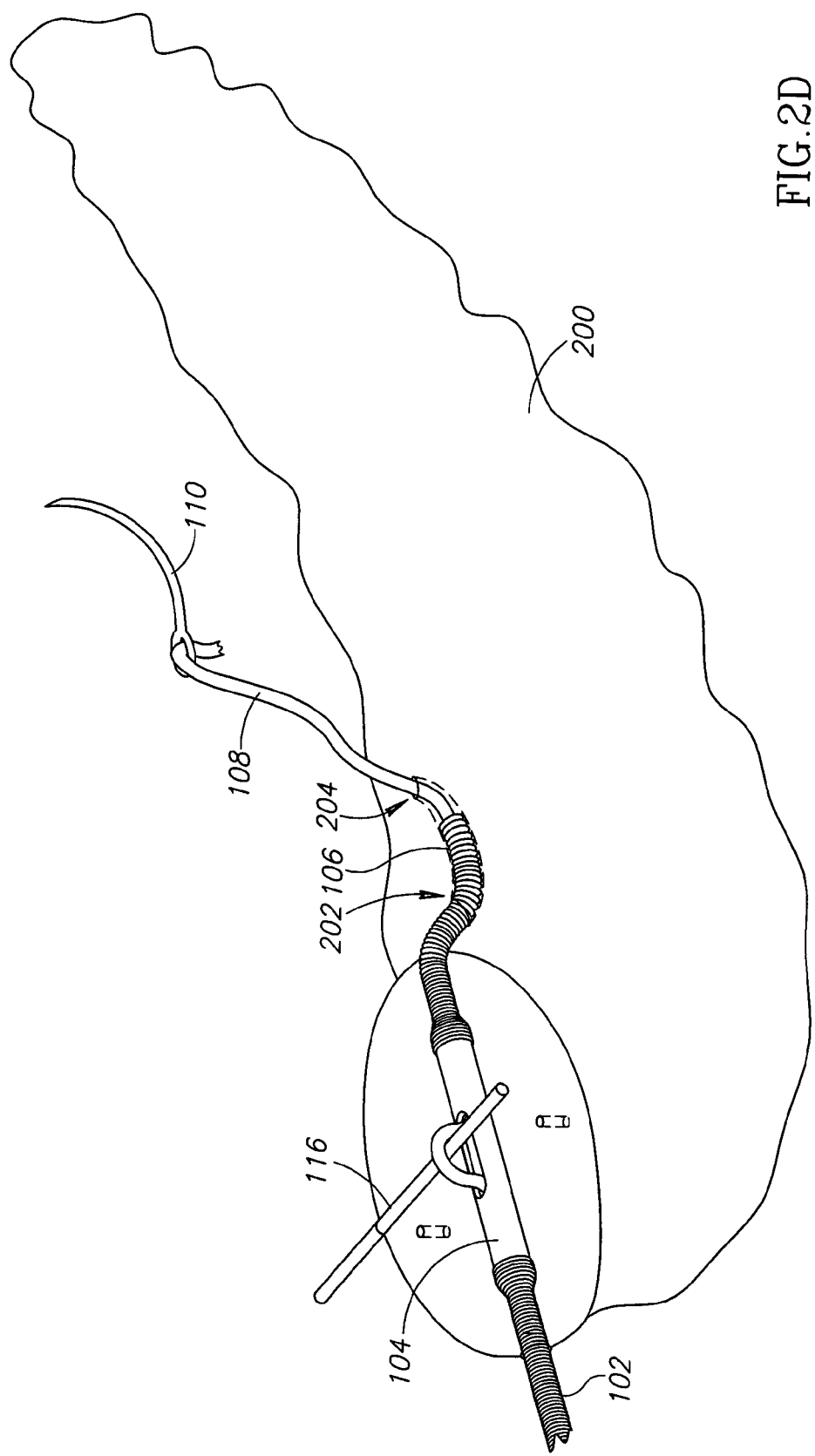

FIGS. 2A-2D schematically illustrate how device 100 is implanted in the pancreas, in an embodiment of the invention. Optionally, the procedure is performed with endoscopic or laparoscopic surgery. In FIG. 2A, surgical needle 110, attached to the end of thread 108, is inserted into pancreas 200. Needle 110 is optionally curved, so that it can be inserted into a location 202 in the pancreas, and can emerge from another location 204, without distorting the shape of the pancreas, as shown in FIG. 2B. Alternatively, needle 110 is straight, and the pancreas is manipulated by the surgeon to make a curved hole. Needle 110 is then pulled through the pancreas and out from location 204, so that thread 108 goes through the pancreas along the curved path followed by the needle, as shown in FIG. 2C. Needle 110 is then pulled, pulling thread 108 with it, until a portion of electrode 106, which surrounds thread 108, passes into the hole made by the needle at location 202, as shown in FIG. 2D. Thread 108 pulls electrode 106 with it when thread 108 is pulled through the hole, because trigger suture 116 locks loop 112 in place, and prevents from thread 108 from sliding relative to tube 104 and electrode 106. Once electrode 106 is inside the hole at location 202, electrode 106 will generally remain in place and continue to make good electrical contact with the pancreas for electrical stimulation therapy.

Optionally, needle 110 is a blunt tapered needle, which has the potential advantage, in the pancreas or other spongy tissue, that it only pushes aside tissue in order to make a hole, and does not produce a cut which may propagate. Alternatively, needle 110 is a cutting tapered needle that cuts tissue in order to make a hole, which may be advantageous to use in muscular tissue, such as the digestive track.

If, as described previously, there is not a separate needle, but needle 110 comprises a distal portion of thread 108 with a sharpened end, then thread 108 is sufficiently stiff, or at least the distal portion of thread 108 is sufficiently stiff, so that the distal portion of thread 108 can act like a needle, making a curved hole through the pancreas. Optionally, the distal portion of thread 108 is curved, and stiff enough to hold its curved shape. Alternatively, the distal portion of thread 108 is not curved, and need not be stiff enough to hold a curved shape, but the pancreas is manipulated by the surgeon so that a straight needle can make a curved hole.

When thread 108 is pulling electrode 106 into the pancreas, the extra stiffness that thread 108 gives to electrode 106 is advantageous, since it helps electrode 106 to go through the hole made by the needle, without collapsing. Once electrode 106 is in place inside the pancreas, however, it may be advantageous for it to be very flexible, so that it moves with the pancreas, and does not exert any stress on the pancreas, when the pancreas moves or bends relative to lead 102. Such stresses could induce fibrosis or other damage to the pancreas. In order to make electrode 106 more flexible, thread 108 is removed from electrode 106 once electrode 106 is in place inside the pancreas. Removing thread 108 also reduces the amount of foreign material in contact with the pancreas, which may also reduce damage to the pancreas. Preferably, thread 108 is removed carefully, to avoid exerting forces that might damage the pancreas during the removal of the thread.

To remove thread 108 from electrode 106, trigger suture 116 is pulled out of loop 112, by pulling on end 120 of trigger suture 116, which end is not embedded in silicone plate 118. This is done, for example, via an endoscope. Once trigger suture 116 is removed, thread 108 is pulled out of electrode 106 and tube 104, for example by pulling on needle 110.

Using trigger suture 116 and loop 112 to lock thread 108 to tube 104 is only one of several possible methods of keeping thread 108 locked to tube 104 until thread 108 is ready to be removed. Other exemplary methods of accomplishing the same goal, according to different embodiments of the invention, are illustrated in FIGS. 3, 4, and 5, and described below.

Silicone plate 118 is optionally sutured to the surface of the pancreas, using holes 122 and 124. This is optionally done before thread 108 is removed from electrode 106. Alternatively, it is done after thread 108 is removed from electrode 106. Although thread 108 is removed because keeping thread 108 inside electrode 106 may irritate the interior of the pancreas, the sutures used to attach silicone plate 118 to the surface of the pancreas may not cause so much irritation, even if the sutures are as stiff as thread 108, since the surface of the pancreas comprises a membrane that is tougher than the soft interior of the pancreas.

Figure 3:
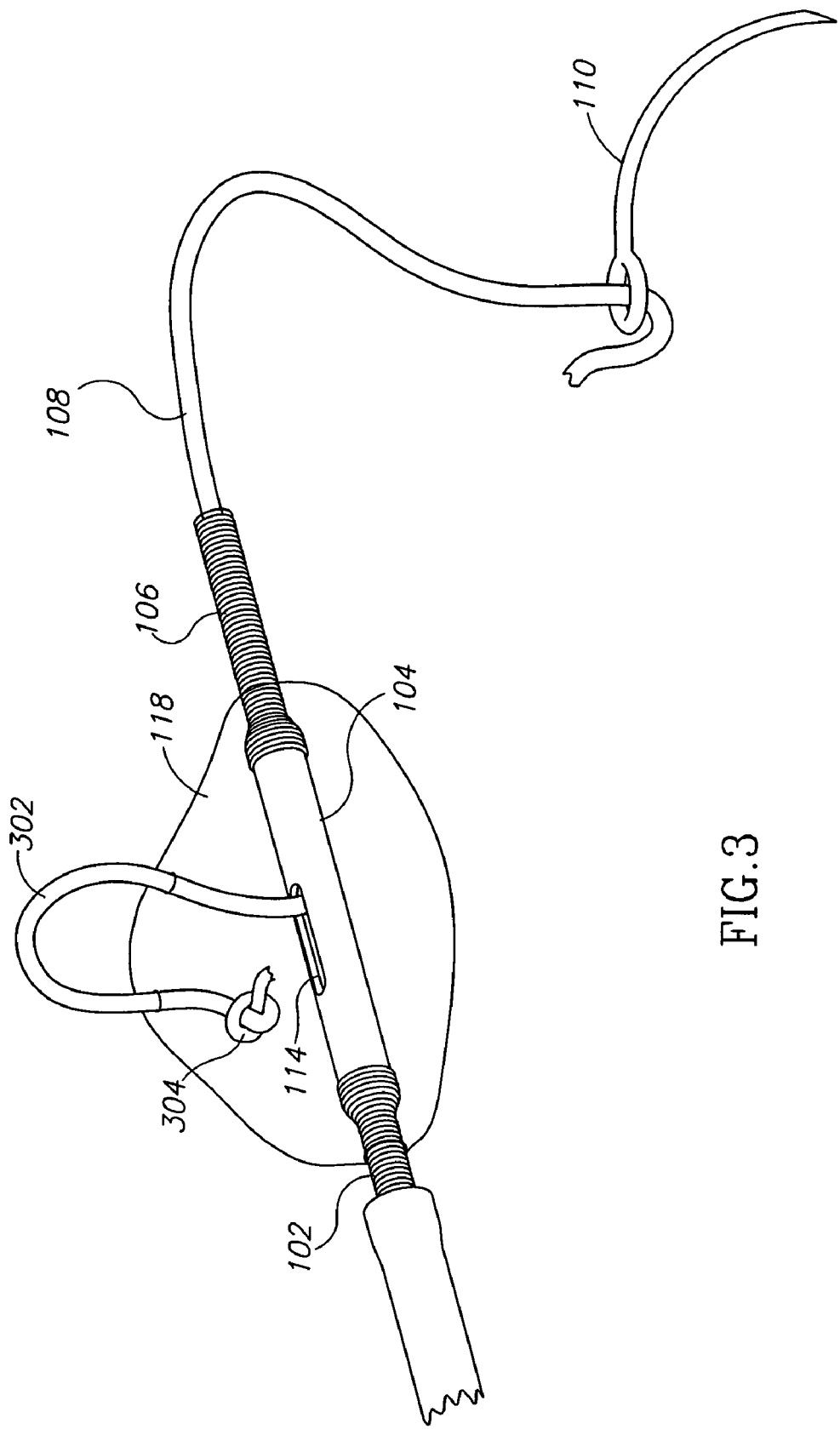
FIGS. 3, 4, and 5 show schematic perspective views of electrical stimulation devices according to other exemplary embodiments of the invention.

In FIG. 3, instead of thread 108 forming a loop 112 emerging from opening 114, a proximal end portion 302 of thread 108 emerges from opening 114, and ends in a knot 304 embedded in silicone plate 118. Knot 304, being wider than the path made by thread 108 in the silicone, keeps the proximal end of thread 108 anchored in silicone plate 118, so thread 108 will not be pulled out of electrode 106 when the distal end of thread 108 is pulled, for example by pulling on needle 110. Optionally, portion 302 of thread 108 comprises a loop that extends outside silicone plate 118, as shown in FIG. 3. To remove thread 108 from electrode 106, once electrode 106 is implanted in the pancreas, portion 302 is cut, so thread 108 will no longer be anchored in silicone plate 118. Pulling on the distal end of thread 108, for example by pulling on needle 110, then removes thread 108 from tube 104 and electrode 106. Optionally, thread 108, silicone plate 118, or both, is coated with Teflon or another low friction material, so that thread 108 will slide more easily when it is pulled out.

Figure 4:
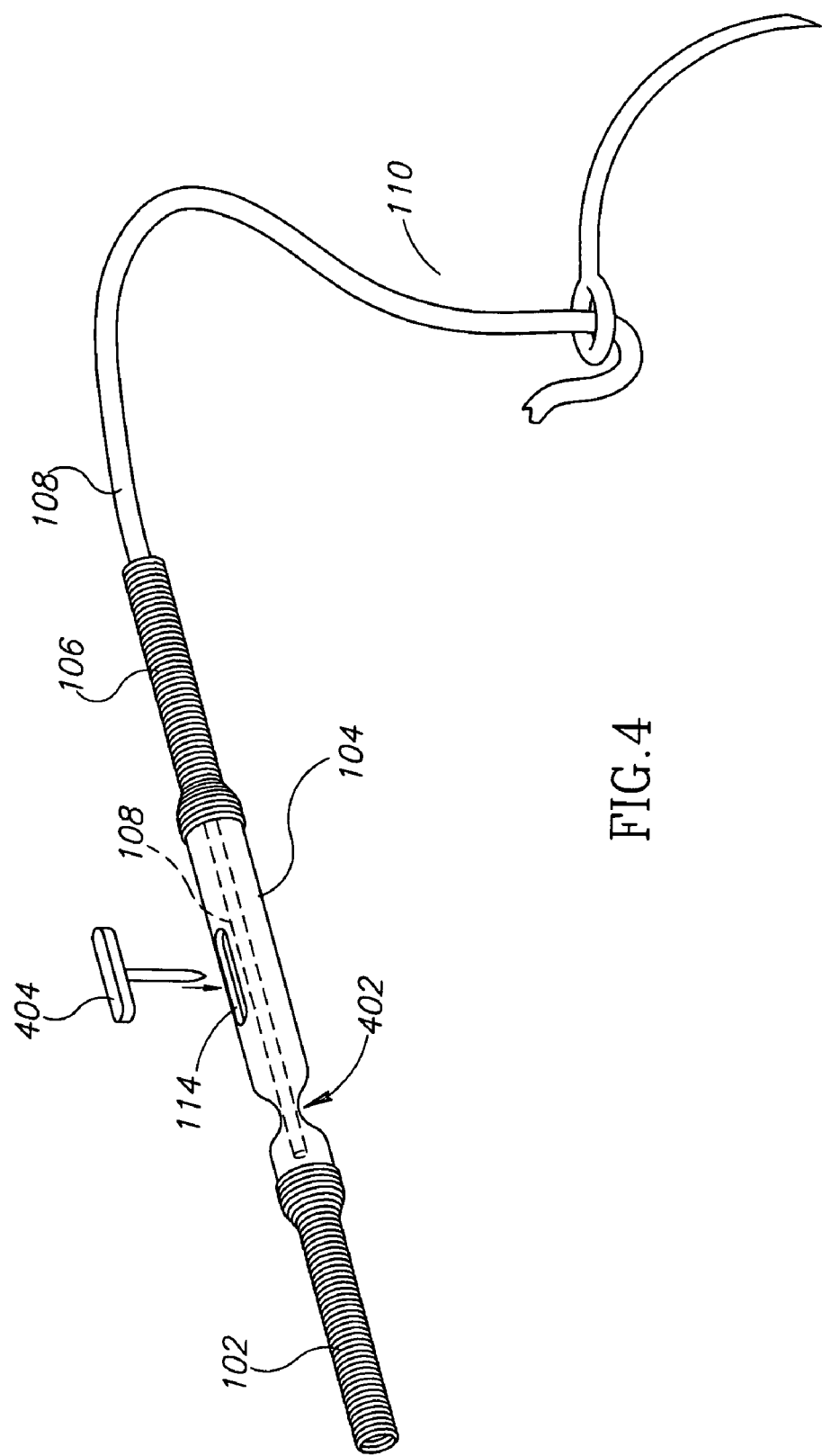
Figure 5:
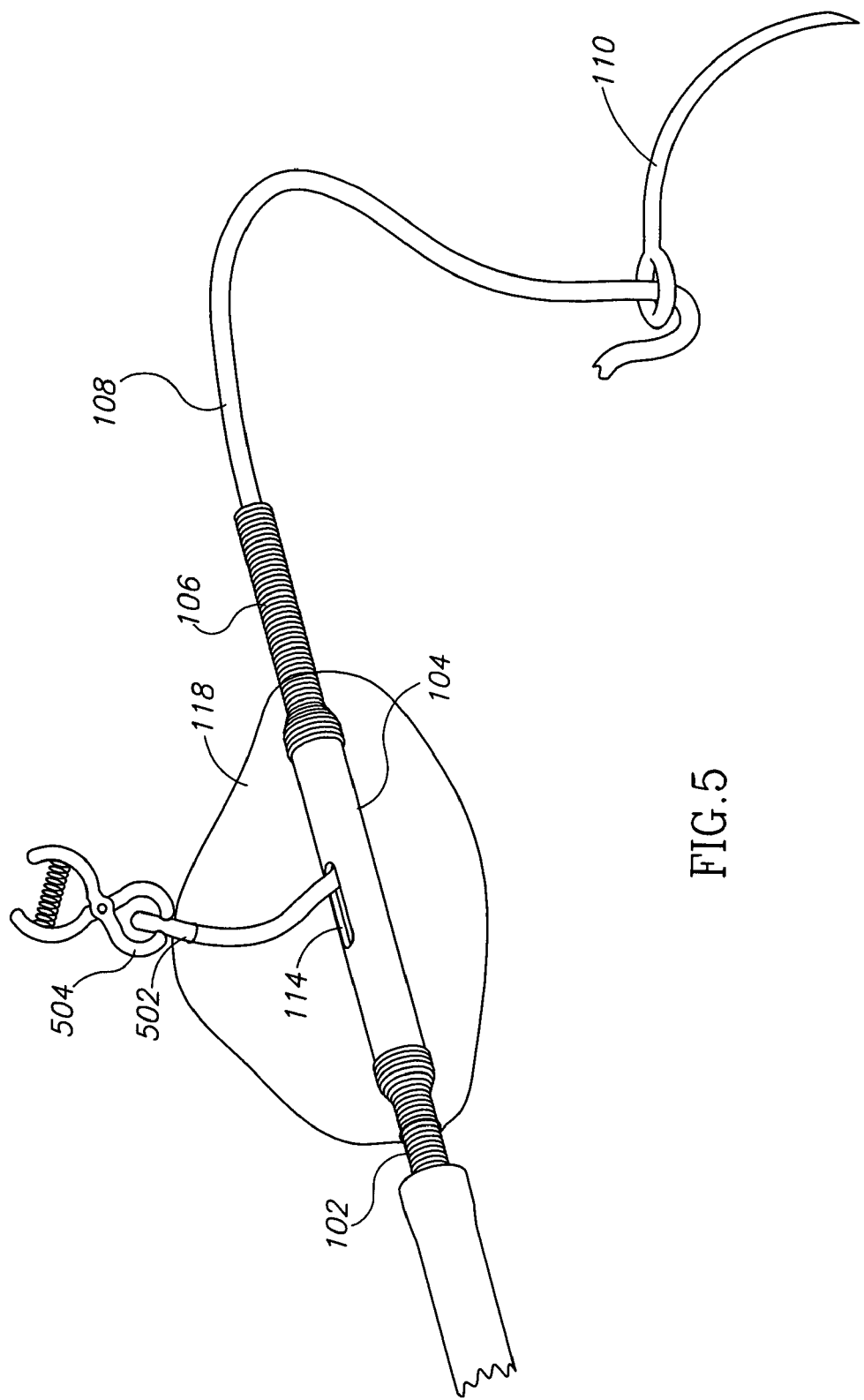

In FIG. 4, the proximal portion of thread 108 does not emerge from tube 104 at all, but thread 108 passes by opening 114. Tube 104 is optionally crimped, at a crimp location 402 proximal to opening 114, and crimp 402 anchors thread 108 to tube 104, preventing thread 108 from being pulled out of tube 104 and electrode 106 if the distal end of thread 108 is pulled. Alternatively or additionally, thread 108 is anchored to tube 104 in another way, for example the proximal end of thread 108 is knotted, and the knot is too big to pass through tube 104. Alternatively or additionally, thread 108 is anchored to lead 102 or to sheath 126, or extends to the outside of the body and is anchored there. When electrode 106 has been implanted in the pancreas and thread 108 is ready to be removed, a sharp instrument 404 is inserted through opening 114 into tube 104, and cuts thread 108. Instrument 404 also optionally cuts through silicone plate 118 to reach opening 114, if there is a silicone plate, although for clarity the silicone plate is not shown in FIG. 4. Alternatively, instrument 404 is imbedded in the silicone plate, for example pre-positioned with its sharp tip inserted into opening 114, or directed toward opening 114, and with the other end of instrument 404 extending outside the silicone plate, so that instrument 404 can be readily manipulated to cut thread 108. Once thread 108 has been cut, it is no longer anchored to tube 104, and may be removed from tube 104 and electrode 106 by pulling on needle 110, for example.

In FIG. 5, a proximal end portion 502 of thread 108 emerges from opening 114 in tube 104, and extends outside silicone plate 118. A clip 504 is clipped to end portion 502 of thread 108. Clip 504 prevents thread 108 from being pulled out of silicone plate 118, since clip 504 is too big to pass through the hole in silicone plate 118 made by thread 108. Hence thread 108 cannot be pulled out of electrode 106 by pulling on the distal end of thread 108, as long as clip 504 is in place. Once electrode 106 has been implanted in the pancreas, and thread 108 is ready to be removed, clip 504 is removed from end portion 502 of thread 108. Thread 108 is then removed from tube 104 and electrode 106 by pulling on needle 110, for example.

Figure 6:
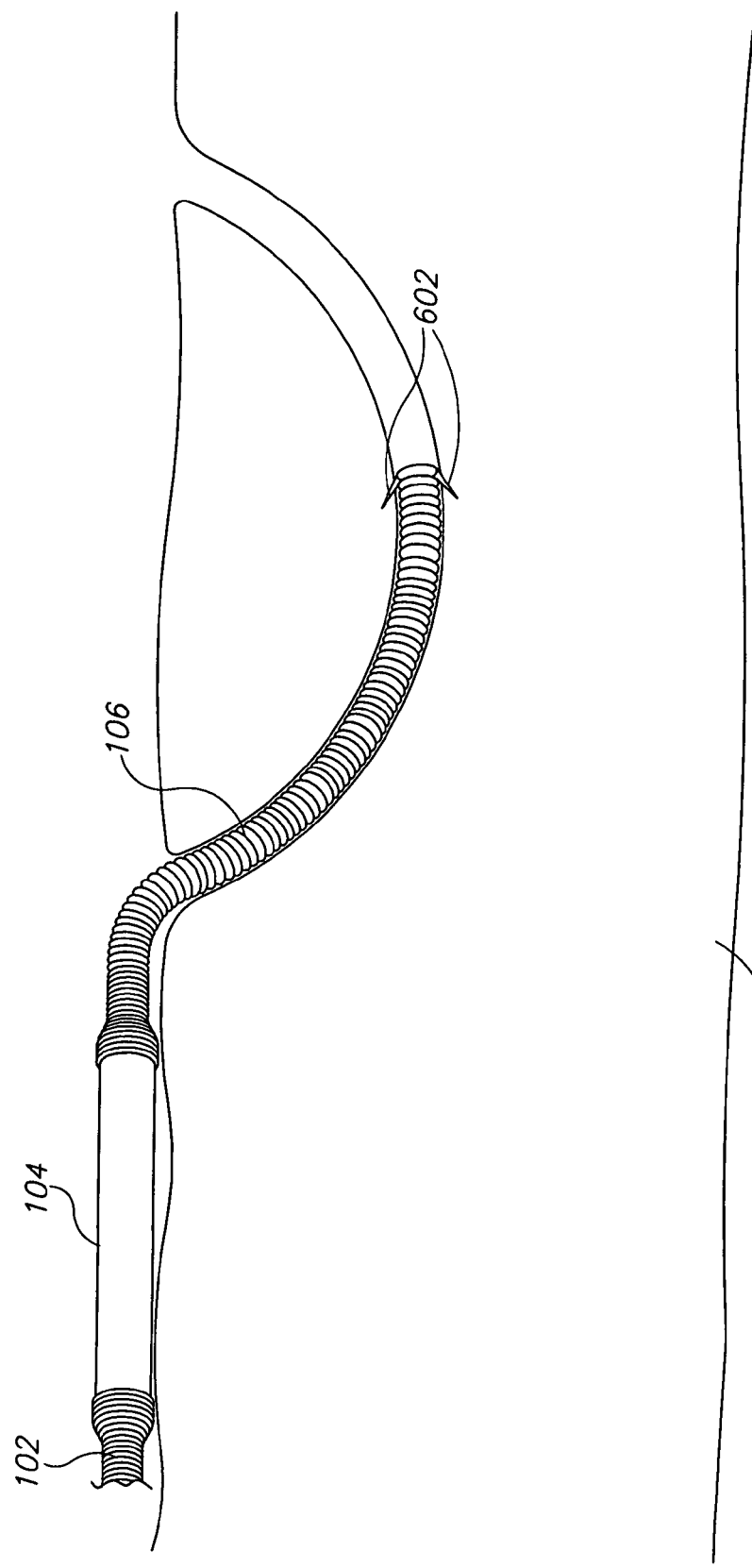
FIGS. 6 and 7 show schematic cross-sectional views of the pancreas, with implanted electrodes according to two different exemplary embodiments of the invention.

FIG. 6 shows a schematic side cross-sectional view of electrode 106 implanted in pancreas 200, according to an embodiment of the invention. Electrode 106 could have been implanted using any of the methods shown in FIGS. 2-5, for example. There are one or more tines 602 on the sides of electrode 106, which point in a direction opposite to the direction that the electrode travels when it is being implanted. These tines, which act like barbs, do not prevent the forward motion of the electrode when it is being implanted, but prevent the electrode from moving backwards, out of the pancreas. Optionally, once the electrode is in a desired location in the pancreas, it is pulled back slightly, for example by pulling on lead 102, to set the tines in the pancreatic tissue. The distance that lead 102 has to be pulled back, in order to set the tines, may be considerably longer than the length of the tines, depending on the axial compliance of lead 102 and electrode 106. Optionally, there are tines along all or much of the length of electrode 106. Alternatively, there are tines only in a small region of electrode 106, for example only at or near the distal end of electrode 106.

Although the tines shown in FIG. 6 are relatively short in length, comparable to the diameter of the electrode 106, optionally the tines are much longer. It is potentially advantageous for the tines to extend to the outside of the pancreas, where the sharp ends of the tines cannot damage the pancreas if the tines move relative to the pancreas. For example, the tines are made of ETFE, and they are 2 to 5 mm long, 0.1 to 0.3 mm thick, and 0.3 to 0.8 mm wide. With this design, the tines are flexible enough to be pulled against electrode 106 when the electrode is pulled into the pancreas, but rigid enough to keep the electrode from pulling out of the pancreas once the tines are set. Other compositions and dimensions for the tines are also possible.

Optionally, electrode 106 has a longitudinal stiffness that increases toward the distal end. Then, if the tines are located only at the distal end, the additional longitudinal stiffness will tend to hold the entire electrode in place, while the proximal end will still be stretchable enough to allow sufficient relative motion between the pancreas and lead 102. Optionally, electrode 106 is provided with additional longitudinal stiffness, without increasing its bending stiffness, by one or more thin fibers which run longitudinally through electrode 106, at least along part of its length, and are bonded to electrode 106 at several locations along its length.

Figure 7:
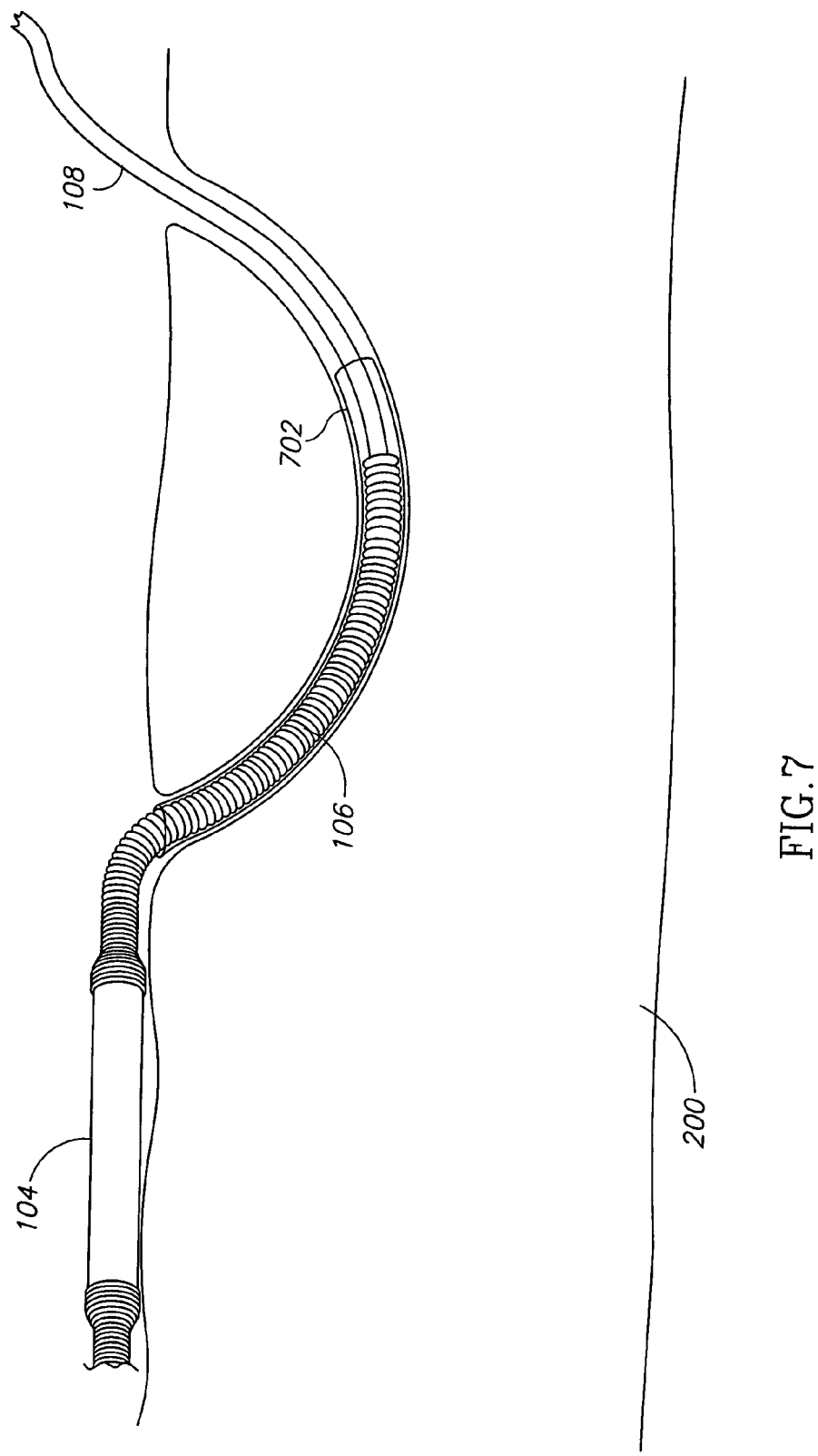

FIG. 7 schematically illustrates another method of keeping electrode 106 from irritating the pancreas, according to an embodiment of the invention. The method shown in FIG. 7 may be used instead of, or in addition to, any of the methods shown in FIGS. 2-5 which involve removing thread 108 from electrode 106 and making electrode 106 more flexible. In FIG. 7, part or all of electrode 106 is surrounded by a sleeve 702. Optionally, particularly if thread 108 is not removed from electrode 106, sleeve 702 also extends over part or all of the portion of thread 108 that is inside the pancreas after electrode 106 is implanted. In an exemplary embodiment of the invention, sleeve 702 is well coupled to electrode 106 electrically, for example with a resistance of less than 20 ohms, or less than 5 ohms, but largely uncoupled from electrode 106 mechanically. For example, sleeve 702 comprises an electrically conductive material, and there is a gap between electrode 106 and sleeve 702 that is filled with a conducting electrolytic fluid, such as a body fluid or a saline solution. Optionally, sleeve 702 is flexible enough so that it can conform to bending and other changes in shape of the pancreas, without exerting forces that could irritate or damage the pancreas.

Once electrode 106 and sleeve 702 are implanted in the pancreas, sleeve 702 is well coupled mechanically to the surrounding pancreatic tissue, and may move together with the pancreas, if the pancreas moves relative to the lead 102. Electrode 106 is largely decoupled mechanically from sleeve 702, so if lead 102 moves relative to the pancreas, electrode 106 may also move relative to the pancreas, sliding inside sleeve 702. But because electrode 106 is not directly in contact with the pancreas mechanically, it does not irritate the pancreas when it moves relative to the pancreas.

Optionally, sleeve 702 becomes well coupled to the pancreas by expanding radially after it is inserted, for example by setting sleeve 702 like a stent, or by absorption of fluid. Alternatively or additionally, sleeve 702 has barbs which couple it to the pancreas once they are set. Alternatively or additionally, sleeve 702 is attached to thread 108, and pulled into the pancreas by thread 108. In that case, thread 108 is optionally detached from sleeve 702 after sleeve 702 is in place, so that thread 108 may be removed. Alternatively or additionally, sleeve 702 becomes well coupled to the pancreas by growth of tissue around it after it is inserted. Alternatively or additionally, sleeve 702 becomes well coupled to the pancreas by an adhesive coating, which does not set until after it is inserted.

In some embodiments of the invention, sleeve 702 does move relative to the pancreas, at least to some extent, when lead 102 moves relative to the pancreas, but sleeve 702 is optionally soft enough so that it does not irritate or damage the pancreas when it moves.

Figure 8:
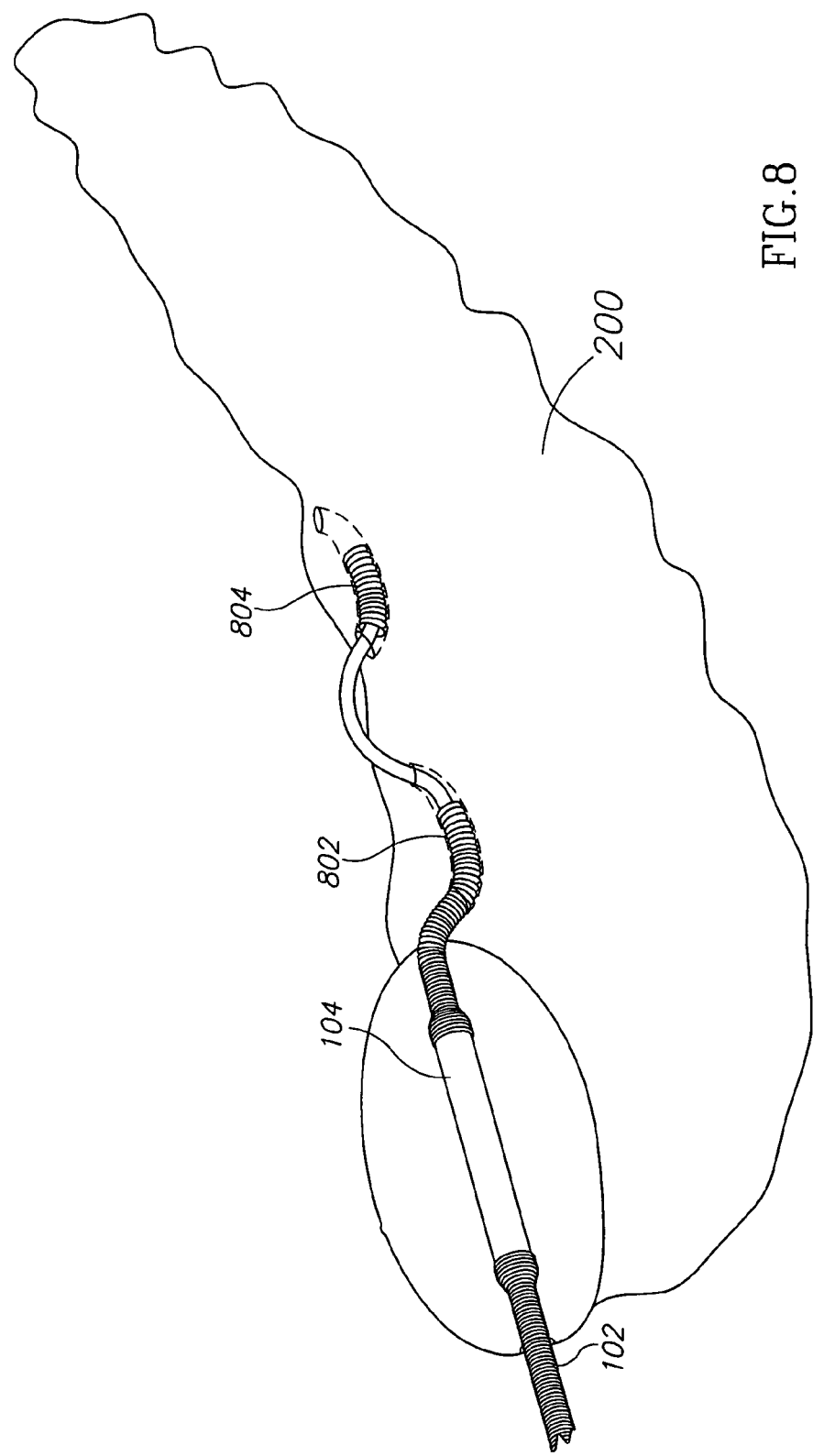
FIG. 8 shows a schematic perspective view of an electrical stimulation device implanted in the pancreas, according to another exemplary embodiment of the invention.

In some embodiments of the invention, needle 110 goes into and out of the pancreas twice, or more times, pulling thread 108 behind it. Optionally, as schematically shown in FIG. 8, there are two electrodes, 802 and 804, arranged along thread 108, and when the electrodes are pulled into place, they are each located at different locations inside the pancreas. Optionally, electrodes 802 and 804 are in fact only a single long electrode, which extends into the pancreas, out of the pancreas, and into the pancreas again, when it is implanted. Optionally, lead 102 comprises a single wire connected to both electrodes 802 and 804, applying the same voltage to both of them. Alternatively lead 102 comprises two separate wires in parallel, one wire connected to each electrode, and different voltages may be applied to the two electrodes. Optionally, instead of only two electrodes there are three or more electrodes, and the needle optionally goes into and out of the pancreas once for each electrode, or there is one long electrode which goes into the pancreas at three or more different locations. Having multiple electrodes, or one long electrode, which go into and out of the pancreas more than once, has the potential advantage that the electrodes are not implanted very deep in the pancreas, and may be less likely to damage the pancreas. Having a single electrode, which enters the pancreas only at one point, has the potential advantage that it may be less likely to pull out of the pancreas accidentally.

Optionally, if there are two or more electrodes pulled by thread 108, thread 108 is attached only to the most distal electrode, which in turn pulls the other electrode or electrodes. However, it may be advantageous for thread 108 to run through all the electrodes, and to be mechanically attached only to the most proximal electrode, or to be mechanically coupled to some extent, for example by friction, to all of the electrodes, in order to avoid exerting a tensile force on one or more of the electrodes when they are pulled by the thread, which could damage or break the electrodes.

Optionally, in addition to or instead of being stiffened by thread 108 running through it, electrode 106 is also stiffened by a soluble coating or filling. FIG. 9 schematically shows electrode 106 with a soluble coating 902, made of sugar, for example, or polyethylene glycol 3350, according to an embodiment of the invention. The coating is produced, for example, by dipping electrode 106 into a saturated sugar solution, then allowing the coating to dry, and optionally buffing the coating to remove any sharp edges.

Coating 902 gives electrode 106 extra stiffness, making it easier to pull electrode 106 into the hole in the pancreas made by the needle, or, in some embodiments of the invention, to push electrode 106 into the pancreas. The coating may also provide lubrication to help pull or push electrode 106 into the pancreas, and for this purpose polyethylene glycol may be particularly suitable. Optionally, if electrode 106 has a soluble coating to stiffen it, then thread 108 is attached only to the end of electrode 106, and is used to pull electrode 106 through the hole made by the needle, rather than thread 108 going through electrode 106 and contributing to the stiffness of electrode 106. Alternatively, thread 108 does go through electrode 106, as in the embodiments shown in the other drawings, and optionally contributes to the stiffness of electrode 106, together with coating 902. Optionally, whether or not thread 108 goes through electrode 106, it is attached to electrode 106 by soluble coating 902, or by a soluble filling, or it is held in place by a soluble crimp, and thread 108 becomes detached from electrode 106 when the soluble material dissolves, for example after a well-defined time. Alternatively, there is no thread 108 at all, and coating 902 makes electrode 106 stiff enough to push it into the pancreas, assisted for example by a sharpened tip, rather than pulling electrode 106 into the pancreas.

Once electrode 106 is implanted inside the pancreas, coating 902 dissolves, completely or partially, making electrode 106 more flexible, so that it will not cause fibrosis or other damage to the pancreas. Optionally, coating 902 comprises a drug, for example particles of a drug slowly released from a matrix, and the drug is released into the pancreas when the coating dissolves. Optionally, particularly if coating 902 is insulating, coating 902 dissolves relatively quickly, for example within 10 or 15 minutes after electrode 106 is implanted in the pancreas, so that electrode 106 may be tested during the surgical procedure to verify that it is in good electrical contact with the pancreas.

Optionally, instead of or in addition to coating electrode 106 on the outside, it is filled on the inside, and/or between the turns of electrode 106 with a similar soluble material that stiffens the electrode, and dissolves after the electrode is implanted.

Figure 10B:
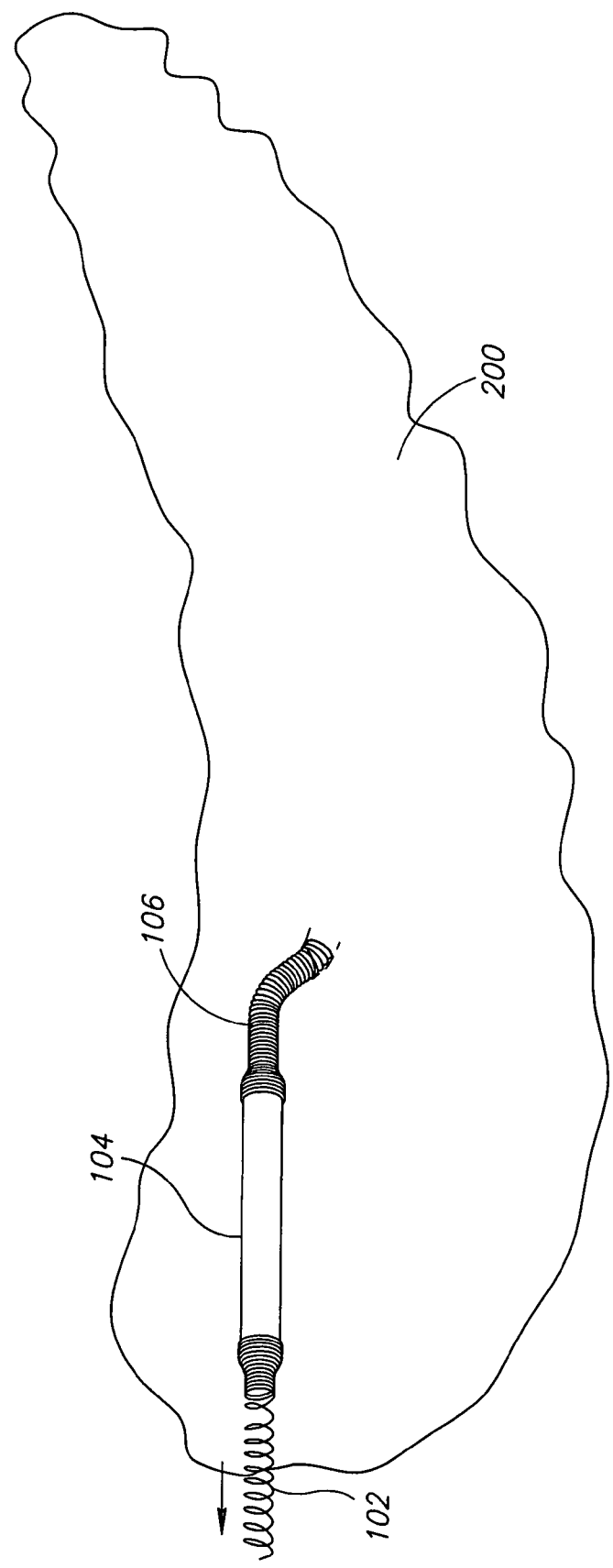

The optionally helical shape of lead 102 helps to decouple it mechanically from electrode 106, allowing the pancreas to move relative to lead 102 without electrode 106 exerting stress on the pancreas. This is illustrated schematically in FIGS. 10A and 10B, according to an embodiment of the invention. In FIG. 10A, electrode 106, implanted in a hole in the pancreas, is attached to tube 104 and lead 102. In FIG. 10B, the other end of lead 102 (not shown in the drawing) is pulled. This can happen, for example, if lead 102 is anchored in the duodenum, and the duodenum moves relative to the pancreas, and lead 102 does not include a loop for strain relief. The force on lead 102 causes the turns of the helix to unwind somewhat, accommodating the force, and transferring little or no force to electrode 106, or to tube 104 which is optionally attached to the pancreas (for example via silicone plate 118, shown in FIG. 1). The helix of lead 102 has a pitch, for example, of between 82 and 85 degrees to the axis, when there is no force pulling on lead 102. As an example of a design for lead 102, it is made of 3 strands in parallel of 0.076 mm MP35N shell with silver core wire, with outer diameter 0.54 mm. The spring constant of lead 102 is comparable to, or as much as an order of magnitude smaller than, the spring constant of electrode 106, for example, depending on the length of lead 102.

If tube 104 is attached to the pancreas, that may further reduce any force on electrode 106 caused by the motion of lead 102. Although forces on tube 104 may then be transferred to the pancreas, this may cause less damage to the pancreas than forces on electrode 106, if tube 104 is attached to the outer membrane of the pancreas, which is tougher than the interior of the pancreas that electrode 106 is in contact with. Additionally or alternatively, tube 104 may be attached to fat layers or other tissue that is adjacent to the pancreas, to prevent or reduce damage to the pancreas.

Figure 11:
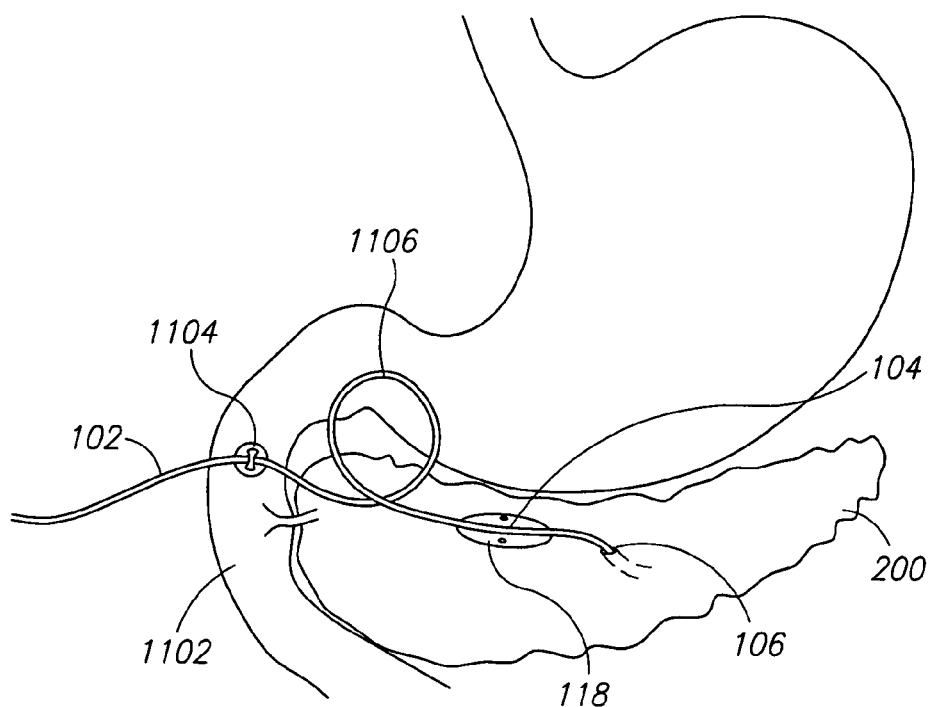
FIG. 11 shows a schematic perspective view illustrating a method of providing strain relief for a lead supplying power to an electrode implanted in the pancreas, according to another exemplary embodiment of the invention.

FIG. 11 schematically illustrates another method of relieving strain in lead 102 according to an embodiment of the invention, instead of or in addition to the strain relief provided by making lead 102 helical, described above. In FIG. 11, as in the previous drawings, lead 102 is attached to tube 104, which is embedded in silicone plate 118 which is sutured to pancreas 200, and electrode 106, implanted in the pancreas, is attached to the other end of tube 104. Lead 102 is also optionally anchored in duodenum 1102, for example using a plate 1104 which is sutured to the duodenum. To accommodate strain in lead 102 due to motion of the duodenum relative to the pancreas, lead 102 optionally forms a loop 1106 between the duodenum and the pancreas. Optionally, lead 102 is sufficiently long and flexible so that a one centimeter increase in distance between anchoring plate 1104 and electrode 106 causes the lead to exert a force no greater than 0.05 newtons on the pancreas, or no greater than 0.01 newtons, or no greater than 0.002 newtons.

Figure 12:
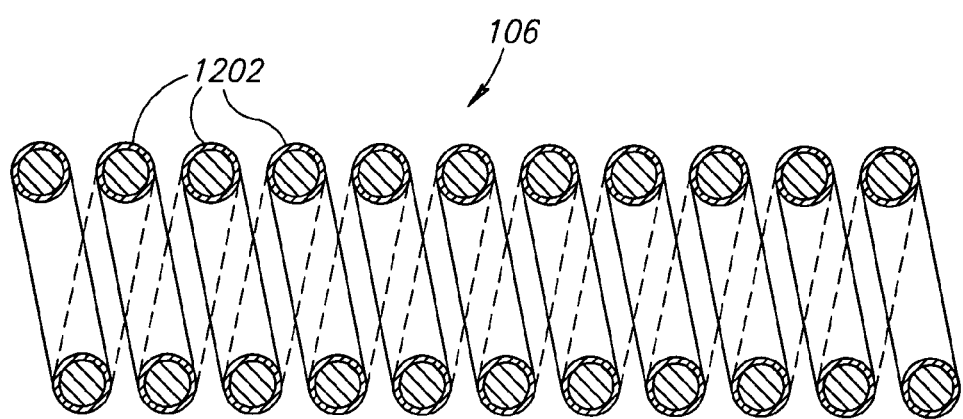
FIG. 12 shows a schematic side cut-away view of part of an electrode, according to an exemplary embodiment of the invention.

To prevent formation of bubbles and other irreversible loss of ions from the pancreatic tissue or from electrode 106 (etching) when tissue ions interact with electrode 106, the electrode is optionally coated with a thin layer of a material with high dielectric constant and high effective surface area. A thin layer 1202 of such a material is shown schematically in FIG. 12, which is a cross-sectional view of electrode 106 according to an embodiment of the invention. Layer 1202 may be, for example, iridium oxide, or titanium nitride. The layer is vapor deposited on the electrode, while the electrode is held on a mandrel, in some embodiments of the invention. Such a vapor deposited layer tends to be thicker on the outer surface of the electrode than on the inner surface, which the vapor cannot reach as easily.

If layer 1202 is thin and has a high dielectric constant and high effective surface area, then it will have a high capacitance, and hence a low impedance to the alternating or pulsed current that the electrode supplies to the pancreas. (In some medical therapies, only alternating or pulsed current is used, in some cases for safety reasons.) The high effective surface area of layer 1202, due to its porous microscopic structure, allows layer 1202 to capture ions that are neutralized by the electrode, so they can be charged again and return to the tissue when the electrode changes polarity, rather than being irreversibly lost from the tissue, which can cause tissue damage. The currents used in electrical stimulation therapy of the pancreas may be relatively lower in frequency and higher in amplitude than the currents typically applied in cardiac stimulation, for example, so having such a surface layer may be more important for an electrode used in the pancreas than for a cardiac electrode.

Optionally, layer 1202 has a capacitance of several microfarads per square millimeter, or several tens of microfarads per square millimeter, many orders of magnitude greater than electrode 106 would have without layer 1202. Optionally, layer 1202 is between 1 and 10 micrometers thick, for example about 5 micrometers thick. Optionally, layer 1202 has a capacity to capture at least 100 microcoulombs of neutralized ions. If layer 1202 extends around the part of the surface of each wire which is on the outer surface of electrode 106, and if electrode 106 is 10 mm long and 0.5 mm in diameter, for example, then an average storage capacity of 4 microcoulombs per square millimeter would give a total of about 100 microcoulombs, which, as noted above, is a typical integrated current used for electrical stimulation therapy of the pancreas. These are typical parameters for vapor deposited titanium nitride coatings used on electrodes inside the body. Any material and method known in the art for coating electrodes used inside the body is optionally used to produce layer 1202, and the parameters may differ from those described above, depending on the material and method used to form layer 1202.

Figure 13:
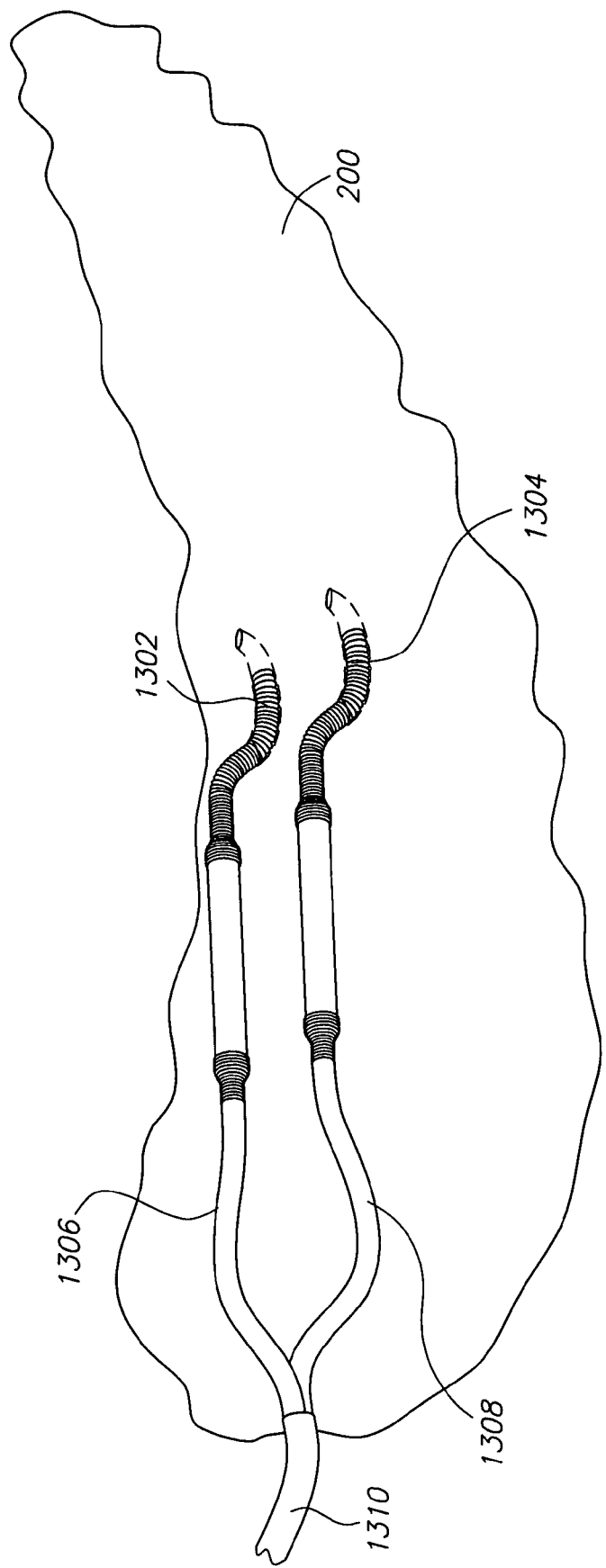
FIG. 13 shows a schematic perspective view of an electrical stimulation device with two electrodes implanted in the pancreas, according to an exemplary embodiment of the invention.

FIG. 13 schematically shows an embodiment of the invention in which two electrodes 1302 and 1304 are implanted in the pancreas in parallel. Each electrode optionally has the configuration of any of the electrodes described previously, and is implanted using any of the methods described previously. Electrodes 1302 and 1304 optionally have their own leads 1306 and 1308, respectively, which split off from a single multi-wire lead 1310. Hence, the voltages applied to electrodes 1302 and 1304 optionally can be controlled independently. Alternatively, leads 1306 and 1308 split off from a single wire in lead 1310, and always have the same voltage. It may be advantageous to make the split close to the pancreas, to minimize the area of the leads in contact with body tissue.

The invention has been described in the context of the best mode for carrying it out. It should be understood that not all features shown in the drawings or described in the associated text may be present in an actual device, in accordance with some embodiments of the invention. Furthermore, variations on the method and apparatus shown are included within the scope of the invention, which is limited only by the claims. Also, features of one embodiment may be provided in conjunction with features of a different embodiment of the invention. As used herein, the terms "have", "include" and "comprise" or their conjugates mean "including but not limited to."

The invention claimed is:

1. An implant device comprising an electrode for electrical stimulation of an in-vivo soft tissue, the device being adapted to be inserted into the tissue, and to change at least one said device's properties after being inserted into the tissue for allowing said electrode to longitudinally deform for conforming to any one of a change in shape, position, or orientation in the tissue so that it will cause less irritation to the tissue than before changing said property;

wherein said longitudinal deforming is by at least 20% of a length of said electrode.

2. An implant device according to claim 1, comprising an inserting element adapted to assist the device in being inserted into the tissue, wherein the device is adapted to become mechanically decoupled from the inserting element after the device is inserted into the tissue.

3. An implant device according to claim 2, adapted to have the inserting element removed from the tissue after the device is inserted into the tissue.

4. An implant device according to claim 2, wherein the inserting element comprises a needle which is adapted to go through the tissue and to pull the electrode into the tissue.

5. An implant device according to claim 2, wherein the inserting element comprises a stiffening element.

6. An implant device according to claim 5, wherein the electrode is hollow with the stiffening element inside.

7. An implant device according to claim 6, wherein the stiffening element is a thread coupled to the device, and including a trigger element which releases the thread from being coupled to the device.

8. An implant device according to claim 7, wherein the thread is coupled to the device by forming a loop which is pulled tight around the trigger element, and the trigger element releases the thread by being pulled out from the loop.

9. An implant device according to claim 7, also including a plate, attached to the device, with a hole in it that an end of the thread is threaded through, wherein the thread is coupled to the device by having said end of the thread knotted, and the trigger element comprises a cutting implement which releases the thread by cutting off the knotted portion of the thread.

10. An implant device according to claim 7, wherein the electrode comprises a crimp in its hollow interior which couples the thread to the device, and an opening which makes a portion of the thread accessible from outside the electrode, and wherein the trigger element comprises a cutting implement which releases the thread by cutting the thread through the opening.

11. An implant device according to claim 1, including a mechanical sleeve surrounding the electrode, adapted to be sufficiently well electrically coupled to the electrode and to the tissue for electrical stimulation therapy of the tissue by the electrode, when the device is inserted into the tissue.

12. An implant device according to claim 11, wherein the sleeve is adapted to become better coupled mechanically to the tissue after the device is inserted into the tissue.

13. An implant device according to claim 12, wherein the sleeve comprises one or more tines adapted to become set in the tissue.

14. An implant device according to claim 12, wherein the sleeve is adapted to expand inside the tissue, thereby increasing its mechanical coupling to the tissue.

15. An implant device according to claim 12, wherein the sleeve is adapted to become glued to the tissue after the device is inserted into the tissue.

16. An implant device according to claim 11, wherein the sleeve is adapted to become mechanically less coupled from the electrode after the device is inserted into the tissue.

17. An implant device according to claim 11, wherein the sleeve is sufficiently soft so that it causes less irritation to the tissue than the electrode would cause if the electrode were directly in contact with the interior of the tissue without a sleeve.

18. An implant device according to claim 1, adapted to become one or both of softer and more flexible after the device is inserted into the tissue.

19. An implant device according to claim 18, comprising a coating of a hard material adapted to dissolve inside the tissue.

20. An implant device according to claim 19, wherein the hard material comprises a sugar.

21. An implant device according to claim 19, wherein the coating is on the outside of the electrode.

22. An implant device according to claim 19, wherein the electrode is hollow, and the coating is inside the electrode, thereby making the electrode stiffer.

23. An implant device according to claim 1, also including a lead for supplying current to the electrode, the lead being adapted to being anchored at an anchoring point inside the body, and being sufficiently long and flexible so that a one centimeter increase in distance between the anchoring point and the implanted electrode causes the lead to exert a force no greater than 0.01 newtons on the tissue.

24. An implant device according to claim 1, also including tines coupled to the electrode, oriented so as to prevent the electrode from moving back out of the tissue after the electrode is implanted in the tissue.

25. An implant device according to claim 1, wherein the electrode is coated with a layer of material capable of reversibly holding at least 100 microcoulombs of ions.

26. An implant device according to claim 1 including a lead for supplying current to said electrode, and wherein said lead is flexibly attached to said electrode.

27. An implant device according to claim 26 wherein at least a portion of said lead is a helical coil.

28. An implant device according to claim 1 wherein said tissue is an abdominal tissue.

29. An implant device according to claim 1 wherein said tissue is the pancreas.

* * * * *